(12) United States Patent
Aso et al.

(10) Patent No.: US 8,841,410 B2
(45) Date of Patent: *Sep. 23, 2014

(54) NITROGEN-CONTAINING CONDENSED RING COMPOUND, NITROGEN-CONTAINING CONDENSED RING POLYMER, ORGANIC THIN FILM, AND ORGANIC THIN FILM ELEMENT

(75) Inventors: Yoshio Aso, Suita (JP); Yutaka Ie, Suita (JP); Masashi Ueta, Suita (JP); Masato Ueda, Tsukuba (JP)

(73) Assignees: Sumitomo Chemical Company, Limited, Tokyo (JP); Osaka University, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/982,410

(22) PCT Filed: Jan. 30, 2012

(86) PCT No.: PCT/JP2012/052018
§ 371 (c)(1),
(2), (4) Date: Aug. 26, 2013

(87) PCT Pub. No.: WO2012/105511
PCT Pub. Date: Aug. 9, 2012

(65) Prior Publication Data
US 2013/0324685 A1 Dec. 5, 2013

(30) Foreign Application Priority Data
Jan. 31, 2011 (JP) .................. P2011-018920

(51) Int. Cl.
*C08G 75/00* (2006.01)
*C07D 513/14* (2006.01)
*C07D 513/04* (2006.01)
*H01L 51/00* (2006.01)
*C08G 61/12* (2006.01)
*H01L 51/05* (2006.01)

(52) U.S. Cl.
CPC .... *H01L 51/0071* (2013.01); *C08G 2261/3223* (2013.01); *G08G 2261/3328* (2013.01); *G08G 2261/124* (2013.01); *C07D 513/14* (2013.01); *C07D 513/04* (2013.01); *H01L 51/0043* (2013.01); *C08G 61/123* (2013.01); *H01L 51/0545* (2013.01); *C08G 2261/3243* (2013.01); *H01L 51/0541* (2013.01); *Y02E 10/549* (2013.01); *C08G 2261/414* (2013.01); *C08G 2261/3246* (2013.01); *C08G 61/126* (2013.01); *G08G 2261/3327* (2013.01); *G08G 2261/3142* (2013.01); *C08G 2261/514* (2013.01); *H01L 51/0036* (2013.01)
USPC ............ 528/378; 528/380; 526/257; 548/148

(58) Field of Classification Search
USPC ............ 528/377, 378, 380; 526/257; 548/148
See application file for complete search history.

(56) References Cited

U.S. PATENT DOCUMENTS

| | | | |
|---|---|---|---|
| 2004/0004215 A1 | 1/2004 | Iechi et al. | |
| 2004/0186266 A1 | 9/2004 | Jiang et al. | |
| 2004/0230021 A1 | 11/2004 | Giles et al. | |
| 2010/0171102 A1* | 7/2010 | Ie et al. | 257/40 |
| 2010/0301314 A1 | 12/2010 | Aso et al. | |
| 2011/0065895 A1* | 3/2011 | Miura et al. | 528/380 |
| 2011/0087034 A1 | 4/2011 | Miyata et al. | |
| 2013/0041123 A1 | 2/2013 | Ie et al. | |

FOREIGN PATENT DOCUMENTS

| | | |
|---|---|---|
| CN | 101798310 A | 8/2010 |
| JP | 05-110069 A | 4/1993 |
| JP | 2004-6476 A | 1/2004 |
| JP | 2004-339516 A | 12/2004 |
| JP | 2010-083785 A | 4/2010 |
| WO | 2008/111461 A1 | 9/2008 |
| WO | 2009/069687 A1 | 6/2009 |
| WO | 2009/099070 A1 | 8/2009 |
| WO | 2010/138650 A1 | 12/2010 |
| WO | 2011/108646 A1 | 9/2011 |

OTHER PUBLICATIONS

International Search Report dated Mar. 6, 2012 in International Application No. PCT/JP2012/052018.
Masashi Ueta, et al., "Development of n-Type Field-effect Transistor Materials Based on Multi-ring-fused System Containing Carbonyl-bridged Thiazole (Carbonyl Kakyo Thiazole o Yusuru Shukugo Takankei n-gata FET Zairyo no Kaihatsu)", Extended Abstracts of the 72nd Autumn Meeting, 2011; The Japan Society of Applied Physics, Aug. 16, 2011, p. 12-478 with translation.
International Preliminary Report on Patentability and Written Opinion issued Aug. 15, 2013 in International Application No. PCT/JP2012/052018.

\* cited by examiner

*Primary Examiner* — Shane Fang
(74) *Attorney, Agent, or Firm* — Sughrue Mion, PLLC

(57) ABSTRACT

It is an object of the present invention to provide a nitrogen-containing condensed ring compound, which can be used as an organic n-type semiconductor having an excellent electron transport property and which is also excellent in terms of solubility in an organic solvent. The nitrogen-containing condensed ring compound of the present invention has a structural unit represented by the following formula (1-1) or formula (1-2):

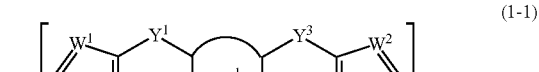

(1-1)

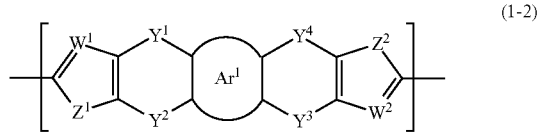

(1-2)

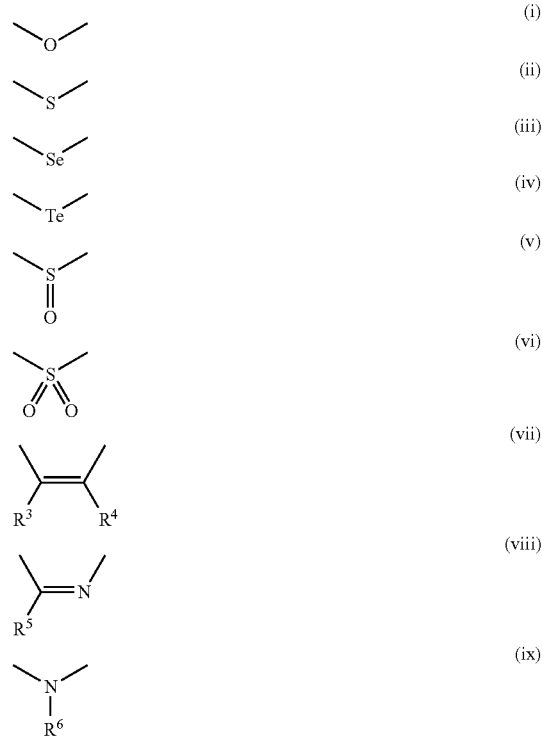

wherein $Ar^1$ represents an aromatic ring; one of $Y^1$ and $Y^2$ represents a single bond, and the other represents —$C(R^{11})(R^{12})$— or —$C(=X^1)$—; one of $Y^3$ and $Y^4$ represents a single bond, and) the other represents —$C(R^{21})(R^{22})$— or —$C(=X^2)$—, and one of $Y^1$ to $Y^4$ represents —$C(R^{11})(R^{12})$— or —$C(R^{21})(R^{22})$—; at least one of $W^1$ and $W^2$ represents —N=; and $Z^1$ and $Z^2$ each represent any one of the groups represented by the formula (i) to the formula (ix).

19 Claims, 11 Drawing Sheets

NITROGEN-CONTAINING CONDENSED RING COMPOUND, NITROGEN-CONTAINING CONDENSED RING POLYMER, ORGANIC THIN FILM, AND ORGANIC THIN FILM ELEMENT

CROSS REFERENCE TO RELATED APPLICATIONS

This application is a National Stage of International Application No. PCT/JP2012/052018 filed Jan. 30, 2012, claiming priority based on Japanese Patent Application No. 2011-018920 filed Jan. 31, 2011, the contents of all of which are incorporated herein by reference in their entirety.

TECHNICAL FIELD

The present invention relates to a nitrogen-containing condensed ring compound, a nitrogen-containing condensed ring polymer, an organic thin film containing these, and an organic thin film element comprising the organic thin film.

BACKGROUND ART

It is anticipated that a thin film containing an organic material having an electron transport property or a hole transport property will be applied to organic thin film elements such as an organic thin film transistor, an organic thin film solar cell, or an optical sensor. Since it is not easy to obtain an organic n-type semiconductor (exhibiting an electron transport property) in comparison with an organic p-type semiconductor (exhibiting a hole transport property), in recent years, intensive studies have been conducted particularly on such an organic n-type semiconductor.

As an electron-transporting material such as an organic n-type semiconductor, a compound in which a fluoroalkyl group is introduced into a thiophene ring is disclosed, for example, in Patent Literature 1. In addition, a polymer consisting of a dithienothiophene group and an arylene group is disclosed, for example, in Patent Literature 2.

CITATION LIST

Patent Literature

Patent Literature 1: U.S. Patent Application Laid-Open No. 2004/186266
Patent Literature 2: Japanese Patent Application Laid-Open No. 2004-339516

SUMMARY OF INVENTION

Technical Problem

However, it is hardly said that the above-mentioned materials have sufficient performance as organic n-type semiconductors, and thus, it has been desired to develop an organic n-type semiconductor whose electron transport property can be further improved.

Moreover, when an organic thin film element is formed, for example, on a flexible substrate, it is advantageous if such an organic thin film can be formed by a coating method. Thus, the material is preferably a material excellent in terms of solubility in an organic solvent. However, to date, it has been extremely difficult to obtain a material, which has a sufficient property as an organic n-type semiconductor and which is also excellent in terms of solubility.

Hence, the present invention has been completed under such circumstances, and it is an object of the present invention to provide materials (a nitrogen-containing condensed ring compound and a nitrogen-containing condensed ring polymer), which can be used as organic n-type semiconductors having an excellent electron transport property and which are also excellent in terms of solubility in an organic solvent. Moreover, it is another object of the present invention to provide an organic thin film containing such a material and an organic thin film element comprising this organic thin film.

Solution to Problem

In order to achieve the aforementioned objects, the nitrogen-containing condensed ring compound of the present invention is characterized in that it has a structural unit represented by the following formula (1-1) or a structural unit represented by the following formula (1-2):

[Chemical Formula 1]

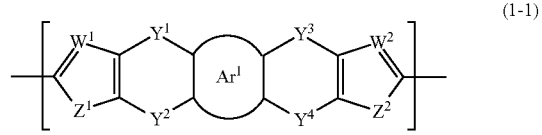

(1-1)

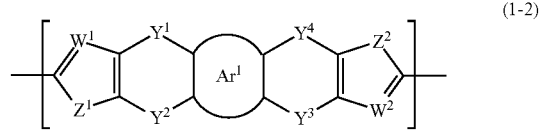

(1-2)

[Chemical Formula 2]

$$\diagdown_O\diagup \quad (i)$$

$$\diagdown_S\diagup \quad (ii)$$

$$\diagdown_{Se}\diagup \quad (iii)$$

$$\diagdown_{Te}\diagup \quad (iv)$$

$$\diagdown\underset{\underset{O}{\|}}{S}\diagup \quad (v)$$

$$\diagdown\underset{\underset{O}{\overset{\|}{\underset{O}{S}}}}{}\diagup \quad (vi)$$

$$\diagdown\underset{R^3}{\overset{}{=}}\underset{R^4}{\overset{}{}} \quad (vii)$$

$$\diagdown\underset{R^5}{\overset{}{=}}N \quad (viii)$$

$$\diagdown\underset{\underset{R^6}{|}}{N}\diagup \quad (ix)$$

wherein, in the formulae (1-1) and (1-2),
Ar$^1$ represents an aromatic ring containing 4 or more carbon atoms and optionally having a substituent,
one of Y$^1$ and Y$^2$ represents a single bond, and the other represents a group represented by —C(R$^{11}$)(R$^{12}$)— or a group represented by —C(=X$^1$)—; one of Y$^3$ and Y$^4$ represents a single bond, and the other represents a group represented by —C(R$^{21}$)(R$^{22}$)— or a group represented by —C(=X$^2$)—, wherein R$^{11}$, R$^{12}$, R$^{21}$ and R$^{22}$ each independently represent a hydrogen atom, a halogen atom, a monovalent group containing an alkane skeleton, or a cyano group, and at least one of Y$^1$, Y$^2$, Y$^3$ and Y$^4$ is a group represented by —C(R$^{11}$)(R$^{12}$)— or a group represented by —C(R$^{21}$)(R$^{22}$)—, wherein at least one of R$^{11}$ and R$^{12}$ and/or at least one of R$^{21}$ and R$^{22}$ are/is a monovalent group containing an alkane skeleton, and X$^1$ and X$^2$ each independently represent an oxygen atom, a sulfur atom, or a group represented by =C(A)$_2$, wherein A represents a hydrogen atom, a halogen atom, or a monovalent group, and a plurality of A may be identical to or different from each other, W$^1$ and W$^2$ each independently represent a group represented by —C(R$^{00}$)— or a group represented by —N=, and at least one of W$^1$ and W$^2$ is a group represented by —N=, and R$^{00}$ represents a hydrogen atom, a halogen atom, or a monovalent group, and Z$^1$ and Z$^2$ each independently represent any one of a group represented by the formula (i), a group represented by the formula (ii), a group represented by the formula (iii), a group represented by the formula (iv), a group represented by the formula (v), a group represented by the formula (vi), a group represented by the formula (vii), a group represented by the formula (viii) and a group represented by the formula (ix) (hereinafter, the same groups as described above are referred to as "groups represented by the formulae (i) to (ix)), wherein the group represented by the formula (vii) and the group represented by the formula (viii) may be flipped horizontally, wherein, in the formula (vii), the formula (viii) and the formula (ix), R$^3$, R$^4$, R$^5$ and R$^6$ each independently represent a hydrogen atom, a halogen atom, or a monovalent group, and R$^3$ and R$^4$ may bind to each other to form a ring together with carbon atoms to which they bind.

Since the above described nitrogen-containing condensed ring compound of the present invention has a structural unit in which a plurality of rings are condensed, π-conjugated planarity between the rings is favorable, and since the ring is a nitrogen-containing condensed ring, a sufficiently low, lowest unoccupied molecular orbital (LUMO) can be achieved. Thus, the present nitrogen-containing condensed ring compound can be used as an organic n-type semiconductor excellent in terms of an electron transport property. Moreover, since the nitrogen-containing condensed ring compound of the present invention has the above described specific structure, it is excellent in terms of solubility in an organic solvent, and thus, it is easy to form an organic thin film by a coating method using the present nitrogen-containing condensed ring compound. Therefore, according to the nitrogen-containing condensed ring compound of the present invention, it becomes possible to produce an organic thin film element with excellent performance.

Furthermore, in a preferred embodiment, the nitrogen-containing condensed ring compound of the present invention is chemically particularly stable and is excellent in terms of environmental stability. Accordingly, by forming an organic thin film using the present nitrogen-containing condensed ring compound, it becomes possible to obtain an organic thin film element, which can exhibit stable performance even in the atmosphere.

In the above described nitrogen-containing condensed ring compound of the present invention, it is preferable that Y$^2$ and Y$^4$ each represent a single bond in the formula (1-1) and the formula (1-2). By having such a structure, an electron transport property and solubility in an organic solvent are further improved.

In the formula (1-1) and the formula (1-2), it is preferable that Ar$^1$ represent a benzene ring or a thiophene ring. Since such a nitrogen-containing condensed ring compound has a structure that facilitates π-conjugation, π-conjugated planarity is improved, and molecules are easily aligned, so that the nitrogen-containing condensed ring compound can exhibit a better electron transport property.

In the formula (1-1) and the formula (1-2), it is preferable that Z$^1$ and Z$^2$ each represent a group represented by the formula (ii). Such a nitrogen-containing condensed ring compound can obtain an electronic state suitable for electron transport as a result of the interaction of a sulfur atom in the formula (ii) with a nitrogen atom that forms a ring with the sulfur atom, and thus, its electron transport property can be further improved.

Further, in the formula (1-1) and the formula (1-2), at least one of W$^1$ and W$^2$ is a group represented by —N=, and it is preferable that both W$^1$ and W$^2$ be groups represented by —N=. Since such a nitrogen-containing condensed ring compound has an electron-accepting property higher than that of a condensed ring compound that does not contain a nitrogen atom, and the LUMO level can be further lowered, the electron transport property of the nitrogen-containing condensed ring compound can be further improved.

In the nitrogen-containing condensed ring compound of the present invention, it is preferable that the structural unit represented by the formula (1-1) be a structural unit represented by the following formula (3-01), and that the structural unit represented by the formula (1-2) be a structural unit represented by the following formula (3-02). Such a nitrogen-containing condensed ring compound is particularly excellent in terms of an electron transport property.

[Chemical Formula 3]

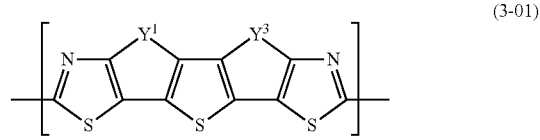

(3-01)

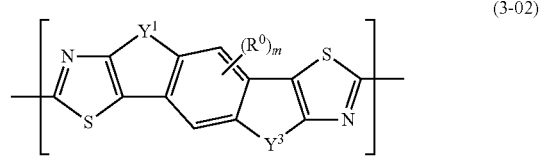

(3-02)

wherein, in the formula (3-01) and the formula (3-02), Y$^1$ and Y$^3$ have the same definitions as those described above, R$^0$ represents a substituent, and m represents an integer of 0 to 2.

The present invention also provides a nitrogen-containing condensed ring polymer, which has a plurality of structural units represented by the following formula (1-1), or has a plurality of structural units represented by the following formula (1-2), or has at least one structural unit represented by the formula (1-1) and at least one structural unit represented by the formula (1-2):

[Chemical Formula 4]

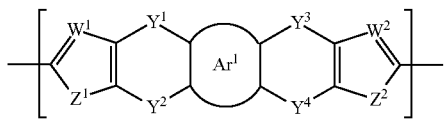
(1-1)

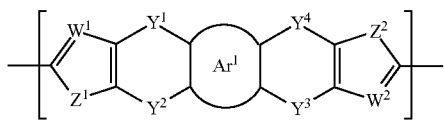
(1-2)

[Chemical Formula 5]

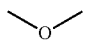 (i)

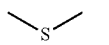 (ii)

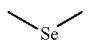 (iii)

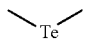 (iv)

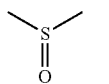 (v)

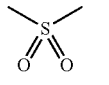 (vi)

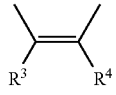 (vii)

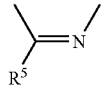 (viii)

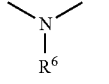 (ix)

wherein, in the formulae (1-1) and (1-2), $Ar^1$ represents an aromatic ring containing 4 or more carbon atoms and optionally having a substituent, one of $Y^1$ and $Y^2$ represents a single bond, and the other represents a group represented by $-C(R^{11})(R^{12})-$ or a group represented by $-C(=X^1)-$; one of $Y^3$ and $Y^4$ represents a single bond, and the other represents a group represented by $-C(R^{21})(R^{22})-$ or a group represented by $-C(=X^2)-$, wherein $R^{11}$, $R^{12}$, $R^{21}$ and $R^{22}$ each independently represent a hydrogen atom, a halogen atom, a monovalent group containing an alkane skeleton, or a cyano group, and at least one of $Y^1$, $Y^2$, $Y^3$ and $Y^4$ is a group represented by $-C(R^{11})(R^{12})-$ or a group represented by $-C(R^{21})(R^{22})-$, wherein at least one of $R^{11}$ and $R^{12}$ and/or at least one of $R^{21}$ and $R^{22}$ are/is a monovalent group containing an alkane skeleton, and $X^1$ and $X^2$ each independently represent an oxygen atom, a sulfur atom, or a group represented by $=C(A)_2$, wherein A represents a hydrogen atom, a halogen atom, or a monovalent group, and a plurality of A may be identical to or different from each other, $W^1$ and $W^2$ each independently represent a group represented by $-C(R^{00})-$ or a group represented by $-N=$, and at least one of $W^1$ and $W^2$ is a group represented by $-N=$, and $R^{00}$ represents a hydrogen atom, a halogen atom, or a monovalent group, and $Z^1$ and $Z^2$ each independently represent any one of groups represented by the formulae (i) to (ix), wherein the group represented by the formula (vii) and the group represented by the formula (viii) may be flipped horizontally, wherein in the formula (vii), the formula (viii) and the formula (ix), $R^3$, $R^4$, $R^5$ and $R^6$ each independently represent a hydrogen atom, a halogen atom, or a monovalent group, and $R^3$ and $R^4$ may bind to each other to form a ring together with carbon atoms to which they bind.

Since the above described nitrogen-containing condensed ring polymer of the present invention has the structural unit(s) represented by the formula (1-1) and/or the formula (1-2), π-conjugated planarity between the rings is favorable and a sufficiently low LUMO can be achieved between the rings, as in the case of the above described nitrogen-containing condensed ring compound of the present invention, the present nitrogen-containing condensed ring polymer can be used as an organic n-type semiconductor excellent in terms of an electron transport property. In addition, the present nitrogen-containing condensed ring polymer is also excellent in terms of solubility in an organic solvent, and thus, it is easy to form an organic thin film by a coating method using the present nitrogen-containing condensed ring polymer. Moreover, in a preferred embodiment, the nitrogen-containing condensed ring polymer of the present invention is chemically particularly stable and is excellent in terms of environmental stability. Accordingly, according to the nitrogen-containing condensed ring polymer of the present invention, it becomes possible to produce an organic thin film element with excellent performance.

In the above described nitrogen-containing condensed ring polymer of the present invention, it is preferable that $Y^2$ and $Y^4$ each represent a single bond in the formula (1-1) and the formula (1-2). By having such a structure, an electron transport property and solubility in an organic solvent are further improved.

In the formula (1-1) and the formula (1-2), it is preferable that $Ar^1$ represent a benzene ring or a thiophene ring. Since such a nitrogen-containing condensed ring polymer has a structure that facilitates π-conjugation, π-conjugated planarity is improved, and molecules are easily aligned, so that the nitrogen-containing condensed ring polymer can exhibit a better electron transport property.

In the formula (1-1) and the formula (1-2), it is preferable that $Z^1$ and $Z^2$ each represent a group represented by the formula (ii). Such a nitrogen-containing condensed ring polymer can obtain an electronic state suitable for electron transport as a result of the interaction of a sulfur atom in the formula (ii) with a nitrogen atom that forms a ring with the sulfur atom, and thus, its electron transport property can be further improved.

Further, in the formula (1-1) and the formula (1-2), at least one of $W^1$ and $W^2$ is a group represented by $-N=$, and it is preferable that both $W^1$ and $W^2$ be groups represented by $-N=$. Since such a nitrogen-containing condensed ring polymer has an electron-accepting property higher than that of a condensed ring polymer that does not contain a nitrogen atom, and the LUMO level can be further lowered, the electron transport property of the nitrogen-containing condensed ring polymer can be further improved.

It is preferable that the nitrogen-containing condensed ring polymer of the present invention have a structural unit represented by the following formula (4) in addition to the above described structural units. By possessing such structural units in combination, it becomes possible to vary the solubility of the nitrogen-containing condensed ring polymer and the mechanical, thermal or electronic properties thereof in a wide range, and thus, desired properties can be easily obtained.

[Chemical Formula 6]

$$-\!\!\left(\!Ar^2\!\right)\!\!- \quad (4)$$

wherein $Ar^2$ represents an aromatic hydrocarbon group optionally having a substituent, a heterocyclic group optionally having a substituent, a group represented by $-CR_a=CR_b-$, or a group represented by $-C\equiv C-$, wherein $R_a$ and $R_b$ each independently represent a hydrogen atom, a halogen atom, an alkyl group containing 1 to 20 carbon atoms and optionally having a substituent, an aryl group containing 6 to 60 carbon atoms and optionally having a substituent, a heterocyclic group containing 4 to 60 carbon atoms and optionally having a substituent, or a cyano group.

The structural unit represented by the formula (4) is particularly preferably a structural unit represented by the following formula (5):

[Chemical Formula 7]

$$(5)$$

[Chemical Formula 8]

$$(xi)$$
$$(xii)$$
$$(xiii)$$
$$(xiv)$$
$$(xv)$$
$$(xvi)$$
$$(xvii)$$
$$(xviii)$$
$$(xix)$$

wherein, in the formula (5), $R^7$ and $R^8$ each independently represent a hydrogen atom, a halogen atom, or a monovalent group, and $Z^3$ represents any one of groups represented by the formulae (xi) to (xix), wherein the group represented by the formula (xvii) and the group represented by the formula (xviii) may be flipped horizontally, and wherein $R^7$ and $R^8$ may bind to each other to form a ring together with carbon atoms to which they bind, wherein in the formula (xvii), the formula (xviii) and the formula (xix), $R^{13}$, $R^{14}$, $R^{15}$ and $R^{16}$ each independently represent a hydrogen atom, a halogen atom, or a monovalent group, and $R^{13}$ and $R^{14}$ may bind to each other to form a ring together with carbon atoms to which they bind.

In the structural unit represented by the formula (5), $Z^3$ is preferably a group represented by the formula (xii). Since a nitrogen-containing condensed ring polymer having such a structural unit can have a stable quinoid structure, it becomes more excellent in terms of an electron transport property.

The present invention further provides an organic thin film containing the above described nitrogen-containing condensed ring compound of the present invention and/or the above described nitrogen-containing condensed ring polymer of the present invention. Since the organic thin film of the present invention contains the nitrogen-containing condensed ring compound and/or nitrogen-containing condensed ring polymer of the present invention, it has a sufficiently low LUMO level and exhibits an excellent electron transport property, and it can be easily formed by a coating method.

The present invention further provides an organic thin film element comprising the above described organic thin film of the present invention. Preferred examples of the organic thin film element include an organic thin film transistor and an organic thin film solar cell. Since such an organic thin film element comprises the organic thin film of the present invention, and this organic thin film has an excellent electron transport property, it can efficiently transport charge injected from electrodes, charge generated as a result of light absorption, etc. Hence, the organic thin film element of the present invention can exhibit excellent performance, and as a result, the organic thin film transistor has high electron mobility, whereas the organic thin film solar cell has high photoelectric conversion efficiency.

Advantageous Effects of Invention

According to the present invention, it becomes possible to provide a nitrogen-containing condensed ring compound and a nitrogen-containing condensed ring polymer, each of which can be used as an organic n-type semiconductor having an excellent electron transport property and each of which is also excellent in terms of solubility in an organic solvent. In addition, according to the present invention, it becomes possible to provide: an organic thin film, which contains the above described nitrogen-containing condensed ring compound and/or nitrogen-containing condensed ring polymer of the present invention, and as a result, exhibits an excellent electron transport property; and an organic thin film element comprising the organic thin film and being capable of exhibiting excellent performance, and particularly, an organic thin film transistor and an organic thin film solar cell.

DESCRIPTION OF EMBODIMENTS

Figure 1:
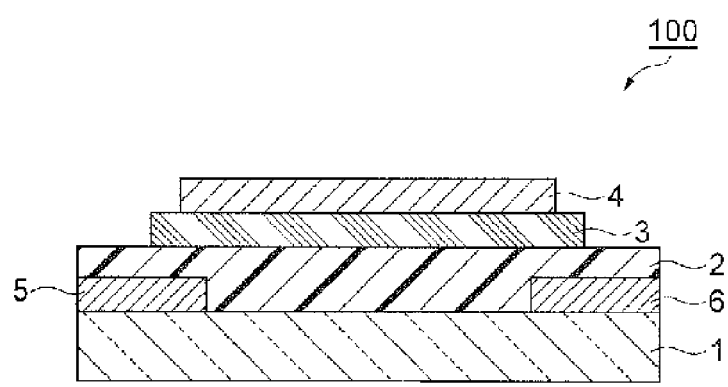
FIG. 1 is a schematic sectional view of an organic thin film transistor according to a first embodiment.

Hereinafter, preferred embodiments of the present invention will be described in detail, while referring to the figures as necessary. It is to be noted that, in the figures, the same reference sign is assigned to the same element, and that overlapping explanation is omitted. Moreover, the positional relationships such as relationships between up and down, and right and left, are based on the positional relationships shown in the figures, unless otherwise specified. Furthermore, the dimensional ratios shown in the figures are provided for illustrative purposes only, and thus, the dimensional ratios applied in the present invention are not limited to those shown in the figures.

[Nitrogen-Containing Condensed Ring Compound]

The nitrogen-containing condensed ring compound according to the present embodiment has a structural unit represented by the following formula (1-1) or a structural unit represented by the following formula (1-2):

[Chemical Formula 9]

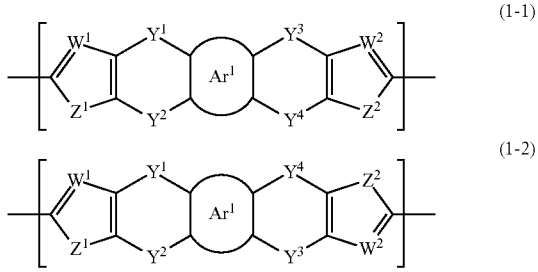

In the formulae (1-1) and (1-2), $Ar^1$ represents an aromatic ring containing 4 or more carbon atoms and optionally having a substituent. Examples of the aromatic ring include a benzenoid aromatic ring and a heteroaromatic ring. In addition, the aromatic ring may be either a single ring or a condensed ring. Of these, the aromatic ring is preferably a single ring or a condensed ring in which 5 or less rings are condensed, more preferably a single ring or a condensed ring in which two rings are condensed, and further preferably a single ring, because it provides more excellent solubility and also facilitates production.

Examples of the benzenoid aromatic ring include a benzene ring, a naphthalene ring, an anthracene ring, a fluorene ring, a pyrene ring, and a perylene ring. Among others, a benzene ring or a naphthalene ring is preferable, and a benzene ring is more preferable. Examples of the heteroaromatic ring include a pyridine ring, a thiophene ring, a thienothiophene ring, a dithienothiophene ring, a benzothiophene ring, a benzodithiophene ring, a dibenzothiophene ring, a pyrrole ring, a quinoline ring, and an indole ring. Among others, a thiophene ring, a thienothiophene ring or a pyridine ring is preferable, and a thiophene ring is more preferable. As an aromatic ring represented by $Ar^1$, a benzene ring or a thiophene ring is preferable.

The aromatic ring represented by $Ar^1$ may optionally have a substituent. As such a substituent, a substituent constituted with 20 or less atoms is preferable, and a substituent constituted with 17 or less atoms is more preferable. Examples of the substituent include: alkyl groups such as a methyl group, an ethyl group, or a propyl group; alkoxy groups such as a methoxy group, an ethoxy group, or a propoxy group; aryl groups such as a phenyl group or a naphthyl group; halogen atoms such as a fluorine atom, a chlorine atom, or a bromine atom; nitro groups; and cyano groups.

In the formulae (1-1) and (1-2), one of $Y^1$ and $Y^2$ represents a single bond, and the other represents a group represented by —C($R^{11}$)($R^{12}$)— or a group represented by —C(=$X^1$)—; one of $Y^3$ and $Y^4$ represents a single bond, and the other represents a group represented by —C($R^{21}$)($R^{22}$)— or a group represented by —C(=$X^2$)—, wherein $R^{11}$, $R^{12}$, $R^{21}$ and $R^{22}$ each independently represent a hydrogen atom, a halogen atom, a monovalent group containing an alkane skeleton, or a cyano group, and at least one of $Y^1$, $Y^2$, $Y^3$ and $Y^4$ is a group represented by —C($R^{11}$)($R^{12}$)— or a group represented by —C($R^{21}$)($R^{22}$)—, wherein at least one of $R^{11}$ and $R^{12}$ and/or at least one of $R^{21}$ and $R^{22}$ are/is a monovalent group containing an alkane skeleton, and $X^1$ and $X^2$ each independently represent an oxygen atom, a sulfur atom, or a group represented by =C(A)$_2$, wherein A represents a hydrogen atom, a halogen atom, or a monovalent group, and a plurality of A may be identical to or different from each other.

At least one of $Y^1$, $Y^2$, $Y^3$ and $Y^4$ is a group represented by —C($R^{11}$)($R^{12}$)— or a group represented by —C($R^{21}$)($R^{22}$)—, and at least one of $R^{11}$ and $R^{12}$ and/or at least one of $R^{21}$ and $R^{22}$ are/is a monovalent group containing an alkane skeleton. Thus, the nitrogen-containing condensed ring compound has a monovalent group containing an alkane skeleton in at least one of $Y^1$, $Y^2$, $Y^3$ and $Y^4$. This is one factor for an intermolecular interaction easily occurring in the nitrogen-containing condensed ring compound, and as a result, molecular orientation is improved, so that the nitrogen-containing condensed ring compound can exhibit a high electron transport property. Moreover, since the nitrogen-containing condensed ring compound contains a monovalent group containing an alkane skeleton, the solubility of the nitrogen-containing condensed ring compound in an organic solvent becomes high, and thus, an organic thin film can be easily formed by a coating method.

In order to obtain such effects more favorably, in the group represented by —C($R^{11}$)($R^{12}$)— or the group represented by —C($R^{11}$)($R^{12}$)—, it is preferable that both $R^{11}$ and $R^{12}$, or both $R^{21}$ and $R^{22}$, be monovalent groups each containing an alkane skeleton. Also, it is preferable that, among $Y^1$ and $Y^2$, $Y^1$ be a group represented by —C($R^{11}$)($R^{12}$)—. Furthermore, it is preferable that, among $Y^3$ and $Y^4$, $Y^3$ be a group represented by —C($R^{21}$)($R^{22}$)—. In particular, it is more preferable that $Y^1$ be a group represented by —C($R^{11}$)($R^{12}$)— and $Y^3$ be a group represented by —C($R^{21}$)($R^{22}$)—. In this case, if all of $R^{11}$, $R^{12}$, $R^{21}$ and $R^{22}$ are monovalent groups each containing an alkane skeleton, the solubility of the nitrogen-containing condensed ring compound in an organic solvent becomes higher.

The term "alkane skeleton" is used herein to mean a chain saturated hydrocarbon represented by the formula $C_nH_{2n+2}$.

The term "monovalent group containing an alkane skeleton" is used to mean a group consisting of such a chain saturated hydrocarbon, or a group having such a chain saturated hydrocarbon. The number of carbon atoms contained in the entire monovalent group containing an alkane skeleton is preferably 1 to 30, more preferably 3 to 24, and further preferably 6 to 20.

The number of carbon atoms possessed by an alkane skeleton in such a monovalent group containing the alkane skeleton is preferably 1 to 30, and more preferably 3 to 24. In particular, since solubility in an organic solvent becomes high, the number of carbon atoms possessed by the alkane skeleton is further preferably 6 to 20. The alkane skeleton may be either a linear or branched alkane skeleton. However, in order to properly align sequences between molecules, a linear alkane skeleton is preferable. On the other hand, in order to achieve higher solubility in organic solvent, a branched alkane skeleton is preferable. The structure of the alkane skeleton can be selected depending on desired properties.

Examples of the monovalent group containing an alkane skeleton include an alkyl group, an alkoxy group, a thioalkyl group, an alkylphenyl group, an alkoxyphenyl group, an alkylthiophenyl group, an alkoxycarbonyl group, an alkylsilyl group, and an alkylamino group. Among others, the monovalent group containing an alkane skeleton is preferably an alkyl group. As such an alkyl group, a linear, branched or cyclic alkyl group containing 1 to 30 carbon atoms is preferable, a linear or branched alkyl group containing 3 to 24 carbon atoms is more preferable, and a linear or branched alkyl group containing 6 to 20 carbon atoms is further preferable. Specific examples of such an alkyl group include a methyl group, an ethyl group, an n-propyl group, an isopropyl group, an n-butyl group, an isobutyl group, a tert-butyl group, a 3-methylbutyl group, a pentyl group, a hexyl group, a 2-ethylhexyl group, a heptyl group, an octyl group, a nonyl group, a decyl group, a lauryl group, a 3,7-dimethyloctyl group, and a 3,7,11-trimethyldodecyl group. A part or all of hydrogen atoms contained in these alkyl groups may be optionally substituted with halogen atoms. The substitutable halogen atom is preferably a fluorine atom. It is to be noted that examples of an alkyl group possessed by a monovalent group containing an alkane skeleton other than an alkyl group are the same as those as described above.

When one of $Y^1$ and $Y^2$, or one of $Y^3$ and $Y^4$, is not the above described group represented by —$C(R^{11})(R^{12})$— or —$C(R^{21})(R^{22})$—, it is a group represented by —$C(=X^1)$— or a group represented by —$C(=X^2)$—. In these formulae, $X^1$ and $X^2$ each independently represent an oxygen atom, a sulfur atom, or a group represented by $=C(A)_2$. A represents a hydrogen atom, a halogen atom, or a monovalent group, and a plurality of A may be identical to or different from each other. Examples of a monovalent group represented by A include an alkyl group, an alkoxy group, an aryl group, a cyano group, a nitro group, an aldehyde group, an acyl group, an alkoxycarbonyl group, a carboxyl group, and a hydroxyl group. These groups may further have a substituent. Examples of an alkyl group, or an alkyl group in a group containing such an alkyl group (e.g. alkoxy group, etc.) in the structure thereof, are the same as those used as the above-mentioned monovalent group containing an alkane skeleton. In addition, as an aryl group, an aryl group containing 6 to 60 carbon atoms is preferable, and an aryl group containing 6 to 20 carbon atoms is more preferable. Examples of such an aryl group include a phenyl group and a naphthyl group.

When the nitrogen-containing condensed ring compound has a group represented by $=C(A)_2$ as $X^1$ or $X^2$, it can further lower a LUMO level. Accordingly, it is preferable that at least one of two A be an electron-withdrawing group, and it is more preferable that both of the two A be electron-withdrawing groups. Preferred examples of such an electron-withdrawing group include a cyano group, a nitro group, an aldehyde group, an acyl group, an alkoxycarbonyl group, a carboxyl group, a hydroxyl group, and a halogen atom. A cyano group, a nitro group, or a halogen atom is more preferable, and a cyano group is further preferable.

As $X^1$ and $X^2$, an oxygen atom or a group represented by $=C(A)_2$ is preferable, and an oxygen atom is more preferable. If $X^1$ or $X^2$ is an oxygen atom, the nitrogen-containing condensed ring compound has a much lower LUMO level, and in a solid state, the oxygen atom easily interacts with a heteroatom in a molecule adjacent thereto, so that a large intermolecular interaction can be achieved and a much higher electron transport property can be exhibited.

In the formulae (1-1) and (1-2), $W^1$ and $W^2$ each independently represent a group represented by —$C(R^{00})$— or a group represented by —$N=$, and at least one of $W^1$ and $W^2$ is a group represented by —$N=$. $R^{00}$ represents a hydrogen atom, a halogen atom, or a monovalent group. Examples of a monovalent group represented by $R^{00}$ are the same as those of the above-mentioned monovalent group represented by A. Both $W^1$ and $W^2$ are preferably —$N=$. Thereby, since the electron-accepting property of the nitrogen-containing condensed ring compound becomes high and a much lower LUMO level can be achieved, the electron transport property of the nitrogen-containing condensed ring compound can be further improved.

In the formulae (1-1) and (1-2), $Z^1$ and $Z^2$ each independently represent any one of groups represented by the following formulae (i) to (ix). $Z^1$ and $Z^2$ each represent preferably any one of the groups represented by the formulae (i), (ii), (iii), (vii), (viii) and (ix), more preferably any one of the groups represented by the formulae (ii) and (vii), and further preferably the group represented by the formula (ii). Among these groups, $Z^1$ and $Z^2$ are preferably the same groups because it facilitates the production of the nitrogen-containing condensed ring compound.

[Chemical Formula 10]

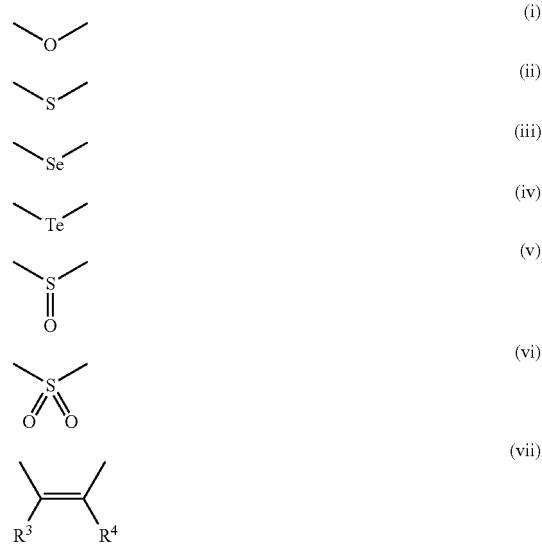

-continued

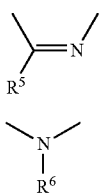

(viii)

(ix)

In the formulae (vii), (viii) and (ix), $R^3$, $R^4$, $R^5$ and $R^6$ each independently represent a hydrogen atom, a halogen atom, or a monovalent group, and $R^3$ and $R^4$ may bind to each other to form a ring together with carbon atoms to which they bind. It is to be noted that the groups represented by the formulae (vii) and (viii) have two binding modes, in which the groups are horizontally flipped, and that both of the two binding modes may be adopted.

Examples of the monovalent groups represented by $R^3$, $R^4$, $R^5$ and $R^6$ include: a linear or branched acyclic group (wherein the term "acyclic group" means a group having no cyclic structures); and a monovalent cyclic group (wherein the term "cyclic group" means a group having a cyclic structure, and this cyclic structure may be either a single ring or a condensed ring, either a hydrocarbon ring or a hetero ring, and either saturated or unsaturated, and it may optionally have a substituent). Moreover, the monovalent group may be either an electron-donating group or an electron-withdrawing group. Examples of such a monovalent group include an alkyl group, an alkoxy group, and an aryl group.

Preferred examples of the groups represented by $R^3$, $R^4$, $R^5$ and $R^6$ include a hydrogen atom, a halogen atom, an alkyl group, an alkoxy group, and an aryl group; and a hydrogen atom, an alkyl group, or an aryl group is more preferable.

The monovalent groups represented by $R^3$, $R^4$, $R^5$ and $R^6$ may optionally have a substituent. As such a substituent, a substituent constituted with 20 or less atoms is preferable, and a substituent constituted with 17 or less atoms is more preferable. Examples of the substituent include: alkyl groups; alkoxy groups such as a methoxy group, an ethoxy group, or a propoxy group; aryl groups such as a phenyl group or a naphthyl group; halogen atoms such as a fluorine atom, a chlorine atom, or a bromine atom; nitro groups; and cyano groups. It is to be noted that halogen atoms include a fluorine atom, a chlorine atom, a bromine atom, and an iodine atom in the present specification.

As alkyl groups used as monovalent groups represented by $R^3$, $R^4$, $R^5$ and $R^6$, or as the above described substituents, an alkyl group containing 1 to 12 carbon atoms is preferable, and an alkyl group containing 1 to 10 carbon atoms is more preferable. In these alkyl groups, a part or all of hydrogen atoms may be optionally substituted with halogen atoms, and such a substitutable halogen atom is preferably a fluorine atom. As such an alkyl group in which a part or all of hydrogen atoms are substituted with fluorine atoms, a fluoroalkyl group containing 1 to 10 carbon atoms is preferable.

Examples of the alkyl group in the monovalent groups represented by $R^3$, $R^4$, $R^5$ and $R^6$, or the above described substituents include a methyl group, an ethyl group, an n-propyl group, an isopropyl group, an n-butyl group, an isobutyl group, a sec-butyl group, and a tert-butyl group. Examples of an alkyl group in a group containing such an alkyl group in the structure thereof (for example, an alkoxy group, an alkylamino group, and an alkoxycarbonyl group), among the monovalent groups represented by $R^3$, $R^4$, $R^5$ and $R^6$, or the above described substituents, are the same as those as described above.

Moreover, as aryl groups used as the monovalent groups represented by $R^3$, $R^4$, $R^5$ and $R^6$, or as the above described substituents, an aryl group containing 6 to 60 carbon atoms is preferable, and an aryl group containing 6 to 20 carbon atoms is more preferable. Specific examples of such an aryl group include a phenyl group and a naphthyl group.

In the nitrogen-containing condensed ring compound of the present embodiment, it is preferable that the structural unit represented by the formula (1-1) and the structural unit represented by the formula (1-2) be structures having line symmetry or point symmetry, and it is more preferable that these structural units be structures having point symmetry. Thereby, it can be anticipated that the number of sites in which an intermolecular interaction occurs will be increased in the nitrogen-containing condensed ring compound, and as a result, since such intermolecular interactions are increased and molecules easily become aligned, the electron transport property tends to be further improved. In order that the structural unit represented by the formula (1-1) and the structural unit represented by the formula (1-2) can be structures having line symmetry or point symmetry, it is preferable that groups in individual structural units, which are positioned in a line-symmetric or point-symmetric relationship to each other, be the same groups.

The nitrogen-containing condensed ring compound according to the present embodiment is preferably a compound wherein, in the formula (1-1) and the formula (1-2), both $Y^2$ and $Y^4$ are single bonds. In this case, in the nitrogen-containing condensed ring compound, the structural unit represented by the formula (1-1) can be a structural unit represented by the following formula (2-1), and the structural unit represented by the formula (1-2) can be a structural unit represented by the following formula (2-2). The groups indicated with individual symbols in the formulae (2-1) and the formula (2-2) have the same definitions as those of the groups indicated with the same symbols as in the formulae (1-1) and the formula (1-2). However, since the sites in the formulae (2-1) and the formula (2-2), which correspond to $Y^2$ and $Y^4$ in the formula (1-1) and the formula (1-2), are single bonds, $Y^1$ is a group represented by —$C(R^{11})(R^{12})$— or a group represented by —$C(=X^1)$—, $Y^3$ is a group represented by —$C(R^{21})(R^{22})$— or a group represented by —$C(=X^2)$—, and further, at least one of $Y^1$ and $Y^3$ is a group represented by —$C(R^{11})(R^{12})$— or a group represented by —$C(R^{21})(R^{22})$—.

[Chemical Formula 11]

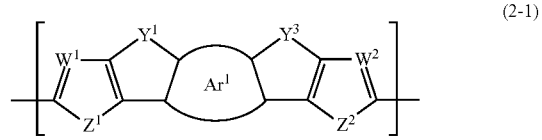

(2-1)

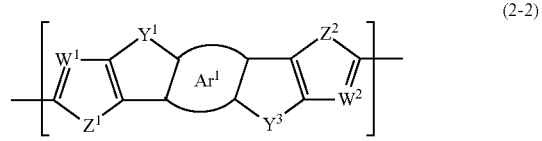

(2-2)

The nitrogen-containing condensed ring compound of the present embodiment includes: a monomer having only one structural unit represented by the formula (1-1) or the formula (1-2); and a nitrogen-containing condensed ring polymer containing a plurality of such structural units, as described later. Of these, the nitrogen-containing condensed ring compound as a monomer will be explained herein. An example of the nitrogen-containing condensed ring compound as a monomer is a compound having predetermined groups at both ends of the structural unit represented by the formula (1-1) or the formula (1-2). Specific examples include compounds represented by the following formulae (6-1) and (6-2):

[Chemical Formula 12]

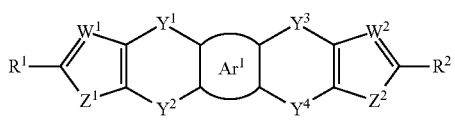

(6-1)

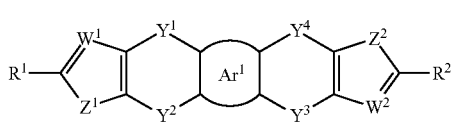

(6-2)

In the formulae (6-1) and (6-2), $Ar^1$, $Y^1$, $Y^2$, $Y^3$, $Y^4$, $W^1$, $W^2$, $Z^1$ and $Z^2$ are the same as those in the case of the above described groups having the same symbols. $R^1$ and $R^2$ at the ends each independently represent a hydrogen atom, a halogen atom, or a monovalent group.

Examples of the monovalent groups represented by $R^1$ and $R^2$ are the same as those of the monovalent groups represented by $R^3$, $R^4$, $R^5$, and $R^6$. This monovalent group may optionally have a substituent. Examples of such a substituent are also the same as those in the case of the monovalent groups represented by $R^3$, $R^4$, $R^5$, and $R^6$.

The monovalent groups represented by $R^1$ and $R^2$ may be cyclic groups, for example, a cyclic group in which the number of atoms constituting the ring is 3 to 60. Examples of such a cyclic group in which the number of atoms constituting the ring is 3 to 60 include groups represented by the following formulae:

[Chemical Formula 13]

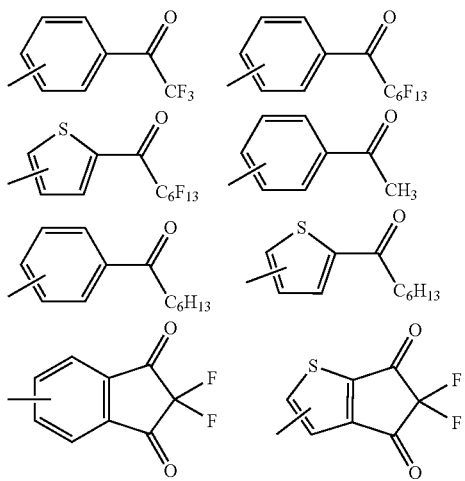

The monovalent groups represented by $R^1$ and $R^2$ can be selected, depending on the properties of the nitrogen-containing condensed ring compound to be improved. For example, as such monovalent groups, linear or branched acyclic groups are preferable, a linear or branched alkyl group and a linear or branched alkoxy group are more preferable, and a linear or branched alkyl group is further preferable. Using these monovalent groups, the solubility of the nitrogen-containing condensed ring compound in an organic solvent tends to be further improved. Examples of such alkyl groups or alkoxy groups are the same as those of the alkyl groups or alkoxy groups used as monovalent groups represented by $R^3$, $R^4$, $R^5$, and $R^6$.

In addition, as such monovalent groups represented by $R^1$ and $R^2$, a group having a fluorine atom or a group having a carbonyl group is preferable, and a group having a fluorine atom and a carbonyl group is more preferable. When $R^1$ and $R^2$ are such groups, the LUMO level of the nitrogen-containing condensed ring compound is further decreased, and the solubility in an organic solvent is further improved.

Moreover, at least one of $R^1$ and $R^2$ is preferably a fluoroalkyl group, a fluoroalkoxy group, a fluoroaryl group, a group having an α-fluorocarbonyl structure (a structure represented by —C(=O)—CF>), an aryl group in which at least one hydrogen atom is substituted with a fluoroalkyl group, an aryl group in which at least one hydrogen atom is substituted with a fluoroalkoxy group, an aryl group in which at least one hydrogen atom is substituted with a group having an α-fluorocarbonyl structure, an aryl group which is condensed with a cyclic structure having an α-fluorocarbonyl structure, a heterocyclic group in which at least one hydrogen atom is substituted with a fluoroalkyl group, a heterocyclic group in which at least one hydrogen atom is substituted with a fluoroalkoxy group, a heterocyclic group in which at least one hydrogen atom is substituted with a group having an α-fluorocarbonyl structure, or a heterocyclic group which is condensed with a cyclic structure having an α-fluorocarbonyl structure. Thereby, it becomes possible to further enhance the electron transport property of the nitrogen-containing condensed ring compound.

Examples of the fluoroalkyl group, fluoroalkoxy group, and fluoroaryl group used herein include the alkyl group, alkoxy group, and aryl group used as the above described monovalent groups represented by $R^3$, $R^4$, $R^5$ and $R^6$, in which at least one hydrogen atom is substituted with a fluorine atom. An example of the group having an α-fluorocarbonyl structure is a group having a structure represented by the following formula (f). In addition, examples of the aryl groups in the above described groups are the same as those of the aryl groups used as the monovalent groups represented by $R^3$, $R^4$, $R^5$ and $R^6$. Moreover, an example of the above-mentioned heterocyclic group is a heterocyclic group consisting of the remaining atomic group obtained by removing one hydrogen atom from a heterocyclic compound. Specific examples of this heterocyclic compound include: thiophene; compounds formed by condensation of 2 to 6 thiophene rings, such as thienothiophene or dithienothiophene; benzothiophene; benzodithiophene; dibenzothiophene; cyclopentadithiophene; thiazole; thiazolothiazole; pyrrole; pyridine; and pyrimidine.

[Chemical Formula 14]

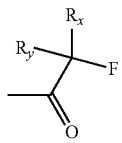
(f)

wherein, in the formula (f), $R_x$ and $R_y$ each independently represent a halogen atom or an alkyl group containing 1 to 20 carbon atoms.

Each of $R^1$ and $R^2$ is more preferably a fluoroalkyl group, a fluoroalkoxy group, a fluoroaryl group, a group having an α-fluorocarbonyl structure, an aryl group in which at least one hydrogen atom is substituted with a fluoroalkyl group, an aryl group in which at least one hydrogen atom is substituted with a fluoroalkoxy group, a heterocyclic group in which at least one hydrogen atom is substituted with a fluoroalkyl group, a heterocyclic group in which at least one hydrogen atom is substituted with a fluoroalkoxy group, a heterocyclic group in which at least one hydrogen atom is substituted with a group having an α-fluorocarbonyl structure, or a heterocyclic group which is condensed with a cyclic structure having an α-fluorocarbonyl structure.

Each of $R^1$ and $R^2$ is particularly preferably a heterocyclic group in which at least one hydrogen atom is substituted with a fluoroalkyl group, a heterocyclic group in which at least one hydrogen atom is substituted with a fluoroalkoxy group, a heterocyclic group in which at least one hydrogen atom is substituted with a group having an α-fluorocarbonyl structure, or a heterocyclic group which is condensed with a cyclic structure having an α-fluorocarbonyl structure. When both $R^1$ and $R^2$ are the above described groups, the electron transport property of the nitrogen-containing condensed ring compound can be further improved.

Moreover, the monovalent groups represented by $R^1$ and $R^2$ may be polymerizable groups. The nitrogen-containing condensed ring compound having such a polymerizable group can be used as a raw material compound to synthesize a nitrogen-containing condensed ring polymer as described later (which can also be referred to as a precursor of a nitrogen-containing condensed ring polymer). When the nitrogen-containing condensed ring compound is used as a raw material compound to synthesize a nitrogen-containing condensed ring polymer, both $R^1$ and $R^2$ are preferably polymerizable groups.

Examples of such a polymerizable group include a halogen atom, an alkyl sulfonate group, an aryl sulfonate group, an arylalkyl sulfonate group, an alkyl stannyl group in which 1 to 3 alkyl groups bind to a tin atom, an aryl stannyl group in which 1 to 3 aryl groups bind to a tin atom, an arylalkyl stannyl group in which 1 to 3 arylalkyl groups bind to a tin atom, a borate ester residue, a sulfonium methyl group, a phosphonium methyl group, a phosphonate methyl group, a monohalogenated methyl group, a boric acid residue (a group represented by —B(OH)$_2$), a formyl group, and a vinyl group. Among others, preferred examples of a polymerizable group include a halogen atom, an alkyl stannyl group, and a borate ester residue. When the nitrogen-containing condensed ring compound has such a polymerizable group, it becomes easier to synthesize a nitrogen-containing condensed ring polymer. Examples of the borate ester residue include groups represented by the following formulae:

[Chemical Formula 15]

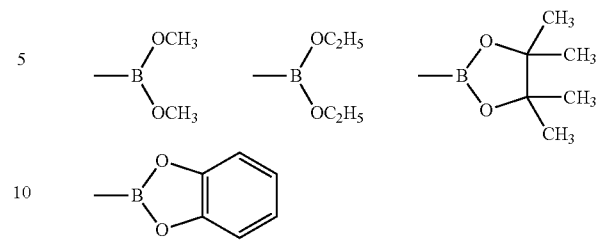

Furthermore, $R^1$ and $R^2$ may also be protecting groups capable of being induced to any one of the above described groups. Herein, the protecting group means a group that is inactive to at least one reaction. Examples of such a protecting group include groups having active hydrogen, in which the active hydrogen is substituted with a trimethylsilyl group (TMS), a triethylsilyl group (TES), a tert-butyldimethylsilyl group (TBS or TBDMS), a triisopropylsilyl group (TIPS), a tert-butyldiphenylsilyl group (TBDPS) or the like. Examples of such a group having active hydrogen include a hydroxyl group, an amino group, an alkyl amino group, an acyl amino group (IUPAC name: alkanoyl amino group), and a sulfo group.

When an organic thin film contains a nitrogen-containing condensed ring compound, if $R^1$ and/or $R^2$ in the nitrogen-containing condensed ring compound are/is polymerizable group(s), the properties or durability of the organic thin film may be decreased upon being used in production of an organic thin film element. In such a case, the polymerizable group(s) may be optionally substituted with inactive group(s).

Examples of the nitrogen-containing condensed ring compound include nitrogen-containing aromatic ring compounds each having a structural unit represented by the following formula (2-3), (2-4), (2-5), (2-6), (2-7), or (2-8), as well as the above described nitrogen-containing condensed ring compounds each having the structural unit represented by the formula (2-1) or (2-2). The groups indicated with individual symbols in the following formulae have the same definitions as those of the groups indicated with the same symbols in the above-mentioned formulae.

[Chemical Formula 16]

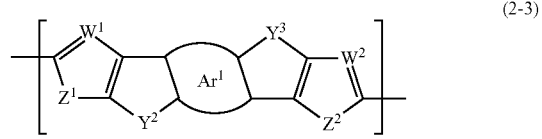
(2-3)

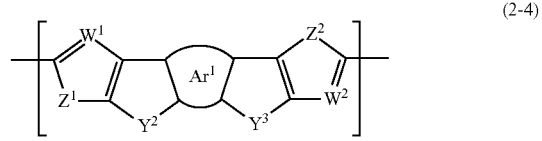
(2-4)

[Chemical Formula 17]

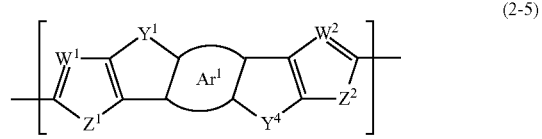
(2-5)

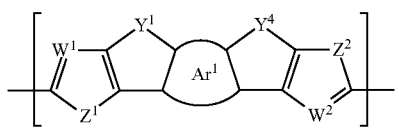

(2-6)

[Chemical Formula 18]

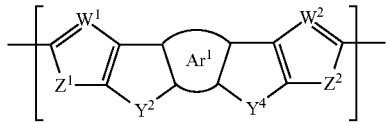

(2-7)

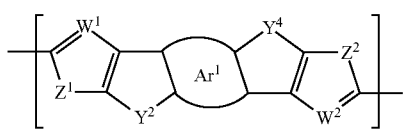

(2-8)

Among these structural units, the structural unit represented by the formula (2-1) or (2-2) is more preferable. That is to say, the nitrogen-containing condensed ring compound preferably has the structural unit represented by the formula (2-1) or the structural unit represented by the formula (2-2). In the nitrogen-containing condensed ring compound having such a structural unit, π-conjugated planarity between the rings is further favorable, and a much lower LUMO level can be achieved, so that the compound can be used as an organic n-type semiconductor that is further excellent in terms of an electron transport property. Also, since such a nitrogen-containing condensed ring compound is further excellent in terms of solubility in an organic solvent, it becomes possible to produce an organic thin film element with more excellent performance by forming an organic thin film using such a nitrogen-containing condensed ring compound. Furthermore, since such a nitrogen-containing condensed ring compound is chemically stable and is more excellent in terms of environmental stability, it becomes possible to produce an organic thin film element with more stable performance in an ordinary atmosphere by forming an organic thin film using such a nitrogen-containing condensed ring compound.

An example of the nitrogen-containing condensed ring compound having the structural unit represented by the formula (2-1) or the structural unit represented by the formula (2-2) is a compound represented by the following formula (7-1) or formula (7-2). In the formulae (7-1) and (7-2), $Ar^1$, $W^1$, $W^2$, $Y^1$, $Y^3$, $Z^1$ and $Z^2$ have the same definitions as those of the groups indicated with the same symbols as mentioned above in the formulae (2-1) and (2-2), and $R^1$ and $R^2$ in the formulae (7-1) and (7-2) have the same definitions as those of $R^1$ and $R^2$ in the formulae (6-1) and (6-1).

[Chemical Formula 19]

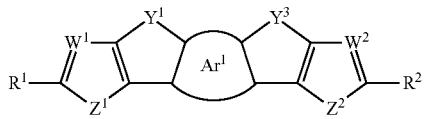

(7-1)

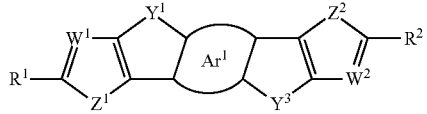

(7-2)

Further, as such a nitrogen-containing condensed ring compound, a nitrogen-containing condensed ring compound having a structural unit represented by the following formula (3-01) or a structural unit represented by the following formula (3-02) is preferable, and a nitrogen-containing condensed ring compound having a structural unit represented by the following formula (3-1) or a structural unit represented by the following formula (3-2) is more preferable. Such a nitrogen-containing condensed ring compound provides the above described advantageous effects of the present invention more favorably.

[Chemical Formula 20]

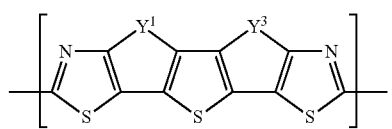

(3-01)

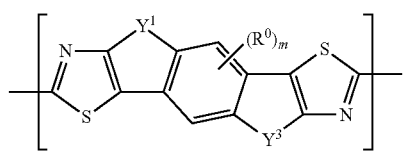

(3-02)

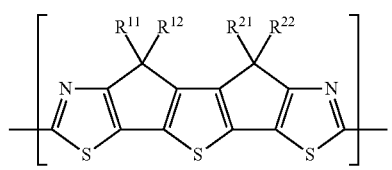

(3-1)

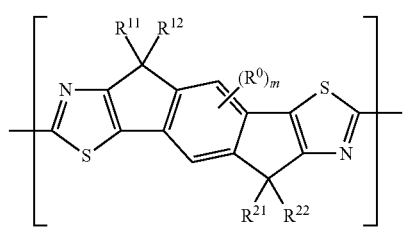

(3-2)

$Y^1$ and $Y^3$ in the formula (3-01) and the formula (3-02) have the same definitions as those of the groups indicated with the same symbols as mentioned above.

$R^{11}$, $R^{12}$, $R^{21}$ and $R^{22}$ in the formula (3-1) and the formula (3-2) have the same definitions as those of the groups indicated with the same symbols as mentioned above.

In the formula (3-02) and the formula (3-2), $R^0$ represents a substituent, and m represents an integer of 0 to 2. Examples of the substituent represented by $R^0$ are the same as those optionally possessed by the above-mentioned aromatic ring represented by $Ar^1$. Specifically, as such a substituent, a substituent constituted with 20 or less atoms is preferable, and a substituent constituted with 17 or less atoms is more preferable. Specific examples of such a substituent include: alkyl groups such as a methyl group, an ethyl group, or a propyl group; alkoxy groups such as a methoxy group, an ethoxy group, or a propoxy group; aryl groups such as a phenyl group or a naphthyl group; halogen atoms such as a fluorine atom, a chlorine atom, or a bromine atom; nitro groups; and cyano groups. Among these groups, $R^0$ is preferably an alkyl group, an alkoxy group or an aryl group, and is more preferably an alkyl group. When m is 2, a plurality of $R^0$ may be identical to or different from each other.

Examples of such a nitrogen-containing condensed ring compound include compounds represented by the following formulae (8-1), (8-2), (8-3), (8-4), (8-5), (8-6), (8-7), (8-8), (8-9), (8-10), (8-11), (8-12), (8-13), (8-14), (8-15), and (8-16). In these formulae, $R^{11}$, $R^{12}$, $R^{21}$, $R^{22}$, $R^0$ and m have the same definitions as those described above.

[Chemical Formula 21]

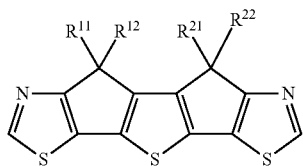

(8-1)

[Chemical Formula 22]

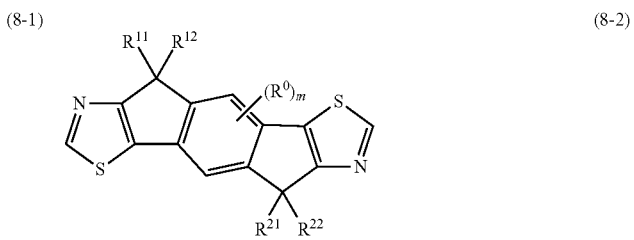

(8-2)

[Chemical Formula 23]

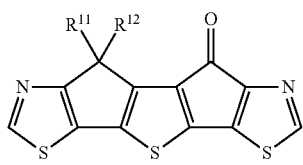

(8-3)

[Chemical Formula 24]

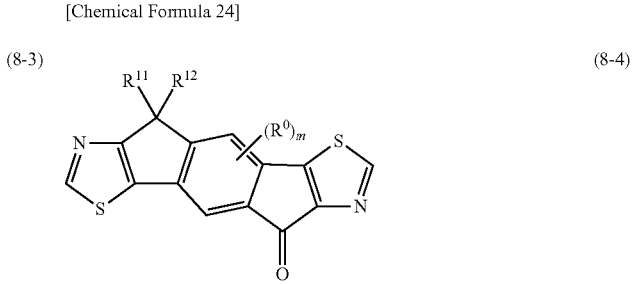

(8-4)

[Chemical Formula 25]

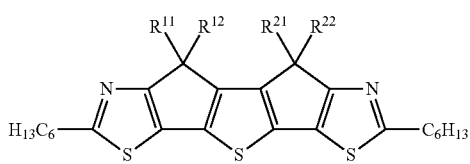

(8-5)

[Chemical Formula 26]

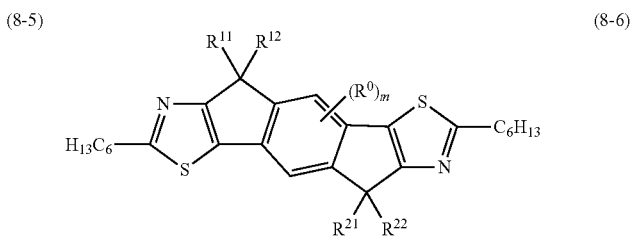

(8-6)

[Chemical Formula 27]

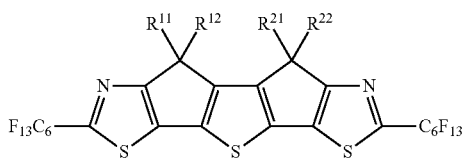

(8-7)

[Chemical Formula 28]

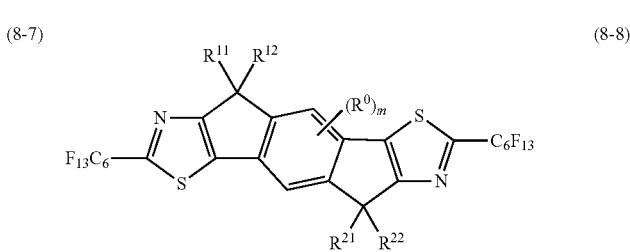

(8-8)

[Chemical Formula 29]

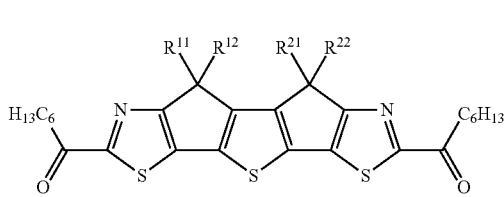

(8-9)

[Chemical Formula 30]

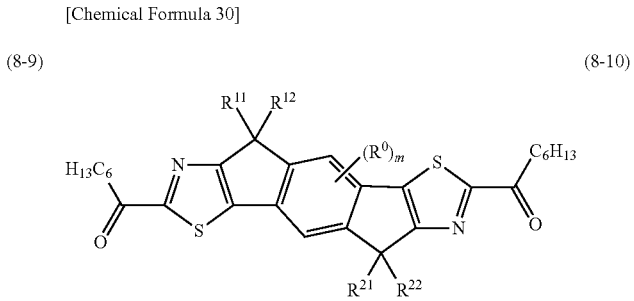

(8-10)

-continued

[Chemical Formula 31]

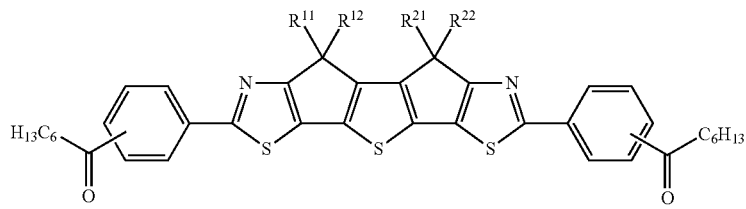

(8-11)

[Chemical Formula 32]

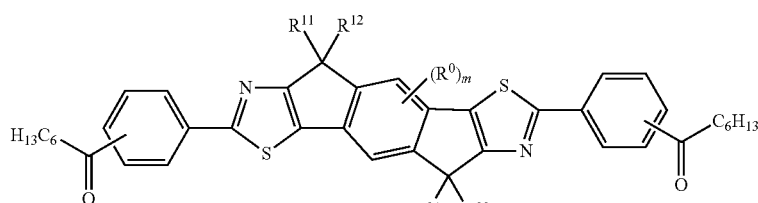

(8-12)

[Chemical Formula 33]

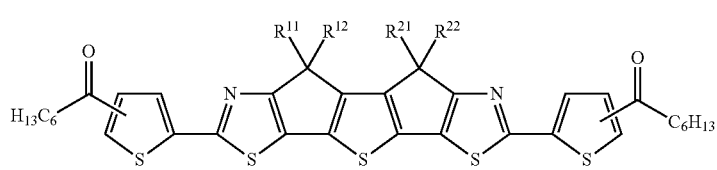

(8-13)

[Chemical Formula 34]

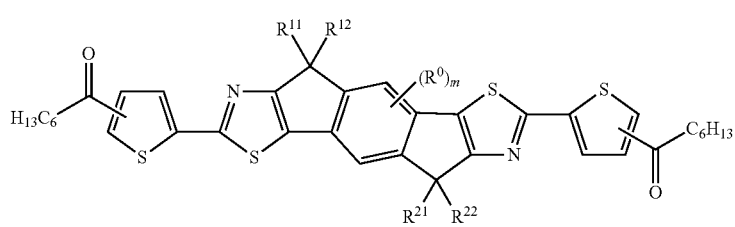

(8-14)

[Chemical Formula 35]

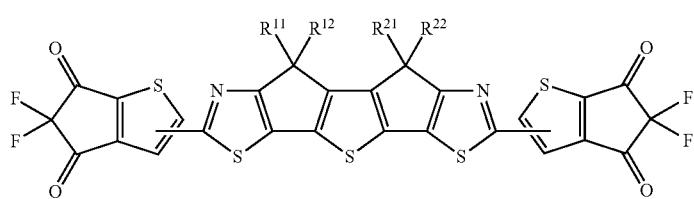

(8-15)

[Chemical Formula 36]

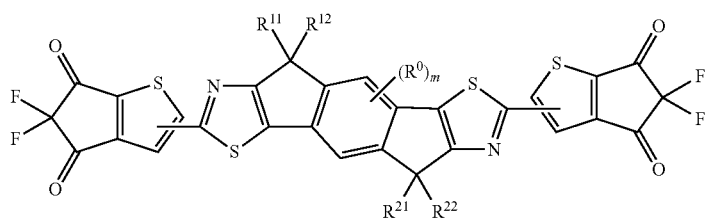

(8-16)

[Nitrogen-Containing Condensed Ring Polymer]

Next, a nitrogen-containing condensed ring polymer according to a preferred embodiment will be described.

The nitrogen-containing condensed ring polymer of the present embodiment has a plurality of the structural units represented by the formula (1-1) (hereinafter also referred to as a "first structural unit" at times), or has a plurality of the structural units represented by the formula (1-2) (hereinafter also referred to as a "second structural unit" at times), or has at least one first structural unit and at least one second structural unit. Examples of the structural units represented by the formulae (1-1) and (1-2) in the nitrogen-containing condensed ring polymer are the same as those of the structural units represented by the formulae (1-1) and (1-2) in the above described nitrogen-containing condensed ring compound (monomer). Also, preferred structures of these structural units are the same as those described above.

The nitrogen-containing condensed ring polymer has a plurality of structural units selected from at least one of the first structural unit and the second structural unit, or has a combination of the first structural unit(s) and the second structural unit(s). The term "structural unit" of the nitrogen-containing condensed ring polymer is used herein to mean a structural unit that constitutes at least a part of the main chain of the nitrogen-containing condensed ring polymer. In addition, the term "polymer" is used herein to mean a compound having at least two such "structural units," and it includes all compounds generally classified into an oligomer or a polymer.

The total content of the first structural unit and the second structural unit in the nitrogen-containing condensed ring polymer is preferably 20% by mass or more, more preferably 35% by mass to 98% by mass, and further preferably 50% by mass to 95% by mass, based on the total mass of the nitrogen-containing condensed ring polymer.

The first structural unit is preferably the structural unit represented by the above formula (2-1). In addition, the second structural unit is preferably the structural unit represented by the above formula (2-2).

It is preferable that the nitrogen-containing condensed ring polymer of the present embodiment further have a structural unit represented by the following formula (4) (hereinafter also referred to as a "third structural unit" at times), in addition to the first structural unit and the second structural unit. By having the third structural unit in combination with the first and second structural units, it becomes possible to vary the solubility of the nitrogen-containing condensed ring polymer and the mechanical, thermal or electronic properties thereof in a wide range, and thus, desired properties can be easily obtained. When the nitrogen-containing condensed ring polymer contains a plurality of third structural units, the plurality of the third structural units in the molecule may be identical to or different from each other.

[Chemical Formula 37]

$$-\!\!\!+\!\mathrm{Ar}^2\!\!+\!\!\!- \qquad (4)$$

In the formula (4), $\mathrm{Ar}^2$ represents an aromatic hydrocarbon group optionally having a substituent, a heterocyclic group optionally having a substituent, a group represented by $-CR_a=CR_b-$, or a group represented by $-C\equiv C-$. $R_a$ and $R_b$ each independently represent a hydrogen atom, a halogen atom, an alkyl group containing 1 to 20 carbon atoms and optionally having a substituent, an aryl group containing 6 to 60 carbon atoms and optionally having a substituent, a heterocyclic group containing 4 to 60 carbon atoms and optionally having a substituent, or a cyano group. Examples of the substituent optionally possessed by the alkyl group containing 1 to 20 carbon atoms represented by $R_a$ or $R_b$ include an alkoxy group containing 1 to 20 carbon atoms, an aryl group containing 6 to 20 carbon atoms, a halogen atom, a nitro group, and a cyano group. In addition, examples of the substituent optionally possessed by the aryl group containing 6 to 60 carbon atoms or the heterocyclic group containing 4 to 60 carbon atoms, represented by $R_a$ or $R_b$, include an alkyl group containing 1 to 20 carbon atoms, an alkoxy group containing 1 to 20 carbon atoms, an aryl group containing 6 to 20 carbon atoms, a halogen atom, a nitro group, and a cyano group. Moreover, examples of the heterocyclic group containing 4 to 60 carbon atoms represented by $R_a$ or $R_b$ include a pyridyl group, a thienyl group, a thienothienyl group, a dithienothienyl group, a benzothienyl group, a benzodithiophenyl group, a dibenzothienyl group, a pyrrolyl group, a quinolyl group, and an indolyl group.

Herein, the aromatic hydrocarbon group represented by $\mathrm{Ar}^2$ is a divalent aromatic hydrocarbon group. The divalent aromatic hydrocarbon group means a group that consists of the remaining atomic group obtained by removing two hydrogen atoms from benzene or a condensed ring compound in which two or more rings are condensed. Examples of such a condensed ring compound include naphthalene, anthracene, tetracene, pentacene, pyrene, perylene, and fluorene.

As such an aromatic hydrocarbon group represented by $\mathrm{Ar}^2$, a group in which the number of carbon atoms constituting the ring is 6 to 60 is preferable, and a group in which the number of carbon atoms constituting the ring is 6 to 20 is more preferable. As such an aromatic hydrocarbon group represented by $\mathrm{Ar}^2$, a group consisting of the remaining atomic group obtained by removing two hydrogen atoms from benzene, pentacene, pyrene or fluorine is preferable.

The aromatic hydrocarbon group represented by $\mathrm{Ar}^2$ may optionally have a substituent. Examples of such a substituent include a halogen atom, a saturated or unsaturated hydrocarbon group, an aryl group, an alkoxy group, an aryloxy group, a monovalent heterocyclic group, an amino group, a nitro group, and a cyano group. Examples of the saturated hydrocarbon group serving as such a substituent are the same as those of the alkyl group used as the above described monovalent group containing an alkane skeleton. Examples of the unsaturated hydrocarbon group include a vinyl group, a 1-propenyl group, an allyl group, a propargyl group, an isopropenyl group, a 1-butenyl group, and a 2-butenyl group; and among these groups, a vinyl group is preferable. Examples of the aryl group and the alkoxy group are the same as those of the above described monovalent groups represented by $R^3$ to $R^6$; and examples of the aryloxy group include oxy groups (—O—) to which the same aryl groups as described above bind. Moreover, an example of the monovalent heterocyclic group is a heterocyclic group consisting of the remaining atomic group obtained by removing one hydrogen atom from a heterocyclic compound. Specific examples of this heterocyclic compound include: thiophene; compounds formed by condensation of 2 to 6 thiophene rings, such as thienothiophene or dithienothiophene; benzothiophene; benzodithiophene; dibenzothiophene; cyclopentadithiophene; thiazole; thiazolothiazole; pyrrole; pyridine; and pyrimidine.

The heterocyclic group represented by $\mathrm{Ar}^2$ is a divalent heterocyclic group. The divalent heterocyclic group means the remaining atomic group obtained by removing two hydrogen atoms from a heterocyclic compound. It is to be noted that, in the present specification, the heterocyclic compound means an organic compound having a cyclic structure, which has, as an atom constituting the ring, a heteroatom such as an oxygen atom, a sulfur atom, a nitrogen atom, a phosphorus atom, a boron atom or a silicon atom. Specific examples of the heterocyclic compound include: thiophene; compounds formed by condensation of 2 to 6 thiophene rings, such as thienothiophene or dithienothiophene; benzothiophene; benzodithiophene; dibenzothiophene; cyclopentadithiophene; thiazole; thiazolothiazole; pyrrole; pyridine; and pyrimidine.

As such a heterocyclic group represented by $\mathrm{Ar}^2$, a group in which the number of carbon atoms constituting the ring is 3 to 60 is preferable, and a group in which the number of carbon atoms constituting the ring is 3 to 20 is more preferable. In addition, preferred examples of the heterocyclic group represented by $Ar^2$ include: compounds formed by condensation of 2 to 6 thiophene rings, such as thiophene or thienothiophene; and a group consisting of the remaining atomic group obtained by removing two hydrogen atoms from benzothiophene, benzodithiophene, dibenzothiophene, cyclopentadithiophene or thiazole.

The heterocyclic group represented by $Ar^2$ may optionally have a substituent. Examples of such a substituent include a halogen atom, a saturated or unsaturated hydrocarbon group, an aryl group, an alkoxy group, an aryloxy group, a monovalent heterocyclic group, an amino group, a nitro group, and a cyano group. Examples of such a substituent are the same as those optionally possessed by the above described aromatic hydrocarbon group.

It is preferable that the nitrogen-containing condensed ring polymer of the present embodiment have a structure in which one of the first structural unit and the second structural unit is positioned adjacent to the third structural unit. Since a dihedral angle between the aromatic rings or heterocyclic rings adjacent to each other can be reduced if the present nitrogen-containing condensed ring polymer has the aforementioned structure, planarity in the molecule is improved, the degree of π-conjugation in the molecule becomes great, and also, the LUMO level is decreased, and as a result, the electron transport property is further improved. Herein, the dihedral angle is defined as an angle of 0 to 90 degrees, which is made between a plane containing the heterocyclic ring in the first structural unit or the second structural unit and a plane containing the group represented by $Ar^2$ in the third structural unit. When one of the first structural unit and the second structural unit is adjacent to the third structural unit, the dihedral angle is generally 0 to 45 degrees, preferably 0 to 40 degrees, and more preferably 0 to 30 degrees.

The third structural unit is preferably a structural unit represented by the following formula (5):

[Chemical Formula 38]

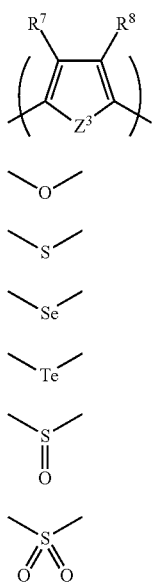

In the above formula (5), $R^7$ and $R^8$ each independently represent a hydrogen atom, a halogen atom, or a monovalent group optionally having a substituent, and $Z^3$ represents any one of the groups represented by the formulae (xi) to (xix). $R^7$ and $R^8$ may bind to each other to form a ring together with carbon atoms to which they bind. It is to be noted that the groups represented by the formulae (xvii) and (xviii) have two binding modes, in which the groups are horizontally flipped, and that both of the two binding modes may be adopted. Examples of the monovalent group mentioned herein are the same as those of the above described monovalent group represented by $R^3$ or the like.

$Z^3$ is preferably a group represented by any one of the formulae (xi), (xii), (xiii), (xvii), (xviii) and (xix), more preferably a group represented by any one of the formulae (xii), (xiii), (xvii) and (xix), and further preferably a group represented the formula (xii). When $Z^3$ is such a preferred group, the nitrogen-containing condensed ring polymer exhibits characteristic electrical properties (for example, highest occupied molecular orbital (HOMO) and LUMO, which are suitable for electron transport), and various electrical characteristics (for example, a much higher electron transport property) tend to be easily exhibited.

When the nitrogen-containing condensed ring polymer contains the third structural unit, the ratio $C_3/C_{1+2}$ between the total content of the first structural unit and the second structural unit $C_{1+2}$ (mole) and the content of the third structural unit $C_3$ (mole) in the nitrogen-containing condensed ring polymer is preferably 0.05 to 3, more preferably 0.2 to 2, and further preferably 0.5 to 1.

The nitrogen-containing condensed ring polymer according to the present embodiment is preferably a nitrogen-containing condensed ring polymer represented by the following formula (9-1), (9-2), (9-3) or (9-4) because a much higher electron transport property can be obtained.

[Chemical Formula 39]

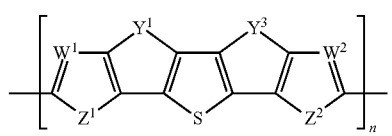

[Chemical Formula 40]

(9-2)

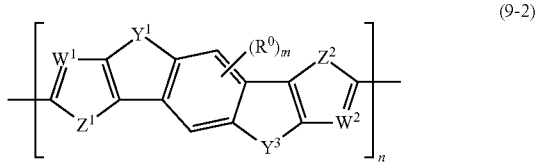

[Chemical Formula 41]

(9-3)

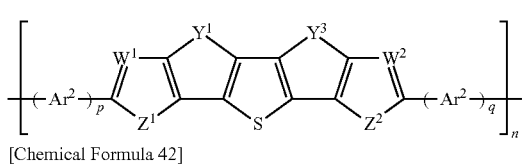

[Chemical Formula 42]

(9-4)

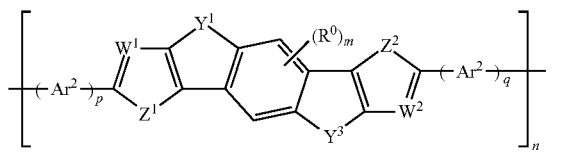

In the formulae (9-1) to (9-4), $W^1$, $W^2$, $Y^1$, $Y^3$, $Z^1$ and $Z^2$ have the same definitions as those of $W^1$, $W^2$, $Y^1$, $Y^3$, $Z^1$ and $Z^2$ in the formulae (1-1) and (1-2), respectively; m and $R^0$ have the same definitions as those of m and $R^0$ in the formula (8-2) and the like, respectively; and $Ar^2$ has the same definitions as those of $Ar^2$ in the formula (4). In addition, p and q each independently represent an integer of 0 to 6 (wherein at least one of p and q represents an integer of 1 to 6), and p+q represents an integer of 1 to 6, and preferably an integer of 1 to 3. Moreover, n represents an integer of 2 to 500, preferably an integer of 2 to 100, and more preferably an integer of 2 to 20.

In the polymer represented by the formula (9-1), (9-2), (9-3) or (9-4), both $W^1$ and $W^2$ are preferably —N═. $Y^1$ and $Y^3$ each independently represent a group represented by —C($R^{11}$)($R^{12}$)— or a group represented by —C($R^{21}$)($R^{22}$)—, wherein it is preferable that $R^{11}$, $R^{12}$, $R^{21}$ and $R^{22}$ each represent a monovalent group containing an alkane skeleton. Furthermore, $Ar^2$ is preferably a group represented by the formula (5).

At both ends of the structure containing the first to third structural units, the nitrogen-containing condensed ring polymer of the present embodiment may optionally have the same groups as those represented by $R^1$ and $R^2$ in the above formula (6-1) and (6-2), for example.

Examples of a group present in the terminal portion of the nitrogen-containing condensed ring polymer (hereinafter referred to as a "terminal group") include a hydrogen atom, a fluorine atom, an alkyl group, an alkoxy group, an acyl group, an amino-keto group, an aryl group, a heterocyclic group, a group having an α-fluorocarbonyl structure, an electron-donating group, and an electron-withdrawing group; and the hydrogen atom in these groups may be optionally substituted with a fluorine atom. Examples of the alkyl group, a group containing the alkyl group in the structure thereof (an alkoxy group or an acyl group), the aryl group, and the group having an α-fluorocarbonyl structure, each of which serves as a terminal group, are the same as those serving as the above described monovalent groups represented by $R^1$ and $R^2$. Examples of the heterocyclic group are the same as the above described heterocyclic groups optionally possessed as substituents by $Ar^2$. Examples of the electron-donating group include an alkylthio group containing 1 to 20 carbon atoms, an amino group, and an amino group substituted with an alkyl group containing 1 to 20 carbon atoms. Examples of the electron-withdrawing group are the same as the above described electron-withdrawing groups for the monovalent group represented by A. Among them, groups in which all of hydrogen atoms are substituted with fluorine atoms, such as a perfluoroalkyl group, a perfluoroalkoxy group and a perfluorophenyl group, are preferable. In addition, a group having a conjugated bond consecutive to the conjugated structure of the main chain is also preferable. Examples of such a group include an aryl group and a heterocyclic group, which are connected with the conjugated structure of the main chain via a carbon-carbon bond.

Moreover, the terminal group may be a polymerizable group. Such a nitrogen-containing condensed ring polymer can also be used as a raw material compound to synthesize another nitrogen-containing condensed ring polymer with a higher molecular weight. When the nitrogen-containing condensed ring polymer is used as such a raw material compound, it is preferable that the terminal groups at both ends of the nitrogen-containing condensed ring polymer be both polymerizable groups. Examples of such a polymerizable group are the same as those described above.

However, when an organic thin film contains the nitrogen-containing condensed ring polymer, if the terminal groups are polymerizable groups, the properties and durability of an organic thin film element are likely to be reduced after the organic thin film has been used to produce the element. In such a case, the polymerizable groups may be protected by inactive groups.

Particularly preferred examples of the present nitrogen-containing condensed ring polymer include polymers represented by the following formulae (10-1), (10-2), (10-3), (10-4), (10-5), (10-6), (10-7), (10-8), (10-9), (10-10), (10-11), (10-12), (10-13), (10-14), (10-15), (10-16), (10-17), (10-18), (10-19), and (10-20):

[Chemical Formula 43]

(10-1)

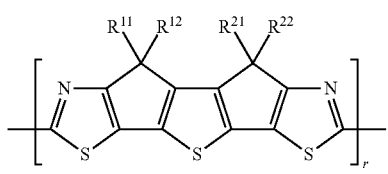

[Chemical Formula 44]

(10-2)

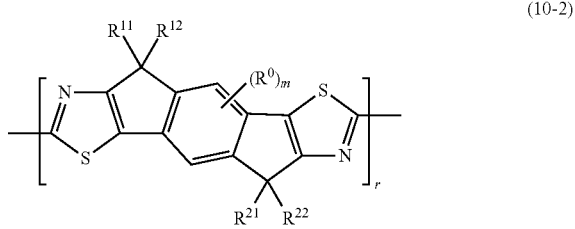

[Chemical Formula 45]
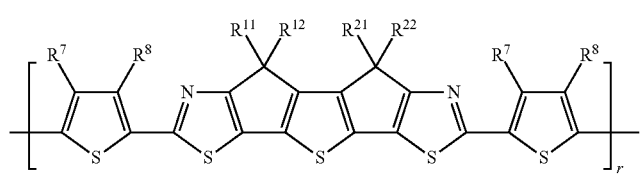
(10-3)
[Chemical Formula 46]
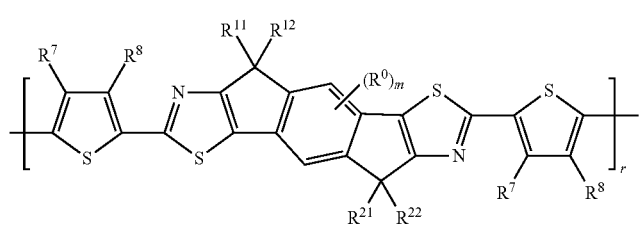
(10-4)
[Chemical Formula 47]
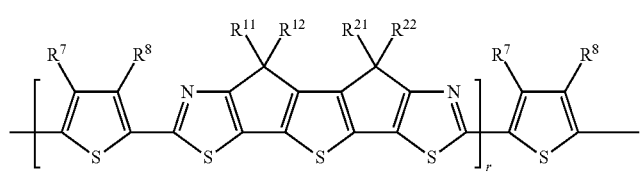
(10-5)
[Chemical Formula 48]
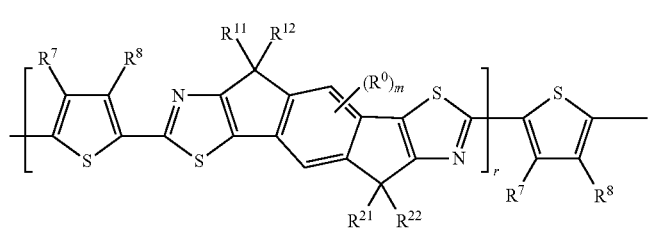
(10-6)
[Chemical Formula 49]
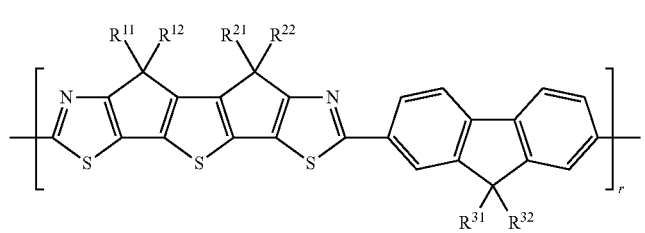
(10-7)
[Chemical Formula 50]
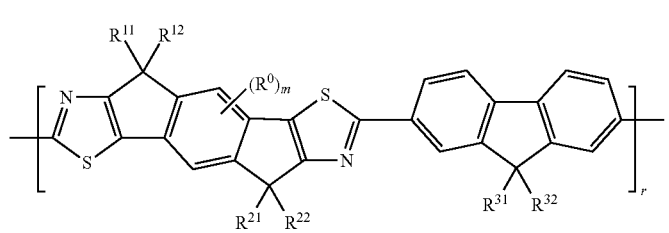
(10-8)

-continued
[Chemical Formula 51]
(10-9)
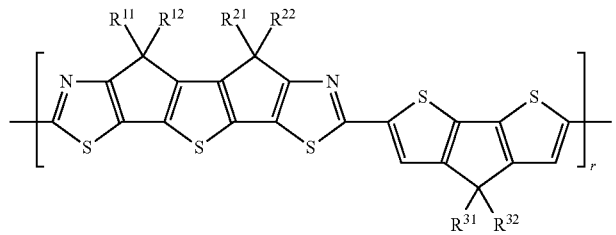
[Chemical Formula 52]
(10-10)
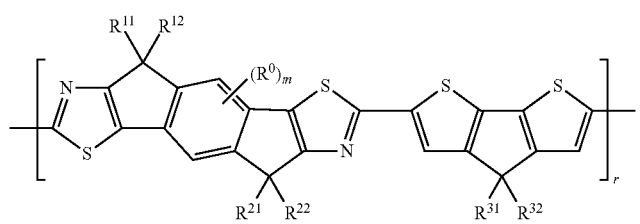
[Chemical Formula 53]
(10-11)
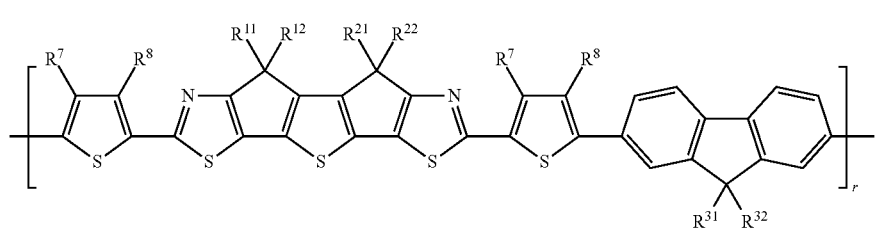
[Chemical Formula 54]
(10-12)
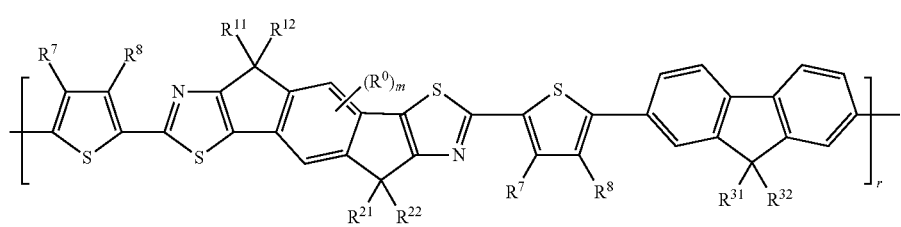
[Chemical Formula 55]
(10-13)
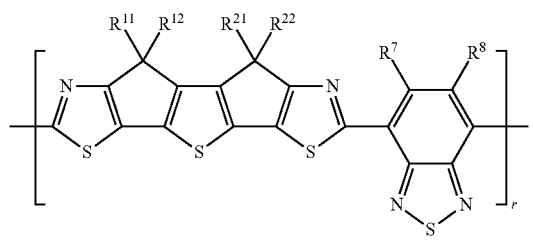
[Chemical Formula 56]
(10-14)
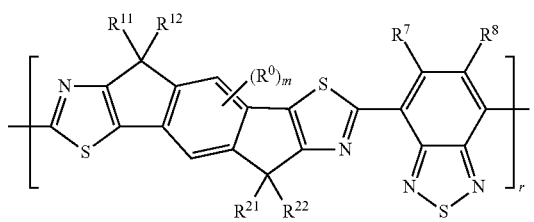
[Chemical Formula 57]
(10-15)
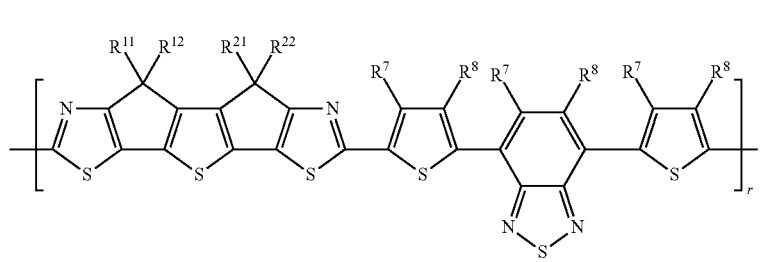

[Chemical Formula 58]

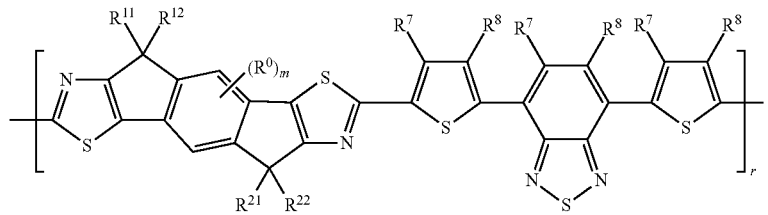

(10-16)

[Chemical Formula 59]

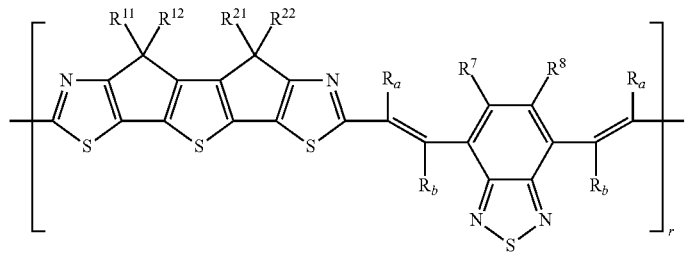

(10-17)

[Chemical Formula 60]

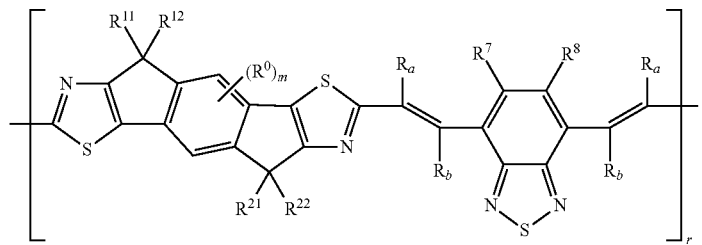

(10-18)

[Chemical Formula 61]

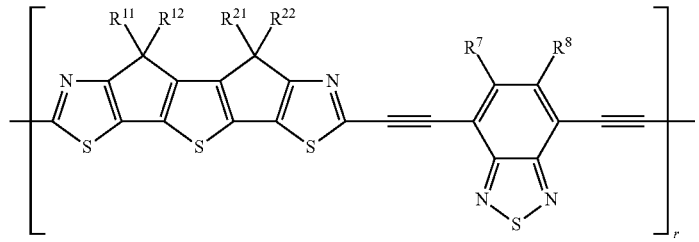

(10-19)

[Chemical Formula 62]

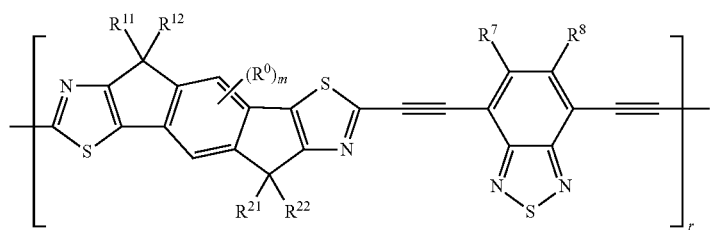

(10-20)

In the formulae (10-1) to (10-20), $R^{11}$, $R^{12}$, $R^{21}$ and $R^{22}$ have the same definitions as those of $R^{11}$, $R^{12}$, $R^{21}$ and $R^{22}$ in the formula (1-1) and the formula (1-2), respectively; $R^0$ and m have the same definitions as those of $R^0$ and m in the formula (8-2) and the like, respectively; $R^7$ and $R^8$ have the same definitions as those of $R^7$ and $R^8$ in the formula (5), respectively; and r represents an integer of 2 or greater.

In addition, in the formulae (10-7), (10-8), (10-9), (10-10), (10-11), and (10-12), $R^{31}$ and $R^{32}$ each independently represent a hydrogen atom or any given substituent. Herein, as such any given substituent, a substituent constituted with 20 or less atoms is preferable, and a substituent constituted with 17 or less atoms is more preferable. Specific examples of such a substituent include: alkyl groups such as a methyl group, an ethyl group, or a propyl group; alkoxy groups such as a methoxy group, an ethoxy group, or a propoxy group; aryl groups such as a phenyl group or a naphthyl group; halogen atoms such as a fluorine atom, a chlorine atom, or a bromine atom; nitro groups; and cyano groups. Among these groups, alkyl groups, alkoxy groups or aryl groups are preferable, and alkyl groups are more preferable.

When a plurality of $R^0$, $R^7$, $R^8$, $R^{31}$ or $R^{32}$ are present in the nitrogen-containing condensed ring polymer, the groups with the same symbols may be identical to or different from each other. If the groups with the same symbols are identical to one another, it facilitates production of the nitrogen-containing condensed ring polymer, and therefore, it is more preferable.

When the nitrogen-containing condensed ring polymer is used to produce an organic thin film, r in the formulae (10-1) to (10-20) can be selected depending on a method for producing the organic thin film. For example, if the nitrogen-containing condensed ring polymer has sublimability, an organic thin film containing the nitrogen-containing condensed ring polymer can be produced according to a vapor-phase growth method such as a vacuum evaporation method. In this case, r is preferably an integer of 2 to 10, and more preferably an integer of 2 to 5.

On the other hand, when a method for producing an organic thin film, which comprises coating with a solution prepared by dissolving the nitrogen-containing condensed ring polymer in an organic solvent, is adopted, r is preferably an integer of 3 to 500, more preferably an integer of 6 to 300, and further preferably an integer of 20 to 200. In particular, since the uniformity of a film becomes favorable when the film is formed by a coating method, the polystyrene-equivalent number average molecular weight of the nitrogen-containing condensed ring polymer is preferably $1\times10^3$ to $1\times10^7$, and more preferably $1\times10^4$ to $1\times10^6$.

Examples of a particularly preferred nitrogen-containing condensed ring polymer include polymers represented by the following formulae (11-1), (11-2), (11-3), (11-4), (11-5), (11-6), (11-7), (11-8), (11-9), (11-10), (11-11), (11-12), (11-13), (11-14), (11-15), and (11-16):

[Chemical Formula 63]

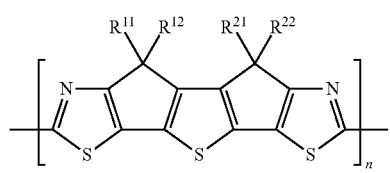

(11-1)

[Chemical Formula 64]

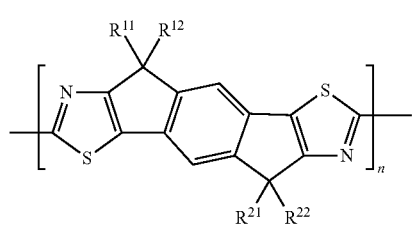

(11-2)

[Chemical Formula 65]

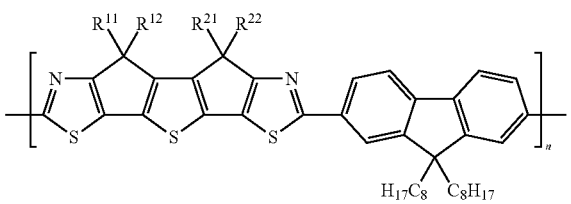

(11-3)

[Chemical Formula 66]

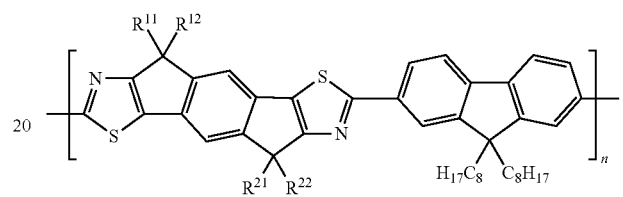

(11-4)

[Chemical Formula 67]

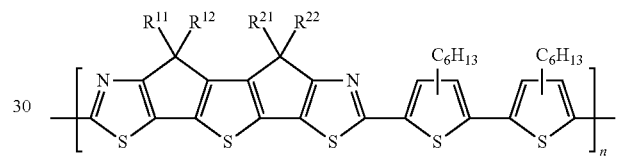

(11-5)

[Chemical Formula 68]

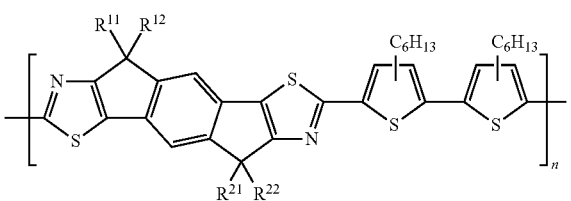

(11-6)

[Chemical Formula 69]

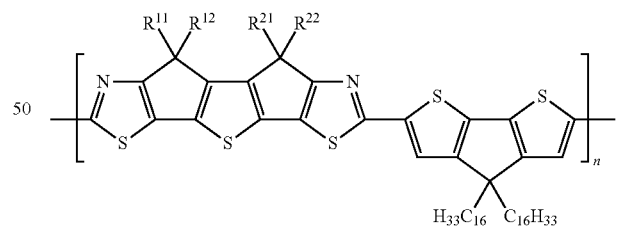

(11-7)

[Chemical Formula 70]

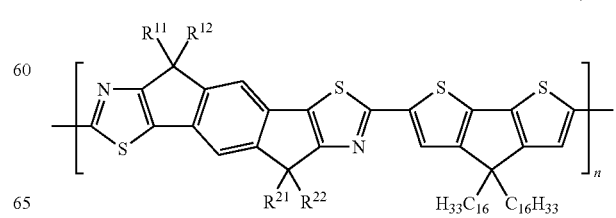

(11-8)

[Chemical Formula 71]

(11-9)

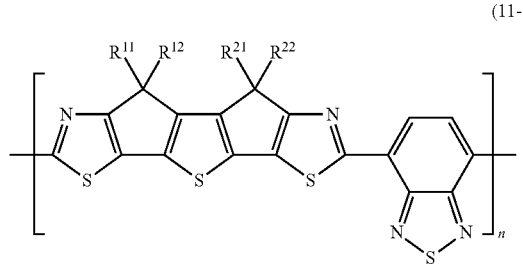

[Chemical Formula 72]

(11-10)

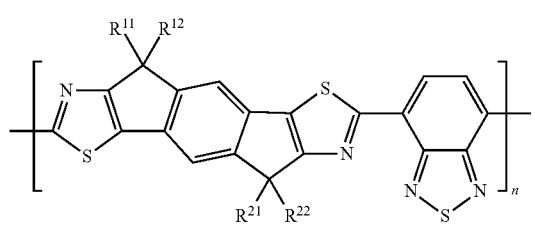

[Chemical Formula 73]

(11-11)

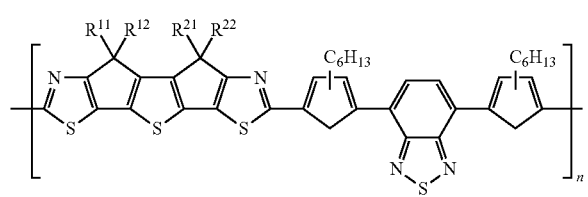

[Chemical Formula 74]

(11-12)

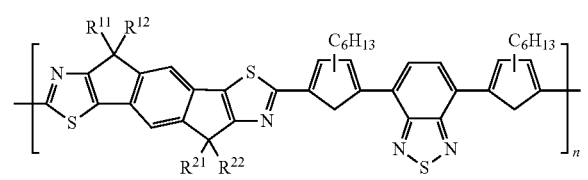

[Chemical Formula 75]

(11-13)

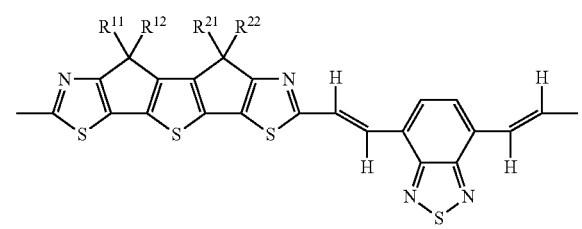

[Chemical Formula 76]

(11-14)

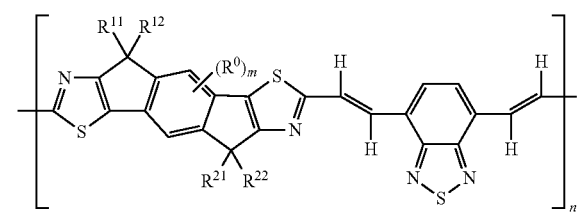

[Chemical Formula 77]

(11-15)

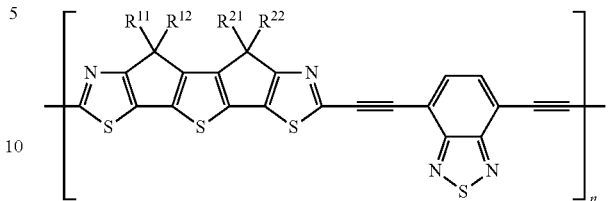

[Chemical Formula 78]

(11-16)

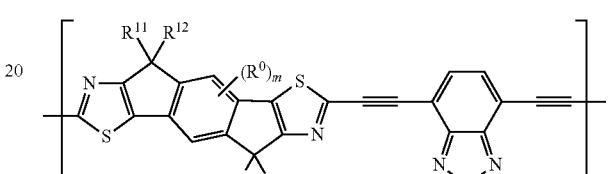

In the formulae (11-1) to (11-8), n represents an integer of 2 to 500, preferably an integer of 2 to 100, and more preferably an integer of 2 to 20.

[Methods for Producing Nitrogen-Containing Condensed Ring Compound and Nitrogen-Containing Condensed Ring Polymer]

Next, methods for producing the nitrogen-containing condensed ring compound and the nitrogen-containing condensed ring polymer according to the above described embodiments will be described. The nitrogen-containing condensed ring compound and the nitrogen-containing condensed ring polymer may be produced by any methods, but they are preferably produced by the following production methods.

First, a method for producing the nitrogen-containing condensed ring compound will be described by taking, as an example, the case of producing the nitrogen-containing condensed ring compound having the structural unit represented by the formula (2-1).

An intermediate compound of the nitrogen-containing condensed ring compound can be produced, for example, in accordance with the following Scheme 1.

Scheme 1

[Chemical Formula 79]

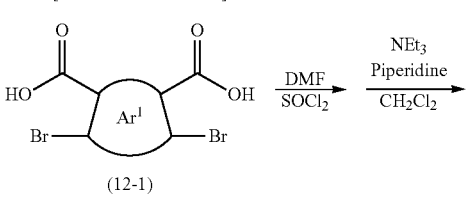

(12-1)

-continued

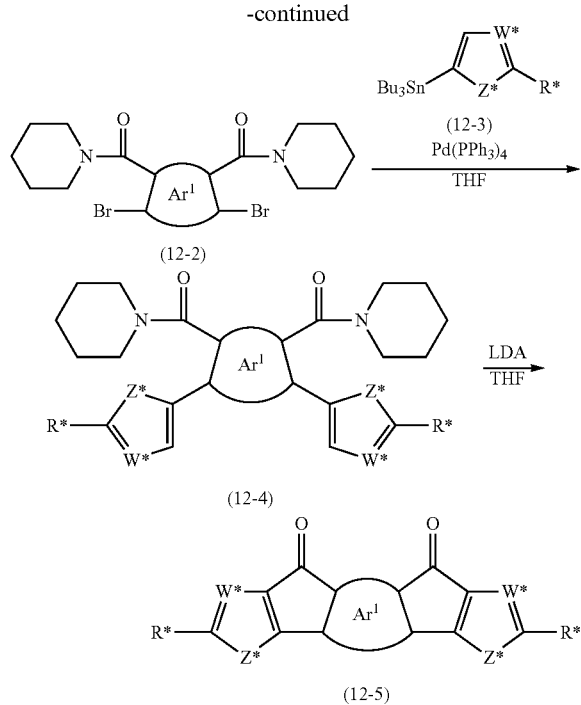

In the Scheme 1, Ar¹ is the same as Ar¹ in the formula (2-1); W* represents W¹ or W² in the formula (2-1); Z* represents Z¹ or Z² in the formula (2-1); and R* represents the same groups as R¹ and R² in the above described formula (6-1) or (6-2).

As shown in the Scheme 1, in production of an intermediate compound of the nitrogen-containing condensed ring compound, as a first step, the compound represented by the formula (12-1) (hereinafter also referred to as "compound (12-1)" at times; the below-mentioned similar descriptions have the same meanings as in the case of this compound) is allowed to react with thionyl chloride (SOCl₂) in the presence of dimethyl formamide (DMF) that is in a catalytic amount, and the resulting compound is further allowed to react with triethylamine and piperidine to obtain the compound (12-2). The reaction of the compound (12-1) with thionyl chloride can be carried out, for example, by mixing a catalytic amount of dimethyl formamide, the compound (12-1), and thionyl chloride that is in an amount of 200 to 4000 mol % based on the total amount of the compound (12-1), and then heating the obtained mixture to reflux.

Subsequently, as a second step, the compound (12-2) is allowed to react with the compound (12-3) in the presence of a palladium catalyst to obtain the compound (12-4). This reaction can be carried out, for example, by heating the compound (12-2), the compound (12-3), and a palladium catalyst that is in an amount of 0.5 to 20 mol % based on the total amount of the compound (12-2), to reflux in toluene. An example of the palladium catalyst that can be used herein is tetrakis(triphenylphosphine)palladium (Pd(PPh₃)).

Thereafter, as a third step, the compound (12-4) is subjected to a cyclization reaction in the presence of lithium diisopropylamide (LDA) to obtain the compound (12-5). This reaction can be carried out, for example, using lithium diisopropylamide in an amount of 200 to 3000 mol % based on the total amount of the compound (12-4) in tetrahydrofuran at a temperature of −78° C. to 0° C.

It is to be noted that, in the first step, an acid chloride such as oxalyl chloride may be used instead of thionyl chloride. In addition, in the second step, tetrahydrofuran or chlorobenzene may be used instead of toluene. Moreover, in the third step, lithium hexamethyldisilazide may be used instead of lithium diisopropylamide.

Furthermore, according to a production method shown in the following Scheme 2, the compound represented by the above described formula (12-5) in which R* is a hydrogen atom (namely, a compound represented by the following formula (12-6)) is used as a starting substance to produce an intermediate compound of the nitrogen-containing condensed ring compound which has a structure in which various groups R** are introduced into the position of R* (namely, a compound represented by the following formula (12-10)).

In the following Scheme 2, the case of synthesizing an intermediate compound in which portions corresponding to Y¹ and Y³ in the formula (2-1) are groups represented by —C(═O)— and —C(═O)—, respectively, will be given as an example. However, even if the above-mentioned portions are groups represented by —C(═X¹)— and —C(═X²)— and X¹ and X² are groups other than oxygen atoms, intermediate compounds of the nitrogen-containing condensed ring compound, into which various groups R** are introduced, can be produced by performing a step of protecting the group represented by ═X¹ or ═X², instead of performing a step of obtaining a compound represented by the following formula (12-7), and other than this step, performing the same operations as in the Scheme 2.

Scheme 2

[Chemical Formula 80]

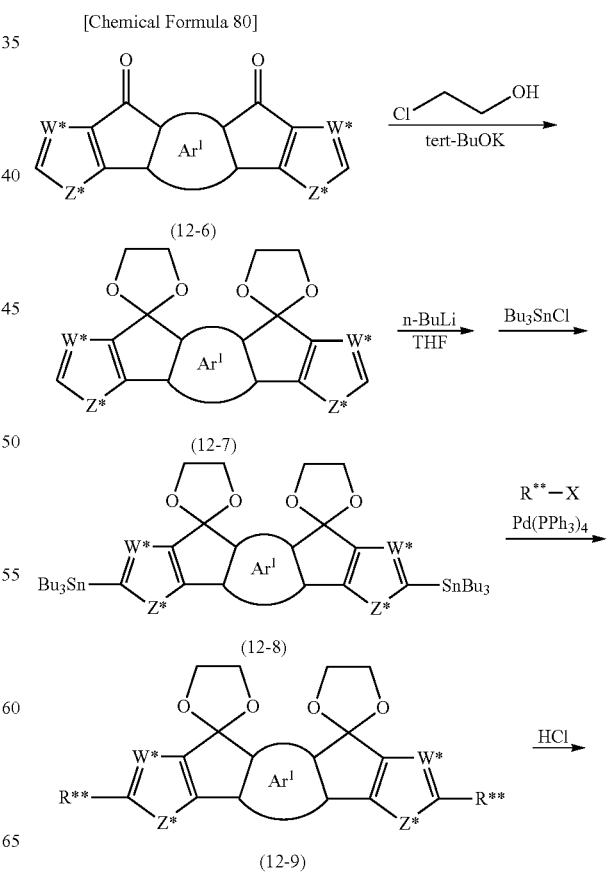

-continued

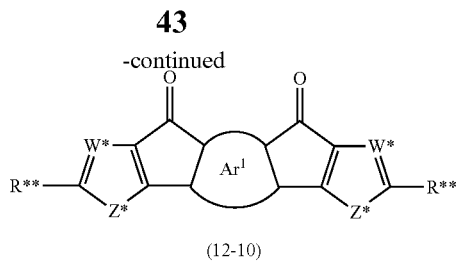

(12-10)

In the Scheme 2, Ar¹, W* and Z* have the same definitions as those in the Scheme 1; R** represents the same groups as those represented by the above described R¹ and R²; and X represents a halogen atom.

In the method for producing an intermediate compound shown in the Scheme 2, as a first step, a carbonyl group in the compound (12-6) is first protected. Specifically, for example, the compound (12-6) is allowed to react with 2-ethanol chloride in the presence of tert-butoxy potassium (tert-BuOK) to obtain the compound (12-7). In order to protect such a carbonyl group, a ketal group such as 2,2-dibutyl-1,3-propenediol may be used instead of 2-ethanol chloride.

Subsequently, as a second step, the compound (12-7) is allowed to react with n-butyllithium (n-BuLi), and the resulting compound is then allowed to react with tributyltin chloride ($Bu_3SnCl$) to obtain the compound (12-8).

Thereafter, as a third step, the compound (12-8) is allowed to react with the compound represented by R—X in the presence of a palladium catalyst to obtain the compound (12-9). This reaction can be carried out by heating the compound (12-8), the compound represented by R—X, and a palladium catalyst in an amount of 0.5 to 20 mol % based on the total amount of the compound (12-8), to reflux in toluene. An example of the palladium catalyst that can be used herein is tetrakis(triphenylphosphine)palladium ($Pd(PPh_3)$).

Further, as a fourth step, the compound (12-9) is allowed to react with hydrochloric acid, for example, in acetic acid, to obtain the compound (12-10) that is an intermediate compound of the nitrogen-containing condensed ring compound, into which various groups are introduced as R**.

It is to be noted that, in the first step of the method for producing an intermediate compound shown in Scheme 2, instead of the reaction using 2-ethanol chloride, a ketalization reaction under general acidic conditions, namely, a reaction of the compound with ethylene glycol in the presence of p-toluenesulfonic acid may be carried out as a step of protecting a carbonyl group. In addition, in the second step, trimethyltin chloride may be used instead of tributyltin chloride. Moreover, in the third step, tetrahydrofuran or chlorobenzene may be used instead of toluene. Furthermore, in the fourth step, a mixed solvent of sulfuric acid, chloroform and acetic acid may be used instead of acetic acid.

The nitrogen-containing condensed ring compound of a preferred embodiment can be produced, for example, by carrying out a reaction shown in the following Scheme 3, using the above-mentioned intermediate compound (namely, the compound represented by the formula (12-5), (12-6), or (12-10)). The Scheme 3 shows, as an example, the case of using the compound (12-10) as an intermediate compound.

Scheme 3

[Chemical Formula 81]

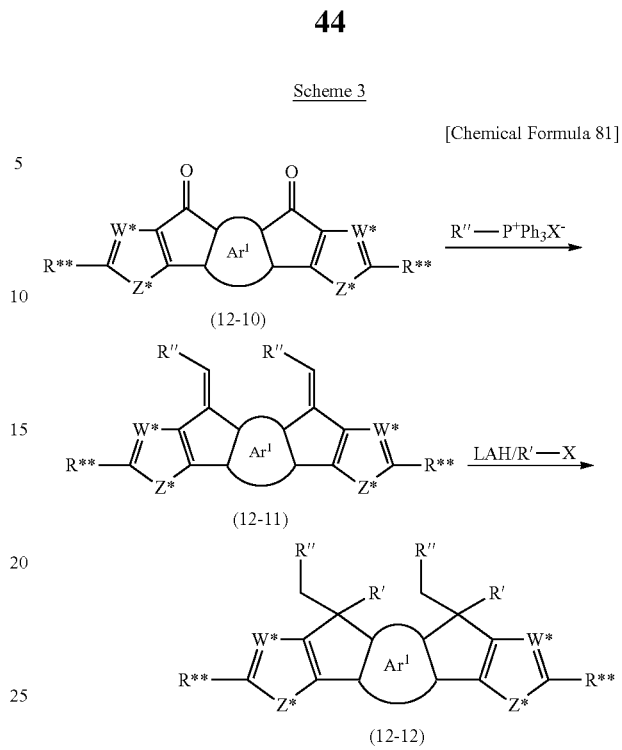

In the Scheme 3, Ar¹, R**, W*, X and Z* have the same definitions as those in the cases of the Schemes 1 and 2; R' represents $R^{21}$ and $R^{22}$ in the formula (2-1) or the like, and groups similar to $R^{21}$ and $R^{22}$; and R" represents a group formed by removing $CH_2$ from the same group as R'.

As shown in the Scheme 3, in production of the nitrogen-containing condensed ring compound, as a first step, a keto group of an intermediate compound is first subjected to olefination. Specifically, in the Scheme 3, the compound (12-10) as an intermediate compound is first allowed to react with alkyltriphenyl phosphonium-halogen to obtain the compound (12-11). Subsequently, as a second step, the compound (12-11) is reduced with lithium aluminum hydride (LAH) and is then allowed to react with alkyl-halogen to produce the nitrogen-containing condensed ring compound (12-12).

Alternatively, the nitrogen-containing condensed ring compound can also be produced by performing steps shown in the following Scheme 4, using the above-mentioned intermediate compound (namely, the compound represented by the formula (12-5), (12-6), or (12-10)). The Scheme 4 shows, as an example, the case of using the compound (12-10) as an intermediate compound.

Scheme 4

[Chemical Formula 82]

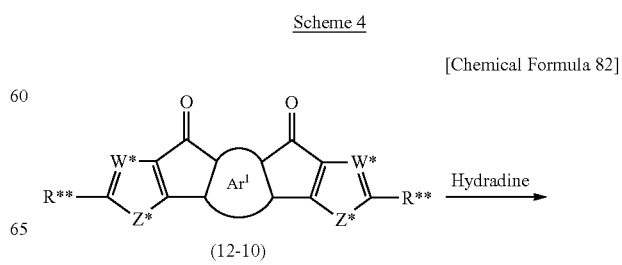

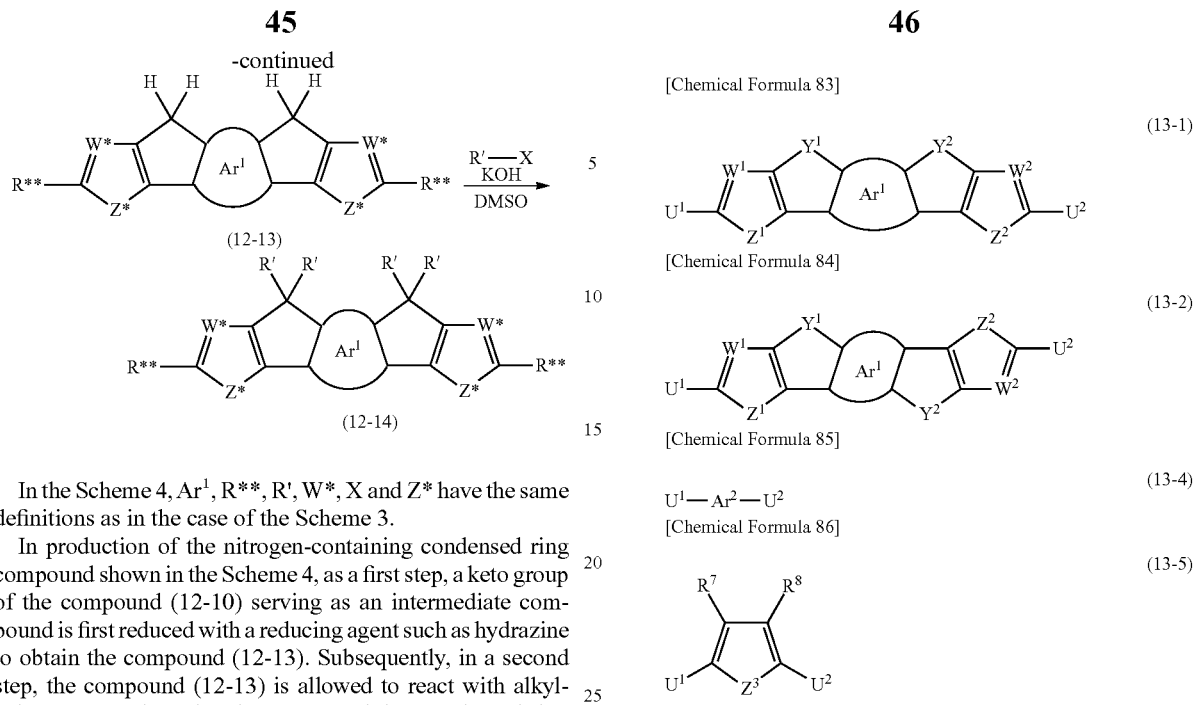

In the Scheme 4, $Ar^1$, $R**$, $R'$, $W*$, $X$ and $Z*$ have the same definitions as in the case of the Scheme 3.

In production of the nitrogen-containing condensed ring compound shown in the Scheme 4, as a first step, a keto group of the compound (12-10) serving as an intermediate compound is first reduced with a reducing agent such as hydrazine to obtain the compound (12-13). Subsequently, in a second step, the compound (12-13) is allowed to react with alkyl-halogen to produce the nitrogen-containing condensed ring compound (12-14).

In the above Schemes 1 to 4, the case of producing the nitrogen-containing condensed ring compound having the structural unit represented by the formula (2-1) is described as an example, but the nitrogen-containing condensed ring compounds having each of the structural units represented by the formulae (2-2), (2-3), (2-4), (2-5), (2-6), (2-7), and (2-8) can also be produced by appropriately substituting the compound (12-1) and the compound (12-3) used in the Scheme 1 with other suitable compounds, while applying the same methods as described above. Moreover, reaction conditions, reaction reagents and the like, which are applied in individual steps of the above described production methods, can be selected from conditions other than the above-exemplified conditions, within a range in which the same steps as described above can be carried out.

When the nitrogen-containing condensed ring compound is used as a material for producing an organic thin film element, since the purity of the compound may have an influence on the properties of the element, it is preferable that the nitrogen-containing condensed ring compounds, for example, obtained by the above described production methods be further purified by methods such as distillation, sublimation purification, or recrystallization.

Next, as a method for producing a nitrogen-containing condensed ring polymer according to a preferred embodiment, a method for producing a nitrogen-containing condensed ring polymer having the structural unit represented by the formula (2-1) as a first structural unit, the structural unit represented by the formula (2-2) as a second structural unit, and the structural unit represented by the formula (4) and the structural unit represented by the formula (5) as third structural units will be given as an example and will be described below.

In this example, for instance, compounds represented by the following formulae (13-1), (13-2), (13-4) and (13-5) (hereinafter respectively referred to as "monomer (13-1)", "monomer (13-2)", "monomer (13-4)", and "monomer (13-5)," as necessary) are used as raw materials and these compounds are reacted to produce the nitrogen-containing condensed ring polymer.

[Chemical Formula 83]

(13-1)

[Chemical Formula 84]

(13-2)

[Chemical Formula 85]

(13-4)

$U^1-Ar^2-U^2$

[Chemical Formula 86]

(13-5)

The groups indicated with individual symbols in the formulae (13-1), (13-2), (13-4) and (13-5) have the same definitions as those of the above described groups indicated with the same symbols. $U^1$ and $U^2$ each independently represent a polymerizable group. Examples of such a polymerizable group include a hydrogen atom, a halogen atom, an alkyl sulfonate group, an aryl sulfonate group, an arylalkyl sulfonate group, an alkyl stannyl group, an aryl stannyl group, an arylalkyl stannyl group, a borate ester residue, a sulfonium methyl group, a phosphonium methyl group, a phosphonate methyl group, a monohalogenated methyl group, a boric acid residue, a formyl group, and a vinyl group. These polymerizable groups are the same as those in the case of the above described $R^1$ and $R^2$.

Among these groups, a halogen atom, an alkyl sulfonate group, an aryl sulfonate group, an arylalkyl sulfonate group, an alkyl stannyl group, a borate ester residue, and a boric acid residue are preferable as polymerizable groups. When polymerizable groups are the above-mentioned groups, a reaction can be easily generated between monomers, and thus, it is synthetically advantageous.

Examples of a reaction method used in production of the nitrogen-containing condensed ring polymer include a method using a Wittig reaction, a method using a Heck reaction, a method using a Homer-Wadsworth-Emmons reaction, a method using a Knoevenagel reaction, a method using a Suzuki coupling reaction, a method using a Grignard reaction, a method using a Stille reaction, a method using a Ni(0) catalyst, a method using an oxidizer such as $FeCl_3$, a method using an electrochemical oxidation reaction, and a method involving decomposition of an intermediate compound having a suitable leaving group.

Among these methods, the method using a Wittig reaction, the method using a Heck reaction, the method using a Homer-Wadsworth-Emmons reaction, the method using a Knoevenagel reaction, the method using a Suzuki coupling reaction, the method using a Grignard reaction, the method using a Stille reaction, and the method using a Ni(0) catalyst are preferable because the structure can be easily controlled in these methods. Further, the method using a Suzuki coupling reaction, the method using a Grignard reaction, the method using a Stille reaction, and the method using a Ni(0) catalyst are more preferable because raw materials can be easily obtained and reaction operations are simple in these methods.

The monomer (13-1), the monomer (13-2), the monomer (13-4) and the monomer (13-5) can be reacted using alkali or a suitable catalyst, if needed, in the state of being dissolved in an organic solvent, at a temperature between the melting point of the organic solvent or higher and the boiling point of the organic solvent or lower.

The organic solvent is different depending on the type of a monomer used and the type of a reaction used, but in order to suppress side reactions, it is preferable that a deoxidation treatment be sufficiently performed on the organic solvent. Examples of the organic solvent used in the reaction include: saturated hydrocarbons such as pentane, hexane, heptane, octane, or cyclohexane; unsaturated hydrocarbons such as benzene, toluene, ethylbenzene, or xylene; halogenated saturated hydrocarbons such as carbon tetrachloride, chloroform, dichloromethane, chlorobutane, bromobutane, chloropentane, bromopentane, chlorohexane, bromohexane, chlorocyclohexane, or bromocyclohexane; halogenated unsaturated hydrocarbons such as chlorobenzene, dichlorobenzene, or trichlorobenzene; alcohols such as methanol, ethanol, propanol, isopropanol, butanol, or tert-butyl alcohol; carboxylic acids such as formic acid, acetic acid, or propionic acid; and ethers such as dimethyl ether, diethyl ether, methyl tert-butyl ether, tetrahydrofuran, tetrahydropyran, or dioxane. Moreover, instead of using such organic solvents, inorganic acids such as hydrochloric acid, bromic acid, hydrofluoric acid, sulfuric acid, or nitric acid may also be used.

When alkali or a suitable catalyst is added, such alkali or catalyst may be selected depending on a reaction to be generated. It is preferable that such alkali or catalyst be sufficiently dissolved in a solvent used in the reaction.

In addition, it is preferable that the reaction progress in an inactive atmosphere. Likewise, it is preferable that a dehydration treatment be carried out during the reaction (however, this is not always applied to reactions that are carried out in a two-phase system with water, such as a Suzuki coupling reaction).

After completion of the reaction, for example, the reaction is terminated with water, extraction is then carried out using an organic solvent, and thereafter, an ordinary post-treatment such as the removal of the solvent by distillation is carried out, so that the nitrogen-containing condensed ring polymer can be obtained. The obtained nitrogen-containing condensed ring polymer can be isolated and purified by methods such as fractionation by chromatography or recrystallization.

When the nitrogen-containing condensed ring polymer is used as a material to produce an organic thin film element, since the purity of the polymer has an influence on the properties of the element, it is preferable that each monomer before the reaction be purified by a method such as distillation, sublimation purification or recrystallization, and be then reacted (polymerized). Moreover, after completion of the synthesis of the nitrogen-containing condensed ring polymer, it is preferable to carry out a purification treatment such as reprecipitation purification or fractionation by chromatography. Furthermore, in order to increase purity to achieve high properties of the element, it is preferable that the nitrogen-containing condensed ring polymer obtained by the above described production method be further subjected to a purification treatment by a method such as distillation, sublimation purification or recrystallization.

In the above described example, the method for producing a nitrogen-containing condensed ring polymer having the structural unit represented by the formula (2-1) as a first structural unit, the structural unit represented by the formula (2-2) as a second structural unit, and the structural unit represented by the formula (4) and the structural unit represented by the formula (5) as third structural units has been described as an example; but nitrogen-containing condensed ring polymers having structural units other than those of the above-mentioned nitrogen-containing condensed ring polymer can also be produced by selecting monomers, while carrying out the same reactions as described above.

[Organic Thin Film]

Next, an organic thin film according to a preferred embodiment will be described. The organic thin film of the present embodiment contains the above described nitrogen-containing condensed ring compound and/or nitrogen-containing condensed ring polymer according to preferred embodiments (which are hereinafter collectively referred to as the "nitrogen-containing compound according to the present embodiment").

The thickness of the organic thin film is preferably 1 nm to 100 μm, more preferably 2 nm to 1000 nm, further preferably 5 nm to 500 nm, and still further preferably 20 nm to 200 nm.

The organic thin film may comprise one type of the nitrogen-containing compound according to the present embodiment alone, or may comprise two or more types of the present nitrogen-containing compounds in combination. Moreover, in order to enhance the electron transport property or hole transport property of the organic thin film, the organic thin film may comprise a low-molecular-weight compound or high-molecular-weight compound having an electron transport property (hereinafter referred to as an "electron-transporting material"), and a low-molecular-weight compound or high-molecular-weight compound having a hole transport property (hereinafter referred to as a "hole-transporting material," as well as the nitrogen-containing compound according to the present embodiment.

As a hole-transporting material, a known hole-transporting material can be used. Examples of such a hole-transporting material include a pyrazoline derivative, an arylamine derivative, a stilbene derivative, a triaryldiamine derivative, oligothiophene and a derivative thereof, polyvinylcarbazole and a derivative thereof, polysilane and a derivative thereof, a polysiloxane derivative having an aromatic amine in the side chain or main chain thereof, polyaniline and a derivative thereof, polythiophene and a derivative thereof, polypyrrole and a derivative thereof, polyarylenevinylene and a derivative thereof, and polythienylenevinylene and a derivative thereof.

Also, as an electron-transporting material, a known electron-transporting material can be used. Examples of such an electron-transporting material include an oxadiazole derivative, anthraquinodimethane and a derivative thereof, benzoquinone and a derivative thereof, naphthoquinone and a derivative thereof, anthraquinone and a derivative thereof, tetracyanoanthraquinodimethane and a derivative thereof, a fluorenone derivative, diphenyldicyanoethylene and a derivative thereof, a diphenoquinone derivative, or a metal complex of 8-hydroxyquinoline and a derivative thereof, polyquinoline and a derivative thereof, polyquinoxaline and a derivative thereof, and polyfluorene and a derivative thereof, and fullerenes such as $C_{60}$ and derivatives thereof.

In addition, in order to generate charge by absorbed light in the organic thin film, the organic thin film may comprise a charge generation material. As such a charge generation material, a known charge generation material can be used. Examples of such a charge generation material include an azo compound and a derivative thereof, a diazo compound and a derivative thereof, a metal-free phthalocyanine compound and a derivative thereof, a metal phthalocyanine compound and a derivative thereof, a perylene compound and a derivative thereof, a polycyclic quinone compound and a derivative thereof, a squarylium compound and a derivative thereof, an azlenium compound and a derivative thereof, a thiapyrylium compound and a derivative thereof, and fullerenes such as $C_{60}$ and derivatives thereof.

Moreover, the organic thin film may comprise other materials necessary for exhibiting various functions. Examples of such other materials include a sensitizer for sensitizing the function to generate charge by the absorbed light, a stabilizer for enhancing stability, and a UV absorber for absorbing ultraviolet (UV) light.

Furthermore, in order to enhance mechanical properties, the organic thin film may comprise a polymer material other than the nitrogen-containing compound according to the present embodiment as a polymer binder. As such a polymer binder, a polymer binder that does not inhibit the electron transport property or hole transport property so much is preferable, and a polymer binder that does not absorb visible light so much is preferably used.

Examples of such a polymer binder include poly(N-vinylcarbazole), polyaniline and a derivative thereof, polythiophene and a derivative thereof, poly(p-phenylenevinylene) and a derivative thereof, poly(2,5-thienylenevinylene) and a derivative thereof, polycarbonate, polyacrylate, polymethyl acrylate, polymethyl methacrylate, polystyrene, polyvinyl chloride, and polysiloxane.

An example of a method for producing the organic thin film of the present embodiment is a method which comprises forming a film using a solution containing an electron-transporting material or a hole-transporting material and a polymer binder to be mixed as necessary, as well as the nitrogen-containing compound according to the present embodiment. When the nitrogen-containing compound according to the present embodiment has sublimability, it may also be possible to form a thin film according to a vacuum evaporation method.

The solvent used in film formation using such a solution is not particularly limited, as long as the nitrogen-containing compound according to the present embodiment, and an electron-transporting material or hole-transporting material and a polymer binder, which are mixed with the aforementioned compound, can be dissolved therein. Examples of such a solvent include: unsaturated hydrocarbon solvents such as toluene, xylene, mesitylene, tetralin, decalin, bicyclohexyl, n-butyl benzene, sec-butyl benzene, or tert-butyl benzene; halogenated saturated hydrocarbon solvents such as carbon tetrachloride, chloroform, dichloromethane, dichloroethane, chlorobutane, bromobutane, chloropentane, bromopentane, chlorohexane, bromohexane, chlorocyclohexane, or bromocyclohexane; halogenated unsaturated hydrocarbon solvents such as chlorobenzene, dichlorobenzene, or trichlorobenzene; and ether solvents such as tetrahydropyran or tetrahydropyran. The nitrogen-containing compound according to the present embodiment can be generally dissolved at a mass percentage of 0.1% or more in such a solvent, although it depends on the structure or molecular weight thereof.

Examples of the method for forming a film using a solution include coating methods such as a spin-coating method, a casting method, a microgravure coating method, a gravure coating method, a bar coating method, a roll coating method, a wire bar coating method, a dip coating method, a spray coating method, a screen printing method, a flexographic printing method, an offset printing method, an ink-jet printing method, a dispenser printing method, a nozzle coating method, and a capillary coating method. Among these methods, a spin-coating method, a flexographic printing method, an ink-jet printing method, a dispenser printing method, a nozzle coating method, and a capillary coating method are preferable.

The process of producing the organic thin film may comprise a step of orienting the nitrogen-containing compound according to the present embodiment. By orienting the nitrogen-containing compound by this step, main chain molecules or side chain molecules are aligned in one direction, so that electron mobility or hole mobility caused by the organic thin film can be improved.

As a method of orienting the nitrogen-containing compound according to the present embodiment, a method known as a means for orientation of liquid crystal can be used. Among others, a rubbing method, a photo-alignment method, a sharing method (shear stress application method), and a drawing-up coating method are simple and effective and can be easily used as orientation methods, and further, a rubbing method and a shearing method are more preferable.

Moreover, the process of producing the organic thin film may comprise a step of annealing a film after completion of the film formation. By this step, the quality of the organic thin film can be improved, for example, the interaction between the nitrogen-containing compounds according to the present embodiment can be promoted, and as a result, electron mobility or hole mobility can be further improved. The temperature applied in the annealing treatment is preferably a temperature between 50° C. and a temperature around the glass transition temperature (Tg) of the nitrogen-containing compound according to the present embodiment, and is more preferably a temperature between (Tg −30° C.) and Tg. The time required for the annealing treatment is preferably from 1 minute to 10 hours, and more preferably from 10 minutes to 1 hour. The atmosphere in which the annealing treatment is carried out is preferably in a vacuum or in an inert gas atmosphere.

Since the organic thin film of the present embodiment has an electron transport property or a hole transport property, it can be used in various organic thin film elements, such as an organic thin film transistor, an organic thin film solar cell, or an optical sensor, by controlling the transport of electron or hole injected from electrodes or charge generated as a result of light absorption. When the organic thin film is used in these organic thin film elements, it is more preferable to use the organic thin film after being oriented by an orientation treatment, in order to achieve a high electron transport property or hole transport property.

[Organic Thin Film Element]

Since the above described organic thin film according to a preferred embodiment contains the nitrogen-containing compound according to the present embodiment, it has an excellent electron transport property or hole transport property. Accordingly, this organic thin film can efficiently transport electron or hole injected from electrodes or the like, charge generated as a result of light absorption, etc., and thus, it can also be applied to various electrical elements (organic thin film elements) containing such an organic thin film. Moreover, since the nitrogen-containing compound according to the present embodiment is also excellent in terms of environmental stability, it becomes possible to obtain an organic thin film element whose performance is stable even in an ordinary atmosphere, by forming an organic thin film using the nitrogen-containing compound according to the present embodiment. Hereinafter, examples of the organic thin film element will be given and described.

(Organic Thin Film Transistor)

First, an organic thin film transistor according to a preferred embodiment will be described. The organic thin film transistor may have a structure comprising a source electrode, a drain electrode, an active layer serving as a current pathway between these electrodes and containing the nitrogen-containing compound according to the present embodiment (namely, an organic thin film layer), and a gate electrode that regulates the amount of current passing through the current pathway. Examples of such an organic thin film transistor include a field-effect organic thin film transistor and a static induction organic thin film transistor.

The field-effect organic thin film transistor preferably comprises a source electrode, a drain electrode, an active layer serving as a current pathway between these electrodes and containing the nitrogen-containing compound according to the present embodiment, a gate electrode that regulates the amount of current passing through the current pathway, and an insulating layer disposed between the active layer and the gate electrode. In particular, it is preferable that the source electrode and the drain electrode be established adjacent to the active layer containing the nitrogen-containing compound according to the present embodiment, and further that the gate electrode be established on the insulating layer adjacent to the active layer.

It is preferable that the static induction organic thin film transistor have a source electrode, a drain electrode, an active layer serving as a current pathway between these electrodes and containing the nitrogen-containing compound according to the present embodiment, and a gate electrode that regulates the amount of current passing through the current pathway, and that the gate electrode be established in the active layer. In particular, it is preferable that the source electrode, the drain electrode, and the gate electrode established in the active layer be established adjacent to the active layer containing the nitrogen-containing compound according to the present embodiment. The structure of the gate electrode may be a structure in which a current pathway passing from the source electrode to the drain electrode is formed, and in which the amount of current passing through the current pathway can be regulated by voltage applied to the gate electrode; and for example, it is a comb electrode.

FIG. 1 is a schematic sectional view of an organic thin film transistor (field-effect organic thin film transistor) according to a first embodiment. An organic thin film transistor 100 shown in FIG. 1 comprises a substrate 1, a source electrode 5 and a drain electrode 6 that are formed on the substrate 1 with a certain distance therebetween, an active layer 2 formed on the substrate 1 such that it covers the source electrode 5 and the drain electrode 6, an insulating layer 3 formed on the active layer 2, and a gate electrode 4 formed on the insulating layer 3 such that it covers the region of the insulating layer 3 between the source electrode 5 and the drain electrode 6.

Figure 2:
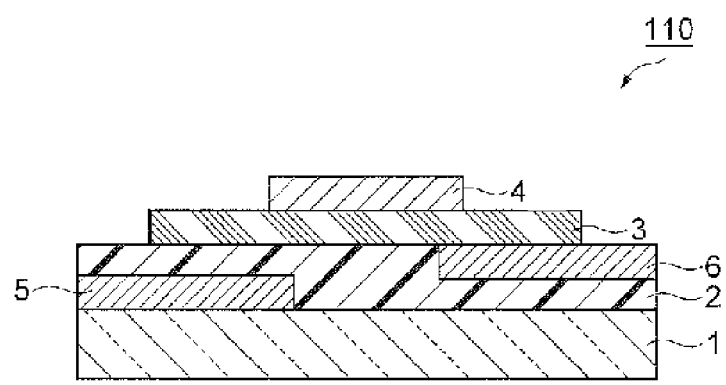
FIG. 2 is a schematic sectional view of an organic thin film transistor according to a second embodiment.

FIG. 2 is a schematic sectional view of an organic thin film transistor (field-effect organic thin film transistor) according to a second embodiment. An organic thin film transistor 110 shown in FIG. 2 comprises a substrate 1, a source electrode 5 formed on the substrate 1, an active layer 2 formed on the substrate 1 such that it covers the source electrode 5, a drain electrode 6 formed on the active layer 2 with a certain distance from the source electrode 5, an insulating layer 3 formed on the active layer 2 and the drain electrode 6, and a gate electrode 4 formed on the insulating layer 3 such that it covers the region of the insulating layer 3 between the source electrode 5 and the drain electrode 6.

Figure 3:
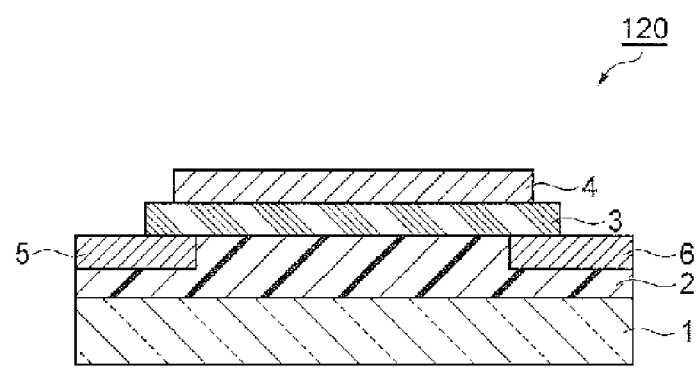
FIG. 3 is a schematic sectional view of an organic thin film transistor according to a third embodiment.

FIG. 3 is a schematic sectional view of an organic thin film transistor (field-effect organic thin film transistor) according to a third embodiment. An organic thin film transistor 120 shown in FIG. 3 comprises a substrate 1, an active layer 2 formed on the substrate 1, a source electrode 5 and a drain electrode 6 that are formed on the active layer 2 with a certain distance therebetween, an insulating layer 3 formed on the active layer 2 such that it partially covers the source electrode 5 and the drain electrode 6, and a gate electrode 4 formed on the insulating layer 3 such that it partially covers the region of the insulating layer 3 below which the source electrode 5 is formed and the region of the insulating layer 3 below which the drain electrode 6 is formed.

Figure 4:
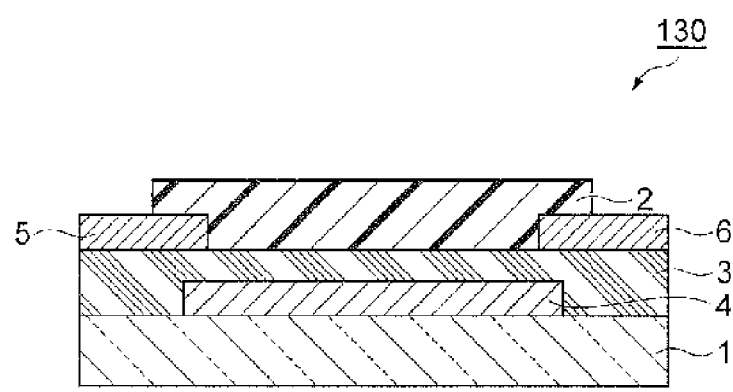
FIG. 4 is a schematic sectional view of an organic thin film transistor according to a fourth embodiment.

FIG. 4 is a schematic sectional view of an organic thin film transistor (field-effect organic thin film transistor) according to a fourth embodiment. An organic thin film transistor 130 shown in FIG. 4 comprises a substrate 1, a gate electrode 4 formed on the substrate 1, an insulating layer 3 formed on the substrate 1 such that it covers the gate electrode 4, a source electrode 5 and a drain electrode 6 that are formed on the insulating layer 3 with a certain distance therebetween, such that they partially cover the region of the insulating layer 3 below which the gate electrode 4 is formed, and an active layer 2 formed on the insulating layer 3 such that it partially covers the source electrode 5 and the drain electrode 6.

Figure 5:
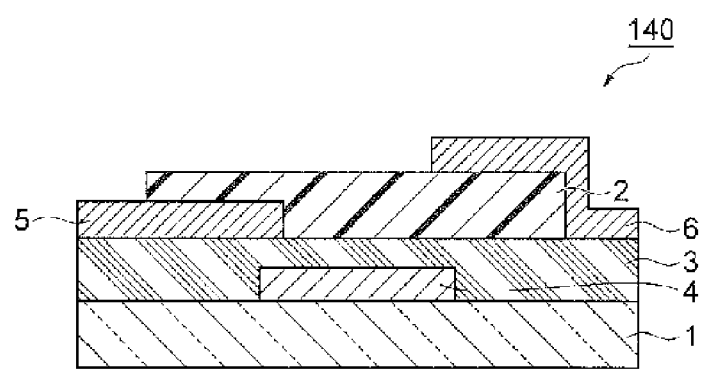
FIG. 5 is a schematic sectional view of an organic thin film transistor according to a fifth embodiment.

FIG. 5 is a schematic sectional view of an organic thin film transistor (field-effect organic thin film transistor) according to a fifth embodiment. An organic thin film transistor 140 shown in FIG. 5 comprises a substrate 1, a gate electrode 4 formed on the substrate 1, an insulating layer 3 formed on the substrate 1 such that it covers the gate electrode 4, a source electrode 5 formed on the insulating layer 3 such that it partially covers the region of the insulating layer 3 below which the gate electrode 4 is formed, an active layer 2 formed on the insulating layer 3 such that it partially covers the source electrode 5, and a drain electrode 6 formed on the insulating layer 3 with a certain distance from the source electrode 5, such that it partially covers the region of the active layer 2 below which the gate electrode 4 is formed.

Figure 6:
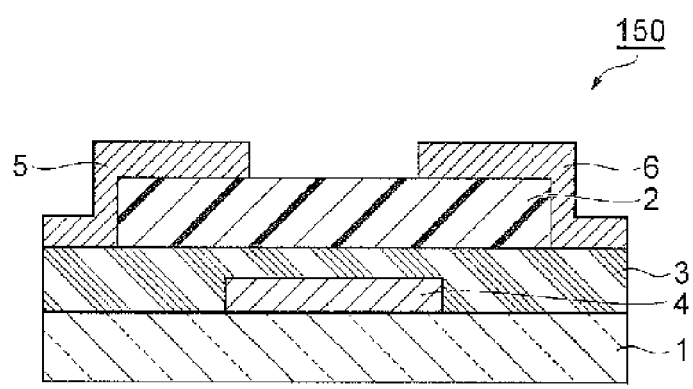
FIG. 6 is a schematic sectional view of an organic thin film transistor according to a sixth embodiment.

FIG. 6 is a schematic sectional view of an organic thin film transistor (field-effect organic thin film transistor) according to a sixth embodiment. An organic thin film transistor 150 shown in FIG. 6 comprises a substrate 1, a gate electrode 4 formed on the substrate 1, an insulating layer 3 formed on the substrate 1 such that it covers the gate electrode 4, an active layer 2 formed such that it covers the region of the insulating layer 3 below which the gate electrode 4 is formed, a source electrode 5 formed on the insulating layer 3 such that it partially covers the region of the active layer 2 below which the gate electrode 4 is formed, and a drain electrode 6 formed on the insulating layer 3 with a certain distance from the source electrode 5, such that it partially covers the region of the active layer 2 below which the gate electrode 4 is formed.

Figure 7:
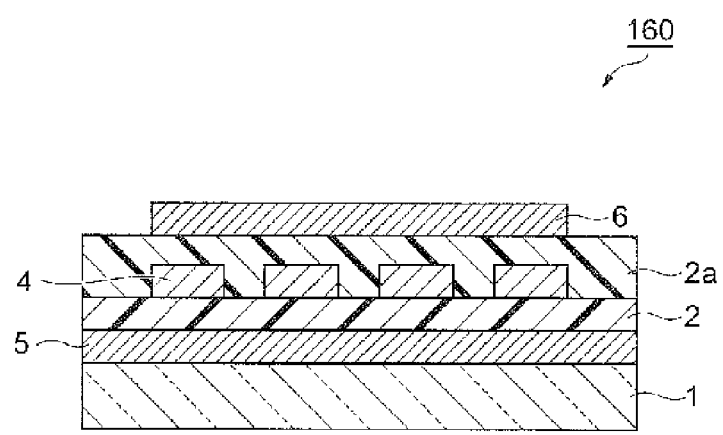
FIG. 7 is a schematic sectional view of an organic thin film transistor according to a seventh embodiment.

FIG. 7 is a schematic sectional view of an organic thin film transistor (static induction organic thin film transistor) according to a seventh embodiment. An organic thin film transistor 160 shown in FIG. 7 comprises a substrate 1, a source electrode 5 formed on the substrate 1, an active layer 2 formed on the source electrode 5, a plurality of gate electrodes 4 that are formed on the active layer 2 with a certain distance among them, an active layer 2a formed on the active layer 2 such that it covers all of the gate electrodes 4 (wherein the material constituting the active layer 2a may be identical to or different from that of the active layer 2), and a drain electrode 6 formed on the active layer 2a.

In the organic thin film transistors according to the first to seventh embodiments, the active layer 2 and/or the active layer 2a contain(s) the nitrogen-containing compound according to the present embodiment, and they serve as current channels between the source electrode 5 and the drain electrode 6. In addition, by application of voltage, the gate electrode 4 regulates the amount of current that passes through the current channel(s) of the active layer 2 and/or the active layer 2a.

Such field-effect organic thin film transistors can be produced by known methods such as the method described in Japanese Patent Application Laid-Open No. 5-110069. Moreover, such static induction organic thin film transistors can be produced by known methods such as the method described in Japanese Patent Application Laid-Open No. 2004-006476.

The type of the substrate 1 is not particularly limited as long as it does not inhibit the properties of the organic thin film transistor, and a glass substrate, a flexible film substrate or plastic substrate can be used.

Upon forming the active layer 2, it is preferable to use a compound soluble in an organic solvent because it is advantageous for the production thereof. In such a case, an organic thin film used as an active layer 2 can be formed by applying the above described method for producing an organic thin film.

The material of the insulating layer 3 formed adjacent to the active layer 2 is not particularly limited as long as it is a material having a high electrical insulation property, and a known material can be used. Examples of such a material include SiOx, SiNx, $Ta_2O_5$, polyimide, polyvinyl alcohol, polyvinyl phenol, organic glass, and photoresist. A material with a high dielectric constant is preferable because it achieves low voltage.

When an active layer 2 is formed on an insulating layer 3, in order to improve the interfacial property between the insulating layer 3 and the active layer 2, it is also possible that the active layer 2 will be formed on the insulating layer 3, after the treatment of the surface of the insulating layer 3 with a surface-treating agent such as a silane coupling agent to modify the surface. Examples of such a surface-treating agent include long-chain alkylchlorosilanes long-chain alkylalkoxysilanes, fluorinated alkylchlorosilanes, fluorinated alkylalkoxysilanes, and silylamine compounds such as hexamethyldisilazane. It is also possible that the surface of the insulating layer will have been treated with ozone UV or $O_2$ plasma, before it is treated with a surface-treating agent.

Moreover, after completion of the production of an organic thin film transistor, it is preferable to form a protective film on the organic thin film transistor in order to protect the element. Thereby, the organic thin film transistor is disconnected from the atmosphere, so that a reduction in the properties of the organic thin film transistor can be suppressed. Furthermore, with the use of such a protective film, external influences can be reduced in a step of forming a display device to be driven on the organic thin film transistor.

An example of a method of forming a protective film is a method which comprises covering the organic thin film transistor with a UV-setting resin, a thermosetting resin, or an inorganic SiONx film. In order to effectively carry out disconnection from the atmosphere, it is preferable that, after completion of the production of the organic thin film transistor, a step of forming a protective film be carried out without exposing the transistor to the atmosphere (e.g. in a dry nitrogen atmosphere, in a vacuum, etc.).

(Solar Cell)

Figure 8:
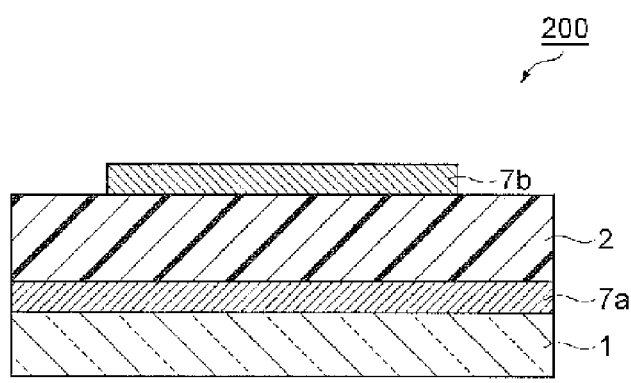
FIG. 8 is a schematic sectional view of a solar cell according to a preferred embodiment.

Next, application of the organic thin film according to a preferred embodiment to a solar cell will be described. FIG. 8 is a schematic sectional view showing a solar cell according to a preferred embodiment. A solar cell 200 shown in FIG. 8 comprises a substrate 1, a first electrode 7a formed on the substrate 1, an active layer 2 consisting of an organic thin film containing the nitrogen-containing compound according to the present embodiment that is formed on the first electrode 7a, and a second electrode 7b formed on the active layer 2.

In the solar cell according to the present embodiment, a transparent or semi-transparent electrode is used as one of the first electrode 7a and the second electrode 7b. Examples of the electrode material that can be used herein include aluminum, gold, silver, copper, metals such as alkaline metal or alkaline earth metal, and a semi-transparent or transparent conductive film thereof. To obtain a high open-circuit voltage, it is preferable to select individual electrodes such that a difference in work function becomes large. In order to increase luminosity sensitivity, a charge generation agent, a sensitizer and the like may be added into the active layer 2 (organic thin film), and it may be then used. As the substrate 1, a silicon substrate, a glass substrate, a plastic substrate, or the like can be used.

(Optical Sensor)

Figure 9:
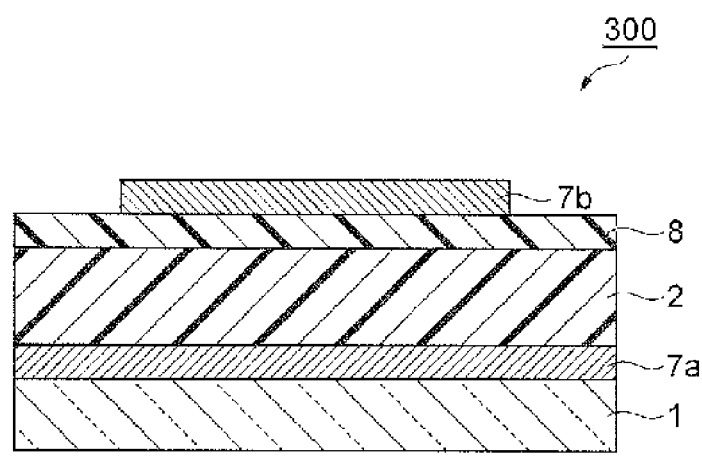
FIG. 9 is a schematic sectional view of an optical sensor according to the first embodiment.

Next, application of the organic thin film according to the present embodiment to an optical sensor will be described. FIG. 9 is a schematic sectional view showing an optical sensor according to a first embodiment. An optical sensor 300 shown in FIG. 9 comprises a substrate 1, a first electrode 7a formed on the substrate 1, an active layer 2 consisting of an organic thin film containing the nitrogen-containing compound according to the present embodiment that is formed on the first electrode 7a, a charge generation layer 8 formed on the active layer 2, and a second electrode 7b formed on the charge generation layer 8.

Figure 10:
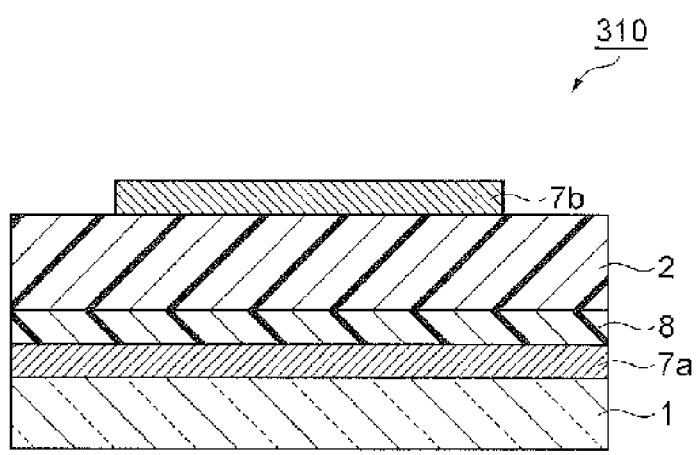
FIG. 10 is a schematic sectional view of an optical sensor according to the second embodiment.

FIG. 10 is a schematic sectional view showing an optical sensor according to a second embodiment. An optical sensor 310 shown in FIG. 10 comprises a substrate 1, a first electrode 7a formed on the substrate 1, a charge generation layer 8 formed on the first electrode 7a, an active layer 2 consisting of an organic thin film containing the nitrogen-containing compound according to the present embodiment that is formed on the charge generation layer 8, and a second electrode 7b formed on the active layer 2.

Figure 11:
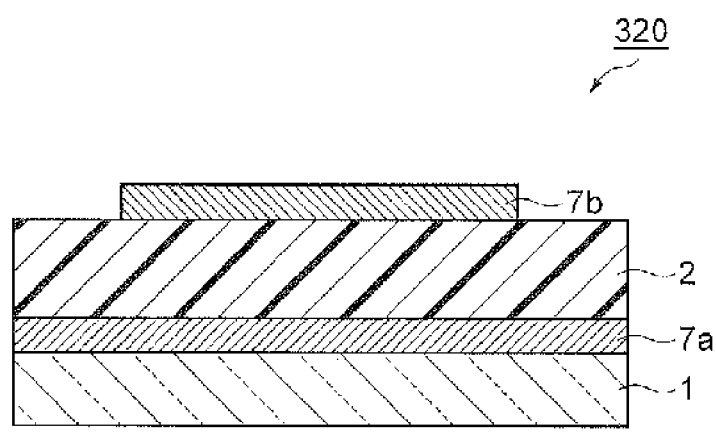
FIG. 11 is a schematic sectional view of an optical sensor according to the third embodiment.

FIG. 11 is a schematic sectional view showing an optical sensor according to a third embodiment. An optical sensor 320 shown in FIG. 11 comprises a substrate 1, a first electrode 7a formed on the substrate 1, an active layer 2 consisting of an organic thin film containing the nitrogen-containing compound according to the present embodiment that is formed on the first electrode 7a, and a second electrode 7b formed on the active layer 2.

In the optical sensors according to the first to third embodiments, a transparent or semi-transparent electrode is used as one of the first electrode 7a and the second electrode 7b. The charge generation layer 8 is a layer that absorbs light to generate charge. Examples of the electrode material that can be used herein include aluminum, gold, silver, copper, metals such as alkaline metal or alkaline earth metal, and a semi-transparent or transparent conductive film thereof. In order to increase luminosity sensitivity, a carrier generation agent, a sensitizer and the like may be added into the active layer 2 (organic thin film), and it may be then used. Moreover, as the substrate 1, a silicon substrate, a glass substrate, a plastic substrate, or the like can be used.

As given above, the present invention has been described in detail based on the embodiments thereof; however, the present invention is not necessarily limited to the above described embodiments, and it may be modified in various ways in a range in which it does not deviate from the gist of the present invention.

EXAMPLES

Hereinafter, the present invention will be more specifically described based on Examples and Comparative Examples, but the following examples are not intended to limit the scope of the present invention.

In the following Examples and Comparative Examples, a compound represented by a formula (A) is referred to as "Compound A" for example, and compounds represented by formulae (B) to (P) are also referred to in the same manner.

[Measurement Conditions, etc.]

First, the conditions of individual measurements conducted in the below-mentioned experiments will be described. Nuclear magnetic resonance (NMR) spectrum was measured using JMN-270 (trade name) (270 MHz at $^1$H measurement) manufactured by JEOL Ltd., or JMNLA-600 (trade name) (600 MHz at $^{19}$F measurement) manufactured by the same company as described above. Chemical shift is indicated with parts per million (ppm). As an internal standard (0 ppm), tetramethylsilane (TMS) was used. Coupling constant (J) is indicated with hertz, and the abbreviations s, d, t, q, m, and br indicate singlet, doublet, triplet, quartet, multiplet, and broad line, respectively. Moreover, the symbols dd, td, and hept indicate doublet-doublet, triplet-doublet, and heptet, respectively.

Furthermore, mass spectrometry (MS) was measured according to an electron ionization (EI) method or a direct introduction (DI) method, using GCMS-QP5050A (trade name) manufactured by Shimadzu Corporation. As silica gel used in column chromatography, Silicagel 60N (trade name) (40 to 50 μm) manufactured by Kanto Chemical Co., Inc. was used. All of chemical substances were of reagent grades, and were purchased from Wako Pure Chemical Industries, Ltd., Tokyo Chemical Industry Co., Ltd., Kanto Chemical Co., Inc., Nacalai Tesque, Inc., Sigma-Aldrich Japan, or Daikin Kaseihin Hanbai Co., Ltd.

Further, the polystyrene-equivalent molecular weight of a polymer was measured using the following apparatuses.

Analytic liquid chromatography (GPC): Hitachi Corporation/LaChrom ELITE HTA: L-2130 (Pump), L-2420 (UV-Vis detector): Tosoh Corporation/CO-8020 (column oven)

As a column, Shodex K-803L was used, and the polystyrene-equivalent molecular weight was measured using a chloroform solvent at a temperature of 40° C.

Example 1

Synthesis of Compound A 2,5-Dibromothiophene-3,4-dicarboxylic acid (100 mg, 0.303 mmol), a catalytic amount of dimethyl formamide, and an excessive amount of thionyl chloride were added into an eggplant flask, and the obtained mixture was then refluxed for 1 hour. After completion of the reaction, thionyl chloride was distilled away in a vacuum. Subsequently, the resultant was cooled to 0° C., and triethylamine (0.25 mL, 1.818 mmol) was then added thereto, and piperidine (0.18 mL, 1.818 mmol) was further added dropwise to the mixture. After completion of the dropwise addition, the obtained mixture was stirred at a room temperature. Three hours later, water was added to the reaction mixture, and the mixture was then extracted with chloroform. The organic layer was dried over magnesium sulfate and was then concentrated under a reduced pressure. The resultant was purified by silica gel column chromatography (hexane/ethyl acetate=1/1 (volume ratio)) to obtain Compound A (61 mg, yield: 43%) as a desired product in the form of reddish powders. The analysis results and chemical formula of the obtained Compound A are as follows.

TLC $R_f$=0.33 (hexane/ethyl acetate=1/1 (volume ratio))
GC-MS (DI): m/z=464 (M$^+$).

[Chemical Formula 87]

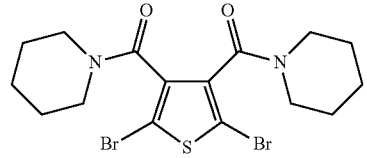

(A)

Synthesis of Compound B

Compound A (61 mg, 0.131 mmol), 2-triisopropylsilyl-5-tributyltin-thiazole (153 mg, 0.288 mmol), tetrakis(triphenylphosphine)palladium(0) (15 mg, 0.013 mmol), and toluene (2 mL) were added into a test tube with lid that had been dried by heating, and the gas in the test tube was then purged with nitrogen gas, and the mixture was then reflux for 8 hours. Thereafter, the reaction solution was filtrated with Celite and was then concentrated under a reduced pressure. The resultant was purified by silica gel column chromatography (hexane/ethyl acetate=2/1 (volume ratio)) to obtain Compound B (93 mg, yield: 79%) as a desired product in the form of a yellow liquid. The analysis results and chemical formula of the obtained Compound B are as follows. It is to be noted that TIPS in the formula indicates a triisopropylsilyl group.

TLC $R_f$=0.32 (hexane/ethyl acetate=2/1 (volume ratio))
$^1$H NMR (400 MHz, CDCl$_3$): δ (ppm)=8.20 (s, 2H).
GC-MS (DI): m/z=785 (M$^+$).

[Chemical Formula 88]

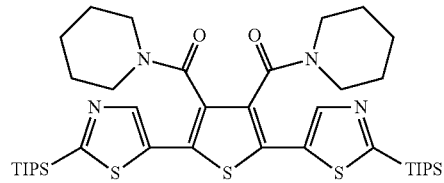

(B)

Synthesis of Compound C

Compound B (93 mg, 0.118 mmol) and tetrahydrofuran (2 mL) were added into an eggplant flask that had been dried by heating. The gas in the eggplant flask was purged with nitrogen gas, and the mixture was then cooled to −78° C., and lithium diisopropylamide (1M, 2.6 mL, 1.43 mmol) was then added thereto, followed by performing a reaction. One hour later, water was added to the reaction mixture at −78° C., and the temperature of the mixture was then increased to a room temperature, followed by extraction with chloroform. The organic layer was dried over magnesium sulfate and was then concentrated under a reduced pressure. The resultant was purified by silica gel column chromatography (hexane/ethyl acetate=10/1 (volume ratio)) to obtain Compound C (1 mg, yield: 1.3%) as a desired product in the form of a violet solid. The obtained Compound C was soluble in chloroform, ethyl acetate, and tetrahydrofuran. The analysis results and chemical formula of the obtained Compound C are as follows.

TLC $R_f$=0.27 (hexane/ethyl acetate=8/1 (volume ratio))

$^1$H NMR (400 MHz, CDCl$_3$): δ (ppm)=1.46 (m, 6H), 1.15 (d, 36H).

GC-MS (DI): m/z=614 (M$^+$)

[Chemical Formula 89]

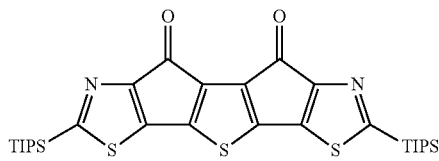

(C)

Synthesis of Compound D

Dodecyltriphenylphosphonium bromide and tetrahydrofuran are added into an eggplant flask that has been dried by heating. The gas in the eggplant flask is purged with nitrogen gas, and the mixture is then cooled to −78° C., and n-butyllithium is then added thereto, followed by stirring the mixture. To this solution, a tetrahydrofuran solution of the Compound C is added, and the obtained mixture is then reacted while stirring. The temperature of the reaction solution is increased to a room temperature, and water is then added to the reaction solution to terminate the reaction, followed by extraction with ethyl acetate. The organic layer is dried over magnesium sulfate and is then concentrated under a reduced pressure, and thereafter, the resultant is purified by silica gel column chromatography to obtain Compound D as an intermediate compound. The chemical formula of the Compound D is as follows.

[Chemical Formula 90]

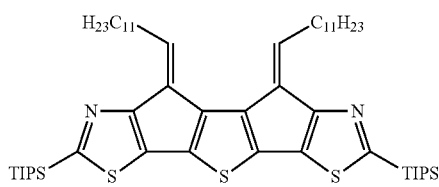

(D)

Synthesis of Compound E

Lithium aluminum hydride, dodecyl bromide, and tetrahydrofuran are added into an eggplant flask that has been dried by heating. The gas in the eggplant flask is purged with nitrogen gas, and while stirring, the mixed solution is cooled with ice water to approximately 15° C. A tetrahydrofuran solution of the Compound D is slowly added to the reaction solution, and the temperature of the solution is then increased to a room temperature, and thereafter, the solution is reacted for 2 hours while stirring. Thereafter, water is added to the reaction solution to terminate the reaction, and tetrahydrofuran is then distilled away, and the resultant is then extracted with ethyl acetate. The organic layer is dried over magnesium sulfate and is then concentrated under a reduced pressure, and thereafter, the resultant is purified by silica gel column chromatography to obtain Compound E as an intermediate compound. The chemical formula of the Compound E is as follows.

[Chemical Formula 91]

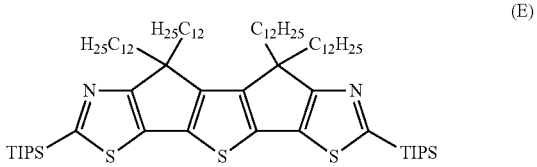

(E)

Synthesis of Nitrogen-Containing Condensed Ring Compound (Compound F)

The Compound E and tetrahydrofuran are added into an eggplant flask that has been dried by heating. The gas in the eggplant flask is purged with nitrogen gas, and the mixture is then cooled to −78° C., and lithium diisopropylamide is then added thereto to conduct a reaction. After the obtained mixture has been stirred for 1 hour, water is added to the reaction mixture at −78° C., and the temperature of the mixture is then increased to a room temperature, followed by extraction with chloroform. The organic layer is dried over magnesium sulfate and is then concentrated under a reduced pressure, and thereafter, the resultant is purified by silica gel column chromatography to obtain Compound F as a desired product.

[Chemical Formula 92]

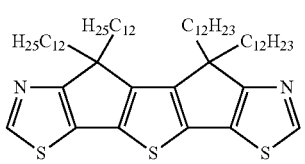

(F)

Example 2

Synthesis of Compound G 1,4-Dibromo-2,5-benzenedicarboxylic acid (10 g, 30.87 mmol), a catalytic amount of dimethyl formamide, and an excessive amount of thionyl chloride were added into an eggplant flask, and the gas in the eggplant flask was purged with nitrogen gas, and the mixture was then refluxed for 1 hour. After completion of the reaction, thionyl chloride was distilled away in a vacuum. Subsequently, the resultant was cooled to 0° C., and triethylamine (25.89 mL, 185.2 mmol) was then added thereto, and further, piperidine (18.36 mL, 185.2 mmol) was added dropwise to the mixture. After completion of the dropwise addition, the obtained mixture was stirred at a room temperature. Two hours later, water was added to the reaction mixture, and the thus obtained mixture was then extracted with dichloromethane. The organic layer was dried over magnesium sulfate and was then concentrated under a reduced pressure. The generated solid was washed with methanol to obtain Compound G (11.76 g, yield: 83%)

as a desired product in the form of a white solid. The analysis results and chemical formula of the obtained Compound G are as follows.

¹H NMR (400 MHz, CDCl₃): δ (ppm)=7.44 (s, 2H).
GC-MS (DI): m/z=457 (M⁺).

[Chemical Formula 93]

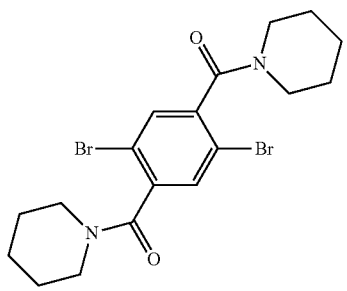

(G)

Synthesis of Compound H

The Compound G (2 g, 4.37 mmol), 2-triisopropylsilyl-5-tributyltin-thiazole (5.10 g, 9.60 mmol), tetrakis(triphenylphosphine)palladium(0) (505 mg, 0.44 mmol), and toluene (20 mL) were added into a test tube with lid that had been dried by heating, and the gas in the test tube was then purged with nitrogen gas, and the mixture was then refluxed for 10 hours. Subsequently, the reaction solution was filtrated with Celite and was then concentrated under a reduced pressure, and thereafter, the generated solid was washed with methanol. Thereby, Compound H (2.65 mg, yield: 78%) was obtained as a desired product in the form of a white solid. The analysis results and chemical formula of the obtained Compound H are as follows.

¹H NMR (400 MHz, CDCl₃): δ (ppm)=8.28 (s, 2H), 7.52 (s, 2H).

[Chemical Formula 94]

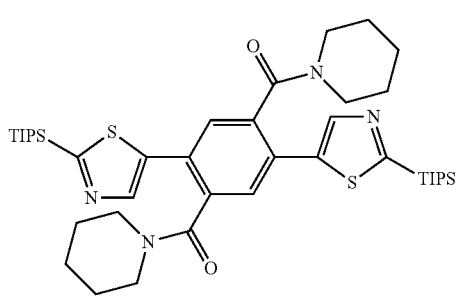

(H)

Synthesis of Compound I

The Compound H (500 mg, 0.642 mmol) and tetrahydrofuran (45 mL) were added into an eggplant flask that had been dried by heating. The gas in the eggplant flask was purged with nitrogen gas, and the mixture was then cooled to −78° C., and lithium diisopropylamide (1M, 14 mL, 7.77 mmol) was then added to the mixture to conduct a reaction. One hour later, water was added to the reaction mixture at −78° C., and the temperature of the mixture was then increased to a room temperature, followed by extraction with chloroform. The organic layer was dried over magnesium sulfate and was then concentrated under a reduced pressure. The resultant was purified by silica gel column chromatography (hexane/chloroform=2.5/1 (volume ratio)) to obtain Compound I (343 mg, yield: 88%) as a desired product in the form of a violet solid. The analysis results and chemical formula of the obtained Compound I are as follows.

TLC R_f=0.29 (hexane/chloroform=2.5/1 (volume ratio))
GC-MS (DI): m/z=609 (M⁺).

[Chemical Formula 95]

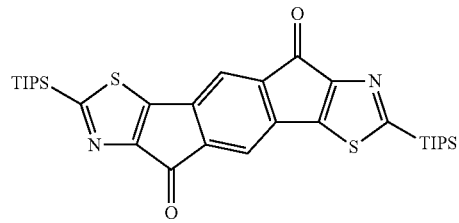

(I)

Synthesis of Compound J n-Dodecyl triphenylphosphonium bromide (1.01 g, 1.97 mmol) and tetrahydrofuran (10 mL) were added into an eggplant flask that had been dried by heating, and the gas in the eggplant flask was purged with nitrogen gas, and the mixture was then cooled to −78° C., and thereafter, n-butyllithium (1.97 mmol) was added to the reaction mixture, followed by stirring for 1 hour. Thereafter, the Compound I (400 mg, 0.657 mmol) dissolved in tetrahydrofuran (3.3 mL) was added to the reaction solution, and the obtained mixture was then reacted. One hour later, the temperature of the reaction mixture was increased to a room temperature, and the mixture was then stirred for 5 hours, and thereafter, water was added to the reaction mixture, followed by extraction with chloroform. The organic layer was dried over magnesium sulfate and was then concentrated under a reduced pressure. The resultant was purified by silica gel column chromatography (hexane) to obtain Compound J (455 mg, yield: 76%) as a desired product in the form of a yellow solid. The analysis results and chemical formula of the obtained Compound J are as follows.

¹H NMR (400 MHz, CDCl₃): δ (ppm)=7.66 (s, 2H), 6.77 (t, J=8.23 Hz, 2H), 3.20 (dd, J=15.5, 7.78 Hz, 4H), 1.69-1.13 (m), 0.91-0.85 (m, 8H).

TLC R_f=0.23 (hexane)
MS (TOF): m/z=912.87 (M⁺).

[Chemical Formula 96]

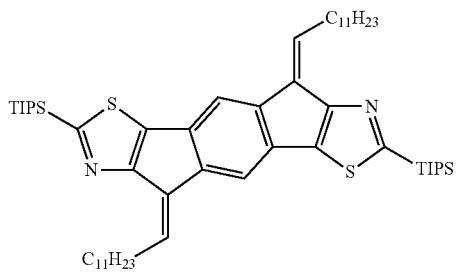

(J)

Synthesis of Compound K

Tetrahydrofuran (6 mL) and lithium aluminum hydride (50 mg, 1.31 mmol) were added into an eggplant flask that had been dried by heating, and the gas in the eggplant flask was then purged with nitrogen gas, and thereafter, 1-bromododecane was added to the flask, and the mixture was then cooled to 0° C., and the Compound J (200 mg, 0.219 mmol) dissolved in tetrahydrofuran (6 mL) was slowly added to the reaction mixture to conduct a reaction. One hour later, the temperature of the reaction solution was increased to a room temperature, and the mixture was then stirred for 3 hours, and water was then added to the reaction mixture, followed by extraction with ethyl acetate. The organic layer was dried over magnesium sulfate and was then concentrated under a reduced pressure. The resultant was purified by silica gel column chromatography (hexane/ethyl acetate=40/1 (volume ratio)) to obtain Compound K (147 mg, yield: 54%) as a desired product in the form of a yellow solid. The analysis results and chemical formula of the obtained Compound K are as follows.

$^1$H NMR (400 MHz, CDCl$_3$): δ (ppm)=7.35 (s, 2H), 2.22 (td, J=12.35, 4.57 Hz, 4H), 1.86 (td, J=12.35, 4.57 Hz, 4H), 1.48 (hept, J=7.3 Hz, 6H), 1.35-1.00 (m), 0.91-0.84 (m), 0.74 (m).

TLC R$_f$=0.03 (hexane/ethyl acetate=40:1 (volume ratio))
MS (TOF): m/z=1252.65 (M$^+$).

[Chemical Formula 97]

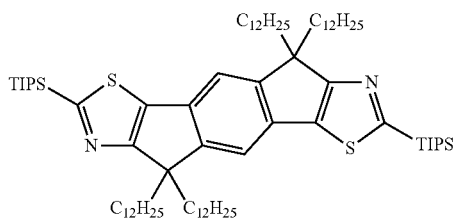

(K)

Synthesis of Nitrogen-Containing Condensed Ring Compound (Compound L)

The Compound K (2.67 g, 2.13 mmol) and tetrahydrofuran (20 mL) were added into an eggplant flask that had been dried by heating. The obtained mixture was cooled to 0° C., and tetrabutylammonium fluoride (1 M, 8.52 mL, 8.52 mmol) was added to the mixture to conduct a reaction. One hour later, water was added to the reaction mixture, and the mixture was then extracted with chloroform. The organic layer was dried over magnesium sulfate and was then concentrated under a reduced pressure. The resultant was purified by silica gel column chromatography (hexane/CHCl$_3$=5:1) to obtain Compound L (1.63 g, 81%) as a desired product in the form of a white solid. The analysis results and chemical formula of the obtained Compound L are as follows.

$^1$H NMR (400 MHz, CDCl$_3$): δ (ppm)=8.75 (s, 2H), 7.37 (s, 2H), 2.24-2.15 (m, 4H), 1.97-1.87 (m, 4H), 1.33-1.00 (m, 72H), 0.90-0.83 (m, 12H), 0.83-0.70 (m, 8H).

TLC R$_f$=0.14 (hexane/ethyl acetate=5:1)

UV-Vis absorption peak wavelength (dilute chloroform solution): 364,348 nm

[Chemical Formula 98]

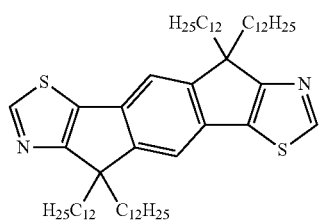

(L)

Example 3

Synthesis of Compound M

The Compound I (47 mg, 0.077 mmol), 2,2-dibutyl-1,3-propanediol (58 mg, 0.031 mmol), p-toluenesulfonic acid (133 mg, 0.77 mmol), and benzene (30 mL) were added into an eggplant flask that had been dried by heating, and the gas in the eggplant flask was then purged with nitrogen gas, and the mixture was then refluxed for 8 hours. The reaction solution was filtrated with Celite and was then concentrated under a reduced pressure, and thereafter, the resultant was purified by silica gel column chromatography (hexane/ethyl acetate=20/1 (volume ratio)) to obtain Compound M (42 mg, 0.066 mmol) as a desired product. The analysis results and chemical formula of the obtained Compound M are as follows.

$^1$H NMR (400 MHz, CDCl$_3$): δ (ppm)=8.68 (s, 2H), 7.46 (s, 2H), 4.60 (s, 2H), 4.57 (s, 2H), 3.82 (s, 2H), 3.79 (s, 2H).

[Chemical Formula 99]

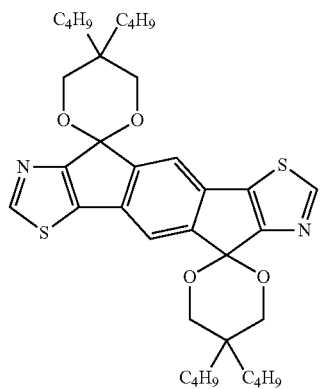

(M)

Synthesis of Compound N

The Compound M (237 mg, 0.37 mmol) and tetrahydrofuran (5 mL) were added into an eggplant flask that had been dried by heating. The gas in the eggplant flask was purged with nitrogen gas, and the mixture was then cooled to −78° C., and n-butyllithium (0.71 mL, 1.12 mmol) was then added to the mixture to conduct a reaction. One hour later, tributyltin chloride (0.33 mL, 1.23 mmol) was added to the reaction mixture at −78° C., and the temperature of the mixture was then increased to a room temperature. One hour later, water was added to the reaction mixture, and the thus obtained mixture was then extracted with ethyl acetate. The organic layer was dried over magnesium sulfate and was then concentrated under a reduced pressure. The resultant was purified with an aluminum column (hexane/CDCl$_3$=10/1 (volume ratio)) to obtain Compound N (396 mg, yield: 88%) as a desired product. The analysis results and chemical formula of the obtained Compound N are as follows.

$^1$H NMR (400 MHz, CDCl$_3$): δ (ppm)=7.41 (s, 2H), 4.76 (s, 2H), 4.73 (s, 2H), 3.77 (s, 2H), 3.74 (s, 2H).

[Chemical Formula 100]

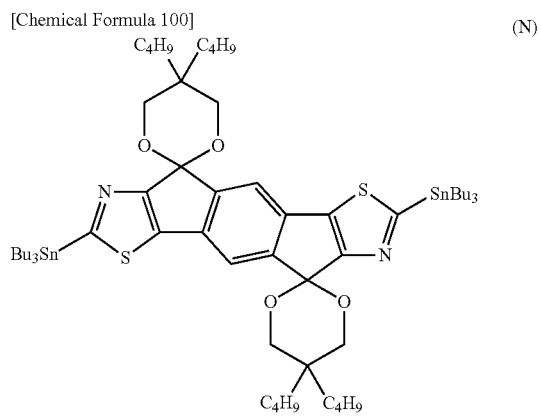

(N)

Synthesis of Compound O

The Compound N (322 mg, 0.27 mmol), 4′-bromo-2,2,2-trifluoroacetophenone (201 mg, 0.80 mmol), tetrakis(triphenylphosphine)palladium(0) (31 mg, 0.027 mmol), and toluene (3 mL) were added into a test tube with lid that had been dried by heating, and the gas in the test tube was then purged with nitrogen gas, and the mixture was then refluxed for 13 hours. Subsequently, the reaction solution was filtrated with Celite and was then concentrated under a reduced pressure, and thereafter, the obtained solid was washed with methanol and diethyl ether. To an eggplant flask, the obtained red solid, acetic acid, and concentrated hydrochloric acid were added, and the obtained mixture was then heated to 100° C. Two hours later, the reaction mixture was cooled to a room temperature, and a solid generated as a result of addition of water was washed with water, methanol, and diethyl ether. Thereafter, sublimation purification was carried out under a reduced pressure to obtain Compound O (77 mg, yield: 45%) as a desired product in the form of a dark green solid.

[Chemical Formula 101]

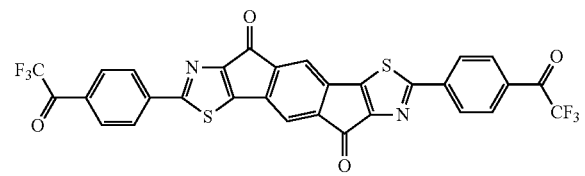

(O)

Synthesis of Nitrogen-Containing Condensed Ring Compound (Compound P)

The same operations as those in the synthesis of the Compound D in Example 1 are carried out with the exception that the Compound O is used instead of the Compound C, and thereafter, the same operations as those in the synthesis of Compounds E and F in Example 1 are carried out with the exception that the obtained compounds are successively used in the operations, thereby obtaining Compound P. The chemical formula of the Compound P is as follows.

[Chemical Formula 102]

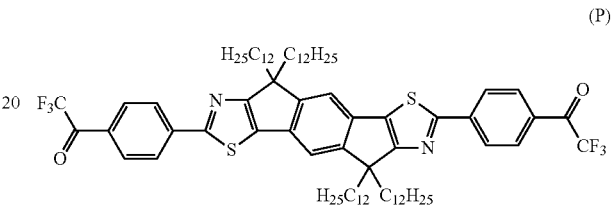

(P)

Example 4

Production of Organic Thin Film Element 1 and Evaluation of Transistor Properties A silicon oxide film to be used as an insulating layer is formed by thermal oxidation to have a thickness of 300 nm on the surface of a p-type silicon substrate to be used as a gate electrode, which has been doped at a high concentration. A source electrode and a drain electrode are formed on this substrate, and the obtained substrate with electrodes is subjected to ultrasonic washing with acetone and isopropyl alcohol, and it is further irradiated with ozone UV, and the surface of the substrate is then washed.

Herein, when the Compound P of Example 3 is added to chloroform, since it is completely dissolved in the chloroform, it can be confirmed that the Compound P is soluble in an organic solvent.

A chloroform solution of the obtained Compound P is used as a coating solution, and an organic thin film of the Compound P is accumulated on the above washed substrate according to a spin-coating method, so as to produce an organic thin film element 1.

When the transistor properties of the obtained organic thin film element 1 are measured using a semiconductor parameter analyzer under conditions in which the gate voltage Vg and the source-drain voltage Vsd are changed in a range of 0 to 80 V in a vacuum, high Id-Vg properties of an n-type semiconductor can be obtained, and thus, it can be confirmed that the Compound N can be used as an organic n-type semiconductor excellent in terms of an electron transport property.

Example 5

Synthesis of Compound Q

The Compound L (1.63 g, 1.73 mmol) and chloroform (20 mL) were added into an eggplant flask that had been dried by heating. The mixture was cooled to 0° C., and N-bromosuccinimide (1.85 g, 10.38 mmol) was slowly added to the reaction mixture to conduct a reaction. One hour later, the temperature of the reaction mixture was increased to a room temperature, and the mixture was then stirred for 10 hours. Thereafter, water was added to the reaction solution, and the mixture was then extracted with chloroform. The organic phase was dried over magnesium sulfate and was then concentrated under a reduced pressure. The resultant was purified by silica gel column chromatography (chloroform) to obtain Compound Q (1.31 g, 69%) as a desired product in the form of a white solid. The analysis results and chemical formula of the obtained Compound Q are as follows.

$^1$H NMR (400 MHz, CDCl$_3$): δ (ppm)=7.28 (s, 2H), 2.24-2.15 (m, 4H), 1.97-1.87 (m, 4H), 1.33-1.00 (m, 72H), 0.90-0.83 (m, 12H), 0.83-0.70 (m, 8H).

[Chemical Formula 103]

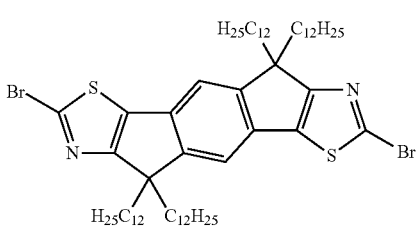

Synthesis of Polymer R

The Compound Q (300 mg, 0.273 mmol), 2,1,3-benzothiadiazole-4,7-bis(boronic acid pinacol ester) (106 mg, 0.273 mmol), tetrakis(triphenylphosphine)palladium(0) (32 mg, 0.027 mmol), a potassium carbonate aqueous solution (2 M, 2.73 mmol), tetrahydrofuran (11 mL), and water (5 mL) were added into a test tube with lid that had been dried by heating, and the gas in the test tube was then purged with nitrogen gas, and the mixture was then refluxed for 72 hours. Thereafter, a reaction solution was added dropwise to methanol (100 mL) to which 10% hydrochloric acid (5 mL) had been added, and the obtained mixture was then left at rest for 1 hour. Thereafter, the precipitated solid was collected by filtration, and the obtained solid was then dissolved in chloroform (30 mL). The chloroform solution was added dropwise to methanol (300 mL), and the obtained solution was then left at rest for 1 hour. Thereafter, the precipitated solid was collected by filtration, and it was then purified by a Soxhlet extraction method (in the order of methanol, acetone, hexane, and chloroform). After completion of the purification, Polymer R (chloroform fraction 100 mg, 34%) was obtained as a desired product in the form of a blue solid. The analysis results and chemical formula of the obtained Polymer R are as follows.

GPC: Mn=30,797 g/mol, Mw=64,821 g/mol, PDI=2.1

UV-Vis absorption peak wavelength (dilute chloroform solution): 616,394,328 nm

[Chemical Formula 104]

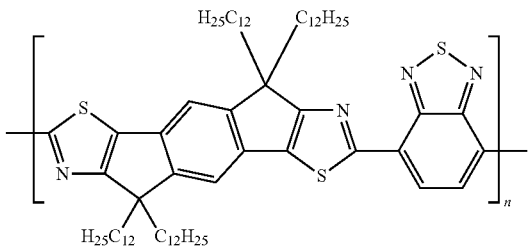

Example 6

Synthesis of Polymer S

The Compound Q (300 mg, 0.273 mmol), 5,5'-bis(tributylstannyl)-2,2'-bithiophene (203 mg, 0.273 mmol), tetrakis(triphenylphosphine)palladium(0) (32 mg, 0.027 mmol), and toluene (5 mL) were added into a test tube with lid that had been dried by heating, and the gas in the test tube was then purged with nitrogen gas, and the mixture was then refluxed for 14 hours. Thereafter, the reaction solution was added dropwise to methanol (100 mL) to which 10% hydrochloric acid (5 mL) had been added, and the obtained mixture was then left at rest for 1 hour. Thereafter, the precipitated solid was collected by filtration, and it was then purified by a Soxhlet extraction method (in the order of methanol, acetone, hexane, and chloroform). After completion of the purification, Polymer S-1 (chloroform fraction 12 mg, 4%) and Polymer S-2 (hexane fraction 250 mg, 83%) were obtained as desired products in the form of dark red solids. The analysis results and chemical formulae of the obtained Polymers S(S-1 and S-2) are as follows.

Polymer S-1 (Chloroform Fraction)
GPC: Mn=15,116 g/mol, Mw=30,999 g/mol, PDI=2.1
UV-Vis absorption peak wavelength (dilute chloroform solution): 557,525,260 nm
Polymer S-2 (hexane fraction)
GPC: Mn=10,016 g/mol, Mw=13,981 g/mol, PDI=1.4
UV-Vis absorption peak wavelength (dilute chloroform solution): 563 (shoulder), 521,341,262 nm

[Chemical Formula 105]

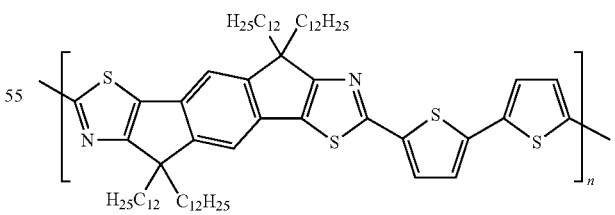

Example 7

Synthesis of Polymer T

The Compound Q (50 mg, 0.045 mmol), 4,7-diethynylbenzo[c][1,2,5]thiadiazole (8.3 mg, 0.045 mmol), tetrakis (triphenylphosphine)palladium(0) (5 mg, 0.005 mmol), copper iodide (1.7 mg, 0.010 mmol), tetrahydrofuran (0.5 mL), and triethylamine (0.5 mL) were added into a test tube with lid that had been dried by heating, and the gas in the test tube was then purged with nitrogen gas, and the mixture was then stirred at 75° C. for 48 hours. Thereafter, the reaction solution was added dropwise to methanol (100 mL) to which 10% hydrochloric acid (5 mL) had been added, and the obtained mixture was then left at rest for 1 hour. Thereafter, the precipitated solid was collected by filtration, and it was then purified by a Soxhlet extraction method (in the order of methanol, acetone, hexane, and chloroform). After completion of the purification, Polymer T (6 mg, 12%) was obtained as a desired product in the form of a violet solid. The analysis results and chemical formula of the obtained Polymer T are as follows.

GPC: (chloroform fraction) Mn=31,028 g/mol, Mw=104,473 g/mol, PDI=3.4

[Chemical Formula 106]

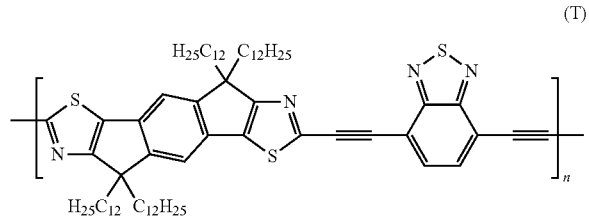

(T)

Example 8

Production of Organic Thin Film Element 2 and Evaluation of Solar Cell Properties The Polymer R synthesized in Example 5 was mixed with poly(3-hexylthiophene) (P3HT: manufactured by Sigma-Aldrich) at a ratio of Polymer R/P3HT=2/1 (mass ratio), and the mixture was then dissolved in orthodichlorobenzene to prepare a coating solution, in which a total concentration of the Polymer R and P3HT was 1.0% by weight. Since the Polymer G and P3HT were completely dissolved in orthodichlorobenzene, it could be confirmed that the Polymer R is soluble in an organic solvent.

Subsequently, a suspension of poly(3,4)ethylenedioxythiophene/polystyrene sulfonic acid (manufactured by Starck Vitec, Baytron(registered trademark) PAI4083:PEDOT) was filtrated through a 0.2-μm membrane filter. According to a spin-coating method, the thus obtained filtrate was applied onto an ITO film with a thickness of 150 nm that had been formed on a glass substrate by a sputtering method, thereby forming a thin film with a thickness of 44 nm. This thin film was dried by heating on a hot plate at 200° C. for 10 minutes.

Subsequently, the coating solution of the Polymer R and P3HT was applied onto the above described substrate (the substrate coated with PEDOT) by a spin-coating method to form an organic thin film with a thickness of approximately 90 nm which contained the Polymer R. Thereafter, the film was subjected to a heat treatment in a nitrogen atmosphere at 130° C. for 10 minutes. The light absorption terminal wavelength of the formed organic thin film was found to be 730 nm. Thereafter, calcium with a thickness of 8 nm was deposited via evaporation on the organic thin film, using a vacuum evaporation machine, and after that, Al with a thickness of 100 nm was also deposited via evaporation thereon, thereby obtaining an organic thin film element 2. The shape of the obtained organic thin film element 2 was a square with a size of 2 mm×2 mm.

Using a solar simulator (manufactured by Bunkoukeiki Co., Ltd.; trade name: OTENTO-SUNII: AM 1.5 G filter; irradiance: 100 mW/cm$^2$), a constant amount of light was applied to the obtained organic thin film element 2, and the thus generated current and voltage were then measured, so as to obtain photoelectric conversion efficiency, short circuit current density, open circuit voltage, and fill factor. Jsc (short circuit current density)=0.15 mA/cm$^2$, Voc (open circuit voltage)=0.64 V, ff (fill factor)=0.40, and photoelectric conversion efficiency ($\eta$)=0.04%, and thus, it was confirmed that the organic thin film element 2 exhibits solar cell properties. In addition, based on this fact, it was also confirmed that the Polymer R can be used as an organic semiconductor.

Example 9

Production of Organic Thin Film Element 3 and Evaluation of Solar Cell Properties The Polymer R synthesized in Example 5 was mixed with Fullerene C70PCBM (phenyl C71-butyric acid methyl ester, manufactured by Frontier Carbon Corporation) at a ratio of Polymer R/C70PCBM=2/1 (mass ratio), and the obtained mixture was then dissolved in orthodichlorobenzene to prepare a coating solution, in which a total concentration of the Polymer R and C70PCBM was 0.75% by weight.

The thus obtained coating solution of the Polymer R and C70PCBM was applied onto a PEDOT-coated substrate according to a spin-coating method in the same manner as that in Example 8, thereby forming an organic thin film with a thickness of approximately 96 nm which contained the Polymer R. Subsequently, the film was subjected to a heat treatment in a nitrogen atmosphere at 130° C. for 10 minutes. The light absorption terminal wavelength of the formed organic thin film was found to be 830 nm. Thereafter, calcium with a thickness of 8 nm was deposited via evaporation on the organic thin film, using a vacuum evaporation machine, and after that, Al with a thickness of 100 nm was also deposited via evaporation thereon, thereby obtaining an organic thin film element 3. The shape of the obtained organic thin film element 3 was a square with a size of 2 mm×2 mm.

Using the same solar simulator as used in Example 8, a constant amount of light was applied to the obtained organic thin film element 3, and the thus generated current and voltage were then measured, so as to obtain photoelectric conversion efficiency, short circuit current density, open circuit voltage, and fill factor. Jsc (short circuit current density)=0.89 mA/cm$^2$, Vac (open circuit voltage)=0.58 V, ff (fill factor)=0.21, and photoelectric conversion efficiency ($\eta$)=0.11%, and thus, it was confirmed that the organic thin film element 3 exhibits solar cell properties. In addition, based on this fact, it was also confirmed that the Polymer R can be used as an organic semiconductor.

REFERENCE SIGNS LIST

1 . . . substrate, 2 . . . active layer, 2a . . . active layer, 3 . . . insulating layer, 4 . . . gate electrode, 5 . . . source electrode, 6 . . . drain electrode, 7a . . . first electrode, 7b . . . second electrode, 8 . . . charge generation layer, 100 . . . organic thin film transistor according to the first embodiment, 110 . . . organic thin film transistor according to the second embodiment, 120 . . . organic thin film transistor according to the third embodiment, 130 . . . organic thin film transistor according to the fourth embodiment, 140 . . . organic thin film transistor according to the fifth embodiment, 150 . . . organic thin film transistor according to the sixth embodiment, 160 . . . organic thin film transistor according to the seventh embodiment, 200 . . . solar cell according to the embodiment, 300 . . . optical sensor according to the first embodiment, 310 . . . optical sensor according to the second embodiment, and 320 . . . optical sensor according to the third embodiment.

The invention claimed is:

1. A nitrogen-containing condensed ring compound having a structural unit represented by the following formula (1-1) or a structural unit represented by the following formula (1-2):

[Chemical Formula 1]

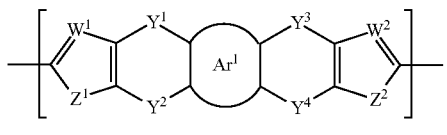

(1-1)

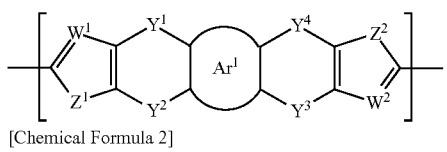

(1-2)

[Chemical Formula 2]

 (i)

 (ii)

 (iii)

 (iv)

 (v)

 (vi)

 (vii)

 (viii)

 (ix)

wherein, in the formulae (1-1) and (1-2),

Ar$^1$ represents an aromatic ring containing 4 or more carbon atoms and optionally having a substituent, one of Y$^1$ and Y$^2$ represents a single bond, and the other represents a group represented by —C(R$^{11}$)(R$^{12}$)— or a group represented by —C(=X$^1$)—; one of Y$^3$ and Y$^4$ represents a single bond, and the other represents a group represented by —C(R$^{21}$)(R$^{22}$)— or a group represented by —C(=X$^2$)—, wherein R$^{11}$, R$^{12}$, R$^{21}$ and R$^{22}$ each independently represent a hydrogen atom, a halogen atom, a monovalent group containing an alkane skeleton, or a cyano group, and at least one of Y$^1$, Y$^2$, Y$^3$ and Y$^4$ is a group represented by —C(R$^{11}$)(R$^{12}$)— or a group represented by —C(R$^{21}$)(R$^{22}$)—, wherein at least one of R$^{11}$ and R$^{12}$ and/or at least one of R$^{21}$ and R$^{22}$ are/is a monovalent group containing an alkane skeleton, and X$^1$ and X$^2$ each independently represent an oxygen atom, a sulfur atom, or a group represented by =C(A)$_2$, wherein A represents a hydrogen atom, a halogen atom, or a monovalent group, and a plurality of A may be identical to or different from each other, W$^1$ and W$^2$ each independently represent a group represented by —C(R$^{00}$)— or a group represented by N, and at least one of W$^1$ and W$^2$ is a group represented by N, and R$^{00}$ represents a hydrogen atom, a halogen atom, or a monovalent group, and Z$^1$ and Z$^2$ each independently represent a group represented by the formula (i), a group represented by the formula (ii), a group represented by the formula (iii), a group represented by the formula (iv), a group represented by the formula (v), a group represented by the formula (vi), a group represented by the formula (vii), a group represented by the formula (viii), or a group represented by the formula (ix), wherein the group represented by the formula (vii) and the group represented by the formula (viii) may be flipped horizontally, wherein, in the formula (vii), the formula (viii) and the formula (ix), R$^3$, R$^4$, R$^5$ and R$^6$ each independently represent a hydrogen atom, a halogen atom, or a monovalent group, and R$^3$ and R$^4$ may bind to each other to form a ring together with carbon atoms to which they bind.

2. The nitrogen-containing condensed ring compound according to claim 1, wherein, in the formula (1-1) and the formula (1-2), Y$^2$ and Y$^4$ each represent a single bond.

3. The nitrogen-containing condensed ring compound according to claim 1, wherein, in the formula (1-1) and the formula (1-2), Ar$^1$ represents a benzene ring or a thiophene ring.

4. The nitrogen-containing condensed ring compound according to claim 1, wherein, in the formula (1-1) and the formula (1-2), Z$^1$ and Z$^2$ each represent a group represented by the formula (ii).

5. The nitrogen-containing condensed ring compound according to claim 1, wherein, in the formula (1-1) and the formula (1-2), W$^1$ and W$^2$ each represent a group represented by =N.

6. The nitrogen-containing condensed ring compound according to claim 1, wherein the structural unit represented by the formula (1-1) is a structural unit represented by the following formula (3-01) and the structural unit represented by the formula (1-2) is a structural unit represented by the following formula (3-02):

[Chemical Formula 3]

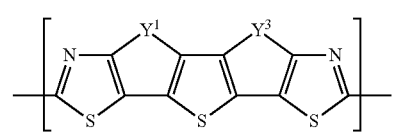

(3-01)

-continued

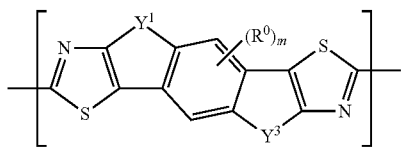
(3-02)

wherein, in the formula (3-01) and the formula (3-02), $Y^1$ and $Y^3$ have the same definitions as those described above, $R^0$ represents a substituent, and m represents an integer of 0 to 2.

7. A nitrogen-containing condensed ring polymer, which has a plurality of structural units represented by the following formula (1-1), or has a plurality of structural units represented by the following formula (1-2), or has at least one structural unit represented by the formula (1-1) and at least one structural unit represented by the formula (1-2):

[Chemical Formula 4]

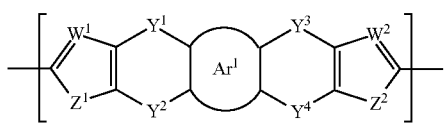
(1-1)

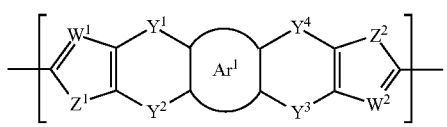
(1-2)

[Chemical Formula 5]

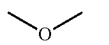
(i)

(ii)

(iii)

(iv)

(v)

(vi)

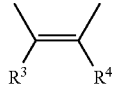
(vii)

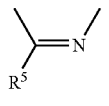
(viii)

(ix)

wherein, in the formulae (1-1) and (1-2),
$Ar^1$ represents an aromatic ring containing 4 or more carbon atoms and optionally having a substituent,
one of $Y^1$ and $Y^2$ represents a single bond, and the other represents a group represented by —$C(R^{11})(R^{12})$— or a group represented by —$C(=X^1)$—; one of $Y^3$ and $Y^4$ represents a single bond, and the other represents a group represented by —$C(R^{21})(R^{22})$—; or a group represented by —$C(=X^2)$—, wherein $R^{11}$, $R^{12}$, $R^{21}$ and $R^{22}$ each independently represent a hydrogen atom, a halogen atom, a monovalent group containing an alkane skeleton, or a cyano group, and at least one of $Y^1$, $Y^2$, $Y^3$ and $Y^4$ is a group represented by —$C(R^{11})(R^{12})$— or a group represented by —$C(R^{21})(R^{22})$—, wherein at least one of $R^{11}$ and $R^{12}$ and/or at least one of $R^{21}$ and $R^{22}$ are/is a monovalent group containing an alkane skeleton, and $X^1$ and $X^2$ each independently represent an oxygen atom, a sulfur atom, or a group represented by =$C(A)_2$, wherein A represents a hydrogen atom, a halogen atom, or a monovalent group, and a plurality of A may be identical to or different from each other,
$W^1$ and $W^2$ each independently represent a group represented by —$C(R^{00})$— or a group represented by =N and at least one of $W^1$ and $W^2$ is a group represented by =N, and $R^{00}$ represents a hydrogen atom, a halogen atom, or a monovalent group, and
$Z^1$ and $Z^2$ each independently represent a group represented by the formula (i), a group represented by the formula (ii), a group represented by the formula (iii), a group represented by the formula (iv), a group represented by the formula (v), a group represented by the formula (vi), a group represented by the formula (vii), a group represented by the formula (viii), or a group represented by the formula (ix), wherein the group represented by the formula (vii) and the group represented by the formula (viii) may be flipped horizontally, wherein
in the formula (vii), the formula (viii) and the formula (ix), $R^3$, $R^4$, $R^5$ and $R^6$ each independently represent a hydrogen atom, a halogen atom, or a monovalent group, and $R^3$ and $R^4$ may bind to each other to form a ring together with carbon atoms to which they bind.

8. The nitrogen-containing condensed ring polymer according to claim 7, wherein, in the formula (1-1) and the formula (1-2), $Y^2$ and $Y^4$ each represent a single bond.

9. The nitrogen-containing condensed ring polymer according to claim 7, wherein, in the formula (1-1) and the formula (1-2), $Ar^1$ represents a benzene ring or a thiophene ring.

10. The nitrogen-containing condensed ring polymer according to claim 7, wherein, in the formula (1-1) and the formula (1-2), $Z^1$ and $Z^2$ each represent a group represented by the formula (ii).

11. The nitrogen-containing condensed ring polymer according to claim 7, wherein, in the formula (1-1) and the formula (1-2), $W^1$ and $W^2$ each represent a group represented by =N.

12. The nitrogen-containing condensed ring polymer according to claim 7, which further has a structural unit represented by the following formula (4):

[Chemical Formula 6]

$$-\!\!\!+\!\!Ar^2\!\!+\!\!\!-$$ (4)

wherein $Ar^2$ represents an aromatic hydrocarbon group optionally having a substituent, a heterocyclic group optionally having a substituent, a group represented by —$CR_a$=$CR_b$—, or a group represented by —C≡C—, wherein $R_a$ and $R_b$ each independently represent a hydrogen atom, a halogen atom, an alkyl group containing 1 to 20 carbon atoms and optionally having a substituent, an aryl group containing 6 to 60 carbon atoms and optionally having a substituent, a heterocyclic group containing 4 to 60 carbon atoms and optionally having a substituent, or a cyano group.

13. The nitrogen-containing condensed ring polymer according to claim 7, which further has a structural unit represented by the following formula (5):

[Chemical Formula 7]

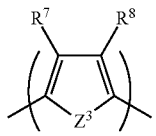
(5)

[Chemical Formula 8]

(xi)

(xii)

(xiii)

(xiv)

(xv)

(xvi)

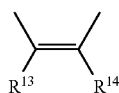
(xvii)

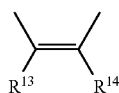
(xviii)

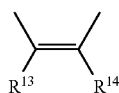
(xix)

wherein, in the formula (5), $R^7$ and $R^8$ each independently represent a hydrogen atom, a halogen atom, or a monovalent group, and $Z^3$ represents a group represented by the formula (xi), a group represented by the formula (xii), a group represented by the formula (xiii), a group represented by the formula (xiv), a group represented by the formula (xv), a group represented by the formula (xvi), a group represented by the formula (xvii), a group represented by the formula (xviii), or a group represented by the formula (xix), wherein the group represented by the formula (xvii) and the group represented by the formula (xviii) may be flipped horizontally, and wherein $R^7$ and $R^8$ may bind to each other to form a ring together with carbon atoms to which they bind, wherein in the formula (xvii), the formula (xviii) and the formula (xix), $R^{13}$, $R^{14}$, $R^{15}$ and $R^{16}$ each independently represent a hydrogen atom, a halogen atom, or a monovalent group, and $R^{13}$ and $R^{14}$ may bind to each other to form a ring together with carbon atoms to which they bind.

14. The nitrogen-containing condensed ring polymer according to claim 13, wherein, in the formula (5), $Z^3$ represents a group represented by the formula (xii).

15. An organic thin film containing the nitrogen-containing condensed ring compound according to claim 1.

16. An organic thin film element comprising the organic thin film according to claim 15.

17. An organic thin film transistor comprising the organic thin film according to claim 15.

18. An organic solar cell comprising the organic thin film according to claim 15.

19. An organic thin film containing the nitrogen-containing condensed ring polymer according to claim 7.

* * * * *